(12) United States Patent
Mosse et al.

(10) Patent No.: US 10,502,863 B2
(45) Date of Patent: Dec. 10, 2019

(54) DIAGENETIC AND DEPOSITIONAL ROCK ANALYSIS

(71) Applicant: Schlumberger Technology Corporation, Sugar Land, TX (US)

(72) Inventors: Laurent Mosse, Buenos Aires (AR); Helena Gamero Diaz, Frisco, TX (US); Josselin Kherroubi, Clamart (FR); Christina Calvin, Houston, TX (US); Erik Rylander, Frisco, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 78 days.

(21) Appl. No.: 15/550,792

(22) PCT Filed: Feb. 12, 2016

(86) PCT No.: PCT/US2016/017793
§ 371 (c)(1),
(2) Date: Aug. 13, 2017

(87) PCT Pub. No.: WO2016/130945
PCT Pub. Date: Aug. 18, 2016

(65) Prior Publication Data
US 2018/0031732 A1 Feb. 1, 2018

Related U.S. Application Data

(60) Provisional application No. 62/116,329, filed on Feb. 13, 2015, provisional application No. 62/116,320, filed on Feb. 13, 2015, provisional application No. 62/190,987, filed on Jul. 10, 2015, provisional application No. 62/258,350, filed on Nov. 20, 2015.

(51) Int. Cl.
*G01V 11/00* (2006.01)
*G01N 33/24* (2006.01)
*G01V 99/00* (2009.01)

(52) U.S. Cl.
CPC ............ *G01V 11/00* (2013.01); *G01V 99/005* (2013.01); *G01N 33/24* (2013.01); *G01V 2210/66* (2013.01)

(58) Field of Classification Search
CPC .. G01V 11/00; G01V 99/005; G01V 2210/66; G01N 33/24
See application file for complete search history.

(56) References Cited

U.S. PATENT DOCUMENTS

| 7,983,885 B2 | 7/2011 | Suarez-Rivera et al. |
| 2012/0221306 A1 | 8/2012 | Francis et al. |

(Continued)

FOREIGN PATENT DOCUMENTS

| GB | 2223842 A | 4/1990 |
| GB | 2436615 B | 8/2008 |

(Continued)

OTHER PUBLICATIONS

Senecal et al., Monterey Formation Analysis: State-of-the-Art Interpretation of Lithology and Identification of Fractures and Fluid Type in Fine-Grained, Mineralogically Variable Rocks, Jun. 17-20, 1985, SPWLA 26th Annual Logging Symposium, 16 pp. (Year: 1985).*

(Continued)

*Primary Examiner* — Toan M Le
(74) *Attorney, Agent, or Firm* — Mitchell M. Blakely

(57) ABSTRACT

A method can include receiving data for a geologic environment where the data include data acquired via different types of borehole tool sensors; based at least in part on the data, determining rock composition of the geologic environment where the rock composition includes depositional components and diagenetic components; and, based at least in part on the rock composition, outputting a stratigraphic model of at least a portion of the geologic environment.

20 Claims, 32 Drawing Sheets

(56) References Cited

U.S. PATENT DOCUMENTS

2013/0325349 A1* 12/2013 Bunting .................. G01V 9/00
702/11
2014/0297186 A1 10/2014 Roberto et al.
2014/0379312 A1 12/2014 Dedontney et al.

FOREIGN PATENT DOCUMENTS

WO 2005/104002 A1 11/2005
WO 2011/073861 A2 6/2011

OTHER PUBLICATIONS

International Preliminary Report on Patentability for the equivalent International patent application PCT/US2016/017793 dated Aug. 24, 2017.
Gamero, et al., "sCore: A Mineralogy Based Classification Scheme for Organic Mudstones," SPE Annual Technical Conference and Exhibition, New Orleans, Louisiana, USA, Sep. 30-Oct. 2, 2013, pp. 1-17.
Ratcliffe, et al., "Application of inorganic whole-rock geochemistry to shale resource plays: an example from the Eagle Ford Shale Formation, Texas," The Sedimentary Record, Jun. 2012, pp. 4-9.
Rowe, et al., "The quantification and application of handheld energy-dispersive x-ray fluorescence (ED-XRF) in mudrock chemostratigraphy and geochemistry," Chemical Geology, 2012, v. 324-325, p. 122-131.
International Search Report and Written Opinion for the equivalent International patent application PCT/US2016/017793 dated May 17, 2016.
Extended Search Report for the equivalent European patent application 16749981.3 dated Oct. 10, 2018.

* cited by examiner

Table 1500

| Ashbed | Mineralogy | Thickness | Strenght | Distance to Target | Summary | Recommendations |
|---|---|---|---|---|---|---|
| 1 | Fe-oxide - b/c high density | <1" | Competent | Far | | fluid compatibility |
| | Kaolinite - b/c no clay-bound water | | | | | |
| 2 | Fe-oxide - b/c high density | 4" | Degraded | Close | | lateral continuity |
| | Kaolinite - b/c no clay-bound water | | | | | fluid compatibility |
| | | | | | | geomechancial properties |

Fig. 15

DIAGENETIC AND DEPOSITIONAL ROCK ANALYSIS

RELATED APPLICATIONS

This application claims priority to and the benefit of a U.S. Provisional Application having Ser. No. 62/116,320, filed 13 Feb. 2015 (IS15.0089-US-PSP); a U.S. Provisional Application having Ser. No. 62/116,329, filed 13 Feb. 2015 (IS15.0119-US-PSP); a U.S. Provisional Application having Ser. No. 62/190,987, filed 10 Jul. 2015 (IS15.0302-US-PSP); and a U.S. Provisional Application having Ser. No. 62/258,350, filed 20 Nov. 2015 (IS15.1315-US-PSP), the four aforementioned U.S. Provisional applications are incorporated by reference herein.

BACKGROUND

Rock can be formed of an aggregate of material. For example, rock may be formed of one or more of minerals, organic matter, volcanic glass, etc. Rock may include a single type of mineral or many types of minerals. Rocks may be characterized by types such as, for example, sedimentary rocks like sandstone and limestone (e.g., formed at the Earth's surface through deposition of sediments derived from weathered rocks, biogenic activity or precipitation from solution); igneous rocks (e.g., originating deeper within the Earth, where the temperature may be high enough to melt rocks, to form magma that can crystallize within the Earth or at the surface by volcanic activity); and metamorphic rocks (e.g., formed from other preexisting rocks during episodes of deformation of the Earth at temperatures and pressures high enough to alter minerals but inadequate to melt them). Changes to rock may occur by the activity of fluids in the Earth and movement of igneous bodies or regional tectonic activity. Rocks may be recycled from one type to another by the constant changes in the Earth. As such, rocks may be considered to have associated "histories", which can add a temporal aspect to rocks found today.

SUMMARY

In accordance with some embodiments, a method is performed that includes: receiving data for a geologic environment where the data include data acquired via different types of borehole tool sensors; based at least in part on the data, determining rock composition of the geologic environment where the rock composition includes depositional components and diagenetic components; and, based at least in part on the rock composition, outputting a stratigraphic model of at least a portion of the geologic environment.

In some embodiments, an aspect includes determining detrital mineral composition values associated with at least one of a plurality of depositional components, calculating a detrital index value based at least in part on the detrital mineral composition values and, based at least in part on the detrital index value, attributing a portion of a stratigraphic model to a particular geological source.

In some embodiments, an aspect includes determining diagenetic mineral composition values associated with at least one of a plurality of diagenetic components, calculating a diagenetic index value based at least in part on the diagenetic mineral composition values and, based at least in part on the diagenetic index value, attributing a portion of a stratigraphic model to a particular geological source.

In some embodiments, an aspect includes determining detrital mineral composition values associated with at least one of a plurality of depositional components and calculating a detrital index value based at least in part on the detrital mineral composition values; determining diagenetic mineral composition values associated with at least one of a plurality of diagenetic components and calculating a diagenetic index value based at least in part on the diagenetic mineral composition values; and, based at least in part on the detrital index value and the diagenetic index value, attributing a portion of a stratigraphic model to a particular geological source.

In some embodiments, an aspect includes a detrital index value that is normalized by a quartz composition value and/or a diagenetic index value that is normalized by a calcite composition value.

In some embodiments, an aspect includes elemental analysis.

In some embodiments, an aspect includes a stratigraphic model that includes a reservoir model, a completion model or a reservoir model and a completion model.

In some embodiments, an aspect includes determining that rock composition of a geologic environment includes at least one igneous deposit.

In some embodiments, an aspect includes determining that rock composition of a geologic environment includes at least one igneous deposit that is a weathered volcanic ash bed.

In some embodiments, an aspect includes adjusting a completion plan based at least in part on at least one igneous deposit.

In some embodiments, an aspect includes determining that rock composition of a geologic environment includes at least one igneous deposit that has a thickness less than approximately 10 cm.

In some embodiments, an aspect includes receiving data from different types of borehole tool sensors where at least one of the different types of borehole tool sensors acquires raw data with a resolution less than approximately 10 cm.

In some embodiments, an aspect includes receiving data from different types of borehole tool sensors where at least one sensor is selected a group that includes a micro-resistivity sensor, a photoelectric factor sensor, an image sensor, a dielectric and conductivity dispersion sensor, a neutron porosity sensor, and an ultrasonic sensor.

In some embodiments, an aspect includes receiving data where the data include sonic data, NMR data and gamma ray spectroscopy data.

In some embodiments, an aspect includes determining at least one pore characteristic that includes a surface to volume ratio or a volume to surface ratio based at least in part on a portion of NMR data and determining at least one value for the Thomsen gamma parameter based at least in part on at least a portion of sonic data.

In some embodiments, an aspect includes receiving data that include counting rates in a formation for each of a plurality of radiation detectors.

In some embodiments, an aspect includes computing density values and photoelectric factor values based at least in part on counting rates; applying density depth match filters to the density values to generated filtered density values; and applying photoelectric factor depth match filters to the photoelectric factor values to generate filtered photoelectric factor values where each of a plurality of radiation detectors is associated with a corresponding depth match filter and a corresponding photoelectric factor filter.

In some embodiments, an aspect includes outputting a stratigraphic model that is based at least in part on generated filtered density values and generated filtered photoelectric factor values.

In accordance with some embodiments, a system includes: a processor; memory accessibly by the processor; instructions stored in the memory and executable by the processor to instruct the system to receive data for a geologic environment where the data include data acquired via different types of borehole tool sensors; based at least in part on the data, determine rock composition of the geologic environment where the rock composition includes depositional components and diagenetic components; and, based at least in part on the rock composition, output a stratigraphic model of at least a portion of the geologic environment.

In accordance with some embodiments, one or more computer-readable storage media include processor-executable instructions where the processor-executable instructions include instructions to instruct a computer to: receive data for a geologic environment where the data include data acquired via different types of borehole tool sensors; based at least in part on the data, determine rock composition of the geologic environment where the rock composition includes depositional components and diagenetic components; and, based at least in part on the rock composition, output a stratigraphic model of at least a portion of the geologic environment. Various other apparatuses, systems, methods, etc., are also disclosed.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

Features and advantages of the described implementations can be more readily understood by reference to the following description taken in conjunction with the accompanying drawings.

FIG. 15 illustrates an example of a table;

DETAILED DESCRIPTION

This description is not to be taken in a limiting sense, but rather is made merely for the purpose of describing the general principles of the implementations. The scope of the described implementations should be ascertained with reference to the issued claims.

Figure 1:
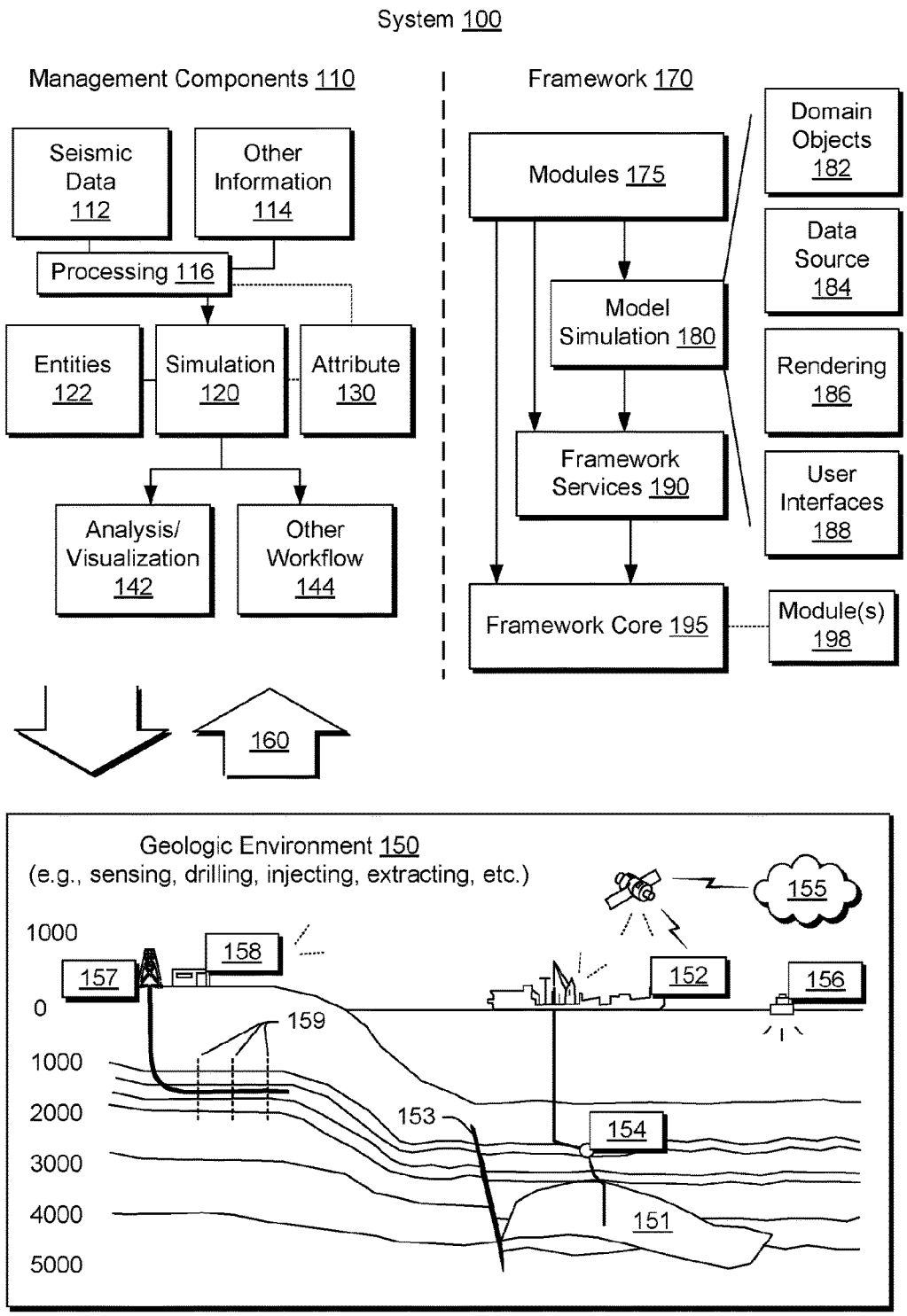
FIG. 1 illustrates an example system that includes various components for simulating a geological environment.

FIG. 1 shows an example of a system 100 that includes various management components 110 to manage various aspects of a geologic environment 150 (e.g., an environment that includes a sedimentary basin, a reservoir 151, one or more fractures 153, etc.). For example, the management components 110 may allow for direct or indirect management of sensing, drilling, injecting, extracting, etc., with respect to the geologic environment 150. In turn, further information about the geologic environment 150 may become available as feedback 160 (e.g., optionally as input to one or more of the management components 110).

In the example of FIG. 1, the management components 110 include a seismic data component 112, an additional information component 114 (e.g., well/logging data), a processing component 116, a simulation component 120, an attribute component 130, an analysis/visualization component 142 and a workflow component 144. In operation, seismic data and other information provided per the components 112 and 114 may be input to the simulation component 120.

In an example embodiment, the simulation component 120 may rely on entities 122. Entities 122 may include earth entities or geological objects such as wells, surfaces, reservoirs, etc. In the system 100, the entities 122 can include virtual representations of actual physical entities that are reconstructed for purposes of simulation. The entities 122 may include entities based on data acquired via sensing, observation, etc. (e.g., the seismic data 112 and other information 114). An entity may be characterized by one or more properties (e.g., a geometrical pillar grid entity of an earth model may be characterized by a porosity property). Such properties may represent one or more measurements (e.g., acquired data), calculations, etc.

In an example embodiment, the simulation component 120 may operate in conjunction with a software framework such as an object-based framework. In such a framework, entities may include entities based on pre-defined classes to facilitate modeling and simulation. A commercially available example of an object-based framework is the MICROSOFT™ .NET™ framework (Redmond, Wash.), which provides a set of extensible object classes. In the .NET™ framework, an object class encapsulates a module of reusable code and associated data structures. Object classes can be used to instantiate object instances for use by a program, script, etc. For example, borehole classes may define objects for representing boreholes based on well data. A model of a basin, a reservoir, etc. may include one or more boreholes where a borehole may be, for example, for measurements, injection, production, etc. As an example, a borehole may be a wellbore of a well, which may be a completed well (e.g., for production of a resource from a reservoir, for injection of material, etc.).

In the example of FIG. 1, the simulation component 120 may process information to conform to one or more attributes specified by the attribute component 130, which may include a library of attributes. Such processing may occur prior to input to the simulation component 120 (e.g., consider the processing component 116). As an example, the simulation component 120 may perform operations on input information based on one or more attributes specified by the attribute component 130. In an example embodiment, the simulation component 120 may construct one or more models of the geologic environment 150, which may be relied on to simulate behavior of the geologic environment 150 (e.g., responsive to one or more acts, whether natural or artificial). In the example of FIG. 1, the analysis/visualization component 142 may allow for interaction with a model or model-based results (e.g., simulation results, etc.). As an example, output from the simulation component 120 may be input to one or more other workflows, as indicated by a workflow component 144.

As an example, the simulation component 120 may include one or more features of a simulator such as the ECLIPSE® reservoir simulator (Schlumberger Limited, Houston Tex.), the INTERSECT® reservoir simulator (Schlumberger Limited, Houston Tex.), the VISAGE® geomechanics simulator (Schlumberger Limited, Houston Tex.), the PETROMOD® petroleum systems simulator (Schlumberger Limited, Houston Tex.), the PIPESIM® network simulator (Schlumberger Limited, Houston Tex.), etc. The ECLIPSE® simulator includes numerical solvers that may provide simulation results such as, for example, results that may predict dynamic behavior for one or more types of reservoirs, that may assist with one or more development schemes, which may assist with one or more production schemes, etc. The VISAGE® simulator includes finite element numerical solvers that may provide simulation results such as, for example, results as to compaction and subsidence of a geologic environment, well and completion integrity in a geologic environment, cap-rock and fault-seal integrity in a geologic environment, fracture behavior in a geologic environment, thermal recovery in a geologic environment, $CO_2$ disposal, etc. The PETROMOD® simulator includes finite element numerical solvers that may provide simulations results such as, for example, results as to structural evolution, temperature, and pressure history and as to effects of such factors on generation, migration, accumulation, and loss of oil and gas in a petroleum system through geologic time. Such a simulator can provide properties such as, for example, gas/oil ratios (GOR) and API gravities, which may be analyzed, understood, and predicted as to a geologic environment. The PIPESIM™ simulator includes solvers that may provide simulation results such as, for example, multiphase flow results (e.g., from a reservoir to a wellhead and beyond, etc.), flowline and surface facility performance, etc. The PIPESIM® simulator may be integrated, for example, with the AVOCET® production operations framework (Schlumberger Limited, Houston Tex.). As an example, a reservoir or reservoirs may be simulated with respect to one or more enhanced recovery techniques (e.g., consider a thermal process such as SAGD, etc.).

In an example embodiment, the management components 110 may include features of a commercially available framework such as the PETREL® seismic to simulation software framework (Schlumberger Limited, Houston, Tex.). The PETREL® framework provides components that allow for optimization of exploration and development operations. The PETREL® framework includes seismic to simulation software components that can output information for use in increasing reservoir performance, for example, by improving asset team productivity. Through use of such a framework, various professionals (e.g., geophysicists, geologists, and reservoir engineers) can develop collaborative workflows and integrate operations to streamline processes (e.g., with respect to one or more geologic environments, etc.). Such a framework may be considered an application (e.g., executable using one or more devices) and may be considered a data-driven application (e.g., where data is input for purposes of modeling, simulating, etc.).

In an example embodiment, various aspects of the management components 110 may include add-ons or plug-ins that operate according to specifications of a framework environment. For example, a commercially available framework environment marketed as the OCEAN® framework environment (Schlumberger Limited, Houston, Tex.) allows for integration of add-ons (or plug-ins) into a PETREL® framework workflow. The OCEAN® framework environment leverages .NET™ tools (Microsoft Corporation, Redmond, Wash.) and offers stable, user-friendly interfaces for efficient development. In an example embodiment, various components may be implemented as add-ons (or plug-ins) that conform to and operate according to specifications of a framework environment (e.g., according to application programming interface (API) specifications, etc.).

FIG. 1 also shows an example of a framework 170 that includes a model simulation layer 180 along with a framework services layer 190, a framework core layer 195 and a modules layer 175. The framework 170 may include the commercially available OCEAN® framework where the model simulation layer 180 is the commercially available PETREL® model-centric software package that hosts OCEAN® framework applications. In an example embodiment, the PETREL® software may be considered a data-driven application. The PETREL® software can include a framework for model building and visualization. Such a model may include one or more grids.

The model simulation layer 180 may provide domain objects 182, act as a data source 184, provide for rendering 186 and provide for various user interfaces 188. Rendering 186 may provide a graphical environment in which applications can display their data while the user interfaces 188 may provide a common look and feel for application user interface components.

In the example of FIG. 1, the domain objects 182 can include entity objects, property objects and optionally other objects. Entity objects may be used to geometrically represent wells, surfaces, reservoirs, etc., while property objects may be used to provide property values as well as data versions and display parameters. For example, an entity object may represent a well where a property object provides log information as well as version information and display information (e.g., to display the well as part of a model).

In the example of FIG. 1, data may be stored in one or more data sources (or data stores, generally physical data storage devices), which may be at the same or different physical sites and accessible via one or more networks. The model simulation layer 180 may be configured to model projects. As such, a particular project may be stored where stored project information may include inputs, models, results and cases. Thus, upon completion of a modeling session, a user may store a project. At a later time, the project can be accessed and restored using the model simulation layer 180, which can recreate instances of the relevant domain objects.

In the example of FIG. 1, the geologic environment 150 may include layers (e.g., stratification) that include a reservoir 151 and that may be intersected by a fault 153. As an example, the geologic environment 150 may be outfitted with any of a variety of sensors, detectors, actuators, etc. For example, equipment 152 may include communication circuitry to receive and to transmit information with respect to one or more networks 155. Such information may include information associated with downhole equipment 154, which may be equipment to acquire information, to assist with resource recovery, etc. Other equipment 156 may be located remote from a well site and include sensing, detecting, emitting or other circuitry. Such equipment may include storage and communication circuitry to store and to communicate data, instructions, etc. As an example, one or more satellites may be provided for purposes of communications, data acquisition, etc. For example, FIG. 1 shows a satellite in communication with the network 155 that may be configured for communications, noting that the satellite may additionally or alternatively include circuitry for imagery (e.g., spatial, spectral, temporal, radiometric, etc.).

FIG. 1 also shows the geologic environment 150 as optionally including equipment 157 and 158 associated with a well that includes a substantially horizontal portion that may intersect with one or more fractures 159. For example, consider a well in a shale formation that may include natural fractures, artificial fractures (e.g., hydraulic fractures) or a combination of natural and artificial fractures. As an example, a well may be drilled for a reservoir that is laterally extensive. In such an example, lateral variations in properties, stresses, etc. may exist where an assessment of such variations may assist with planning, operations, etc. to develop a laterally extensive reservoir (e.g., via fracturing, injecting, extracting, etc.). As an example, the equipment 157 and/or 158 may include components, a system, systems, etc. for fracturing, seismic sensing, analysis of seismic data, assessment of one or more fractures, etc.

As an example, the geologic environment 150 and/or another geologic environment can include various types of features. For example, a geologic environment can include one or more salt domes, magma intrusions, volcanic regions, geothermal regions, waste storage regions, etc. As an example, a framework may provide for modeling geothermal phenomena, mechanical phenomena, waste storage phenomena (e.g., radioactive or other waste), etc. As an example, a geologic environment can include rock that may be oriented horizontally, vertically, or at other types of orientations. As an example, a framework may provide for modeling a geologic environment with respect to structures, which may be completions or other types of structures.

As an example, in geothermal exploration, cylindrical magmatic plugs may be identified and characterized. A volcanic plug can be an igneous intrusion formed when magma crystallizes within a neck of a volcano. In such an example, subsequent weathering and erosion can remove some of the rock to leave cylindrical plugs that formed from magma that has cooled inside volcanic vents. As an example, consider Devil's Tower (Wyoming), which is a volcanic plug, formed of phonolite some 40 million years ago. Devil's Tower originated as a volcanic vent, but subsequent erosion of the surrounding rock has revealed the igneous rock that cooled and solidified underground. The phonolite that forms the Devil's Tower originates from continental crust and it includes crystals of aegirine and less silica than various other rhyolite magmas. As another example, consider Shiprock (New Mexico), which is a lampropohyre plug formed some 30 million years ago where lavas and pyroclastic deposits of the volcano have since disappeared and subsequent erosion of the underlying soft shales has steadily lowered the surface of the surrounding plains.

As an example, a geologic environment can include dikes and sills. As an example, a method can include identifying such features, for example, based at least in part on information acquired via one or more types of borehole tool sensors. As an example, a method can include identifying thinly bedded features that can disrupt the bedding such as veins, fractures, faults, dikes, sills, etc.

As mentioned, the system 100 may be used to perform one or more workflows. A workflow may be a process that includes a number of worksteps. A workstep may operate on data, for example, to create new data, to update existing data, etc. As an example, a may operate on one or more inputs and create one or more results, for example, based on one or more algorithms. As an example, a system may include a workflow editor for creation, editing, executing, etc. of a workflow. In such an example, the workflow editor may provide for selection of one or more pre-defined worksteps, one or more customized worksteps, etc. As an example, a workflow may be a workflow implementable in the PETREL® software, for example, that operates on seismic data, seismic attribute(s), etc. As an example, a workflow may be a process implementable in the OCEAN® framework. As an example, a workflow may include one or more worksteps that access a module such as a plug-in (e.g., external executable code, etc.).

FIG. 1 also shows one or more modules 198, which may operate in conjunction with the framework 170. For example, the one or more modules 198 may be implemented as one or more plug-in module, one or more external modules, etc. As an example, the one or more modules 198 may include one or more modules of the commercially available TECHLOG® framework (Schlumberger Limited, Houston, Tex.), which can provide wellbore-centric, cross-domain workflows based on a data management layer. The TECHLOG® framework includes features for petrophysics (core and log), geology, drilling, reservoir and production engineering, and geophysics.

Figure 2:
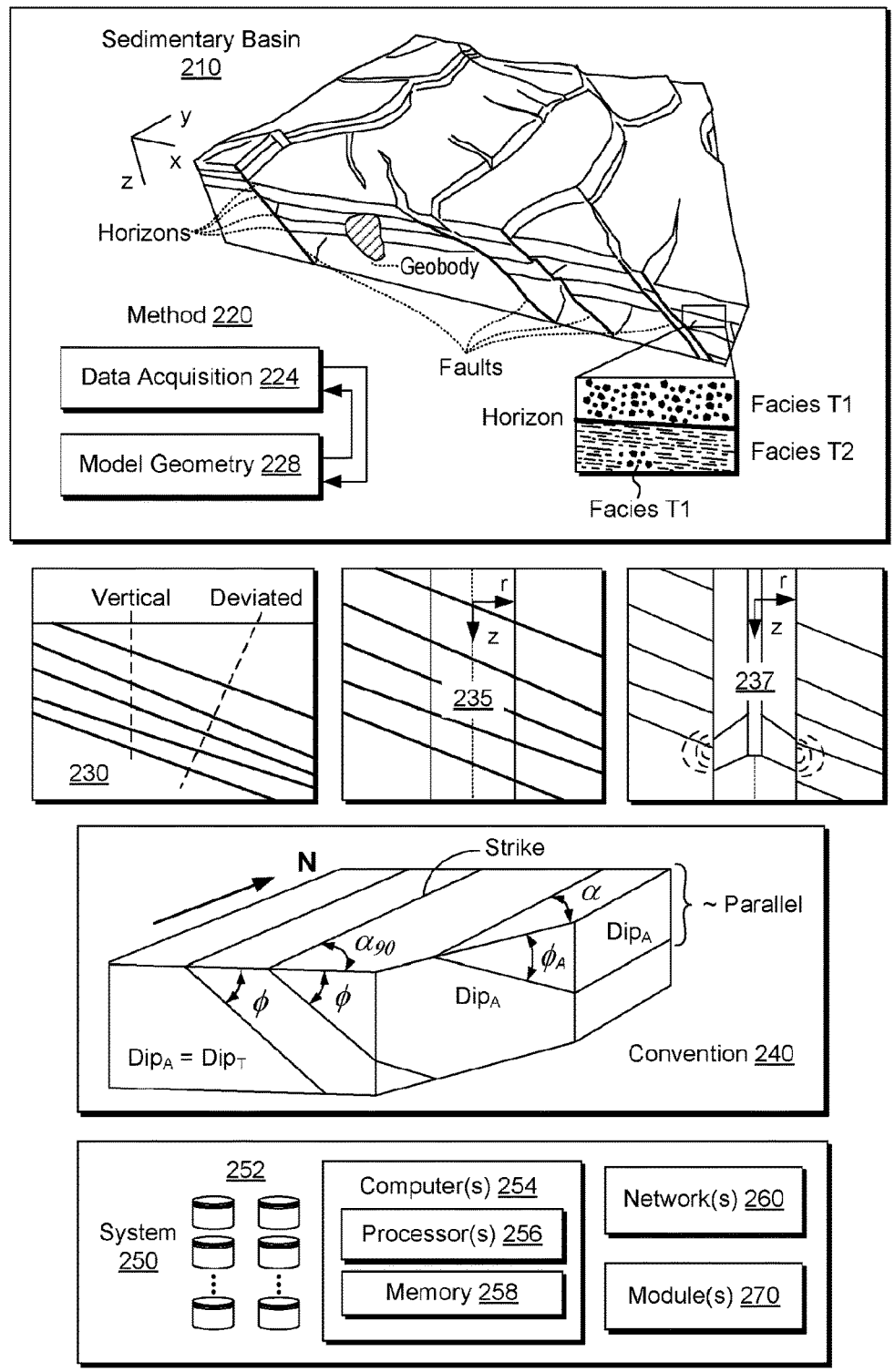
FIG. 2 illustrates examples of a basin, a convention and a system.

FIG. 2 shows an example of a sedimentary basin 210 (e.g., a geologic environment), an example of a method 220 for model building (e.g., for a simulator, etc.), an example of a formation 230, an example of a borehole 235 in a formation, an example of a convention 240 and an example of a system 250.

As an example, data acquisition, reservoir simulation, petroleum systems modeling, etc. may be applied to characterize various types of subsurface environments, including environments such as those of FIG. 1.

In FIG. 2, the sedimentary basin 210, which is a geologic environment, includes horizons, faults, one or more geobodies and facies formed over some period of geologic time. These features are distributed in two or three dimensions in space, for example, with respect to a Cartesian coordinate system (e.g., x, y and z) or other coordinate system (e.g., cylindrical, spherical, etc.). As shown, the model building method 220 includes a data acquisition block 224 and a model geometry block 228. Some data may be involved in building an initial model and, thereafter, the model may optionally be updated in response to model output, changes in time, physical phenomena, additional data, etc. As an example, data for modeling may include one or more of the following: depth or thickness maps and fault geometries and timing from seismic, remote-sensing, electromagnetic, gravity, outcrop and well log data. Furthermore, data may include depth and thickness maps stemming from facies variations (e.g., due to seismic unconformities) assumed to following geological events ("iso" times) and data may include lateral facies variations (e.g., due to lateral variation in sedimentation characteristics).

To proceed to modeling of geological processes, data may be provided, for example, data such as geochemical data (e.g., temperature, kerogen type, organic richness, etc.), timing data (e.g., from paleontology, radiometric dating, magnetic reversals, rock and fluid properties, etc.) and boundary condition data (e.g., heat-flow history, surface temperature, paleowater depth, etc.).

In basin and petroleum systems modeling, quantities such as temperature, pressure and porosity distributions within the sediments may be modeled, for example, by solving partial differential equations (PDEs) using one or more numerical techniques. Modeling may also model geometry with respect to time, for example, to account for changes stemming from geological events (e.g., deposition of material, erosion of material, shifting of material, etc.).

The aforementioned commercially available modeling framework marketed as the PETROMOD® framework (Schlumberger Limited, Houston, Tex.) includes features for input of various types of information (e.g., seismic, well, geological, etc.) to model evolution of a sedimentary basin. The PETROMOD® framework provides for petroleum systems modeling via input of various data such as seismic data, well data and other geological data, for example, to model evolution of a sedimentary basin. The PETROMOD® framework may predict if, and how, a reservoir has been charged with hydrocarbons, including, for example, the source and timing of hydrocarbon generation, migration routes, quantities, pore pressure and hydrocarbon type in the subsurface or at surface conditions. In combination with a framework such as the PETREL® framework, workflows may be constructed to provide basin-to-prospect scale exploration solutions. Data exchange between frameworks can facilitate construction of models, analysis of data (e.g., PETROMOD® framework data analyzed using PETREL® framework capabilities), and coupling of workflows. As an example, the TECHLOG® framework may be implemented in a workflow, for example, using one or more features for petrophysics (core and log), geology, drilling, reservoir and production engineering, and geophysics.

As shown in FIG. 2, the formation 230 includes a horizontal surface and various subsurface layers. As an example, a borehole may be vertical. As another example, a borehole may be deviated. In the example of FIG. 2, the borehole 235 may be considered a vertical borehole, for example, where the z-axis extends downwardly normal to the horizontal surface of the formation 230. As an example, a tool 237 may be positioned in a borehole, for example, to acquire information. As mentioned, a borehole tool may be configured to acquire electrical borehole images. As an example, the fullbore Formation MicroImager (FMI) tool (Schlumberger Limited, Houston, Tex.) can acquire borehole image data. A data acquisition sequence for such a tool can include running the tool into a borehole with acquisition pads closed, opening and pressing the pads against a wall of the borehole, delivering electrical current into the material defining the borehole while translating the tool in the borehole, and sensing current remotely, which is altered by interactions with the material.

As an example, data can include geochemical data. For example, consider data acquired using X-ray fluorescence (XRF) technology, Fourier transform infrared spectroscopy (FTIR) technology and/or wireline geochemical technology.

XRF technology involves emission of characteristic "secondary" (or fluorescent) X-rays from a material that has been excited by bombardment with high-energy X-rays or gamma rays. XRF technology may be implemented for elemental analysis and chemical analysis, for example, as to research in geochemistry. As an example, in core analysis, XRF technology may be implemented to help determine mineral content. For example, elemental volumes may be inverted to mineral volumes by assuming certain standard formulae for mineral composition.

FTIR technology can involve analysis of an infrared spectrum of absorption, emission, photoconductivity or Raman scattering of a solid, liquid or gas. As an example, FTIR may be applied as a technique for quantitative mineralogical analysis of a sample of rock by measuring the effect of midrange infrared radiation transmitted through the sample. In such an example, the radiation excites vibrations in the chemical bonds within the mineral molecules at particular frequencies characteristic of each bond. The transmitted radiation may be compared with spectral standards for a variety of minerals, for example, to determine abundance of one or more minerals in the sample. As to sample preparation, consider, as an example, grinding a core plug to provide a representative sample that may be dispersed in a potassium bromide matrix and then subject to measurement and analysis.

As an example, data may be acquired using X-ray diffraction (XRD or X-ray crystallography). X-ray crystallography equipment may be used to acquire data that may be analyzed for identifying atomic and molecular structure of a crystal, in which the crystalline atoms cause a beam of incident X-rays to diffract (e.g., into various directions). By measuring the angles and intensities of diffracted beams, a multi-dimensional image of density of electrons within the crystal may be generated. From electron density, for example, mean positions of atoms in a crystal may be determined, as well as, for example, one or more of chemical bonds, disorder, etc.

As an example, one or more probes may be deployed in a bore via a wireline or wirelines. As an example, a probe may emit energy and receive energy where such energy may be analyzed to help determine mineral composition of rock surrounding a bore. As an example, nuclear magnetic resonance (NMR or MR) may be implemented (e.g., via a wireline, downhole NMR probe, etc.), for example, to acquire data as to nuclear magnetic properties of elements in a formation (e.g., hydrogen, carbon, phosphorous, etc.).

As an example, lithology scanning technology may be employed to acquire and analyze data. For example, consider the commercially available LITHO SCANNER™ technology marketed by Schlumberger Limited (Houston, Tex.). As an example, a LITHO SCANNER™ tool may be a gamma ray spectroscopy tool. Such a tool is an example a lithology scanner tool (e.g., or lithology scanning tool). As an example, a workflow may include emission of neutrons by a pulsed neutron generator (PNG) of a tool to induce emission of gamma rays from a formation via interactions such as inelastic scattering interactions and thermal neutron capture interactions, which can produce gamma rays with a specific set of characteristic energies. In turn, gamma rays may be detected by a $LaBr_3$:Ce scintillator coupled to a high-temperature spectroscopy photomultiplier, producing signals that can be integrated, digitized, and processed by a high-performance pulse-height analyzer. Such an analyzer may determine, for example, pulse height (proportional to energy) of individually detected gamma rays and accumulate pulse-height histograms (spectra) that tally counts versus pulse height. Spectra may be acquired, for example, during and after each neutron burst, which helps to enable separation of inelastic and capture gamma rays. As an example, an individual spectrum may be decomposed into a linear combination of standard spectra from individual elements, which can involve correction for one or more environmental and/or electronic factors. As an example, coefficients of linear combination of standard spectra may be converted to elemental weight fractions, for example, via a modified geochemical oxides closure model, an inversion approach, etc. As to interpretation, various approaches may be implemented to generate mineralogy and lithologic fractions from the elemental concentration logs. As an example, a sequential SpectroLith processing approach may be used, which is based on the derivation of empirical relationships between elemental concentrations and mineral concentrations. As another example, an iterative inversion technique may be implemented (e.g., consider the TECHLOG® QUANTI™ multicomponent inversion ELAN module).

As an example, a method may include acquiring data (e.g., and/or receiving data) as measured via one or more techniques. Such techniques may include a micro-resistivity technique, a density and photoelectric factor or index technique, an image calibration technique, a dielectric and conductivity dispersion technique, a neutron porosity technique, an ultrasound technique, etc. As an example, a method may include acquiring data from dielectric measurement equipment and data from another type of measurement equipment and analyzing the data to detect at least one igneous deposit. In such an example, the data from the other type of measurement may be cross-referenced spatially with the data from the dielectric measurement equipment and analyzed to identify one or more igneous deposits (e.g., detect one or more igneous deposits, characterize one or more igneous deposits, etc.).

As an example, a workflow may utilize geochemical data, and optionally other data, for one or more processes (e.g., stratigraphic modeling, basin modeling, completion designs, drilling, production, injection, etc.). As an example, lithology scanner tool data may be used in a workflow or workflows that implement one or more frameworks (e.g., PETREL®, TECHLOG®, PETROMOD®, etc.).

As an example, a borehole may be vertical, deviate and/or horizontal. As an example, a tool may be positioned to acquire information in a horizontal portion of a borehole. Analysis of such information may reveal vugs, dissolution planes (e.g., dissolution along bedding planes), stress-related features, dip events, etc. As an example, a tool may acquire information that may help to characterize a fractured reservoir, optionally where fractures may be natural and/or artificial (e.g., hydraulic fractures). Such information may assist with completions, stimulation treatment, etc. As an example, information acquired by a tool may be analyzed using a framework such as the aforementioned TECHLOG® framework (Schlumberger Limited, Houston, Tex.).

As to the convention 240 for dip, as shown, the three dimensional orientation of a plane can be defined by its dip and strike. Dip is the angle of slope of a plane from a horizontal plane (e.g., an imaginary plane) measured in a vertical plane in a specific direction. Dip may be defined by magnitude (e.g., also known as angle or amount) and azimuth (e.g., also known as direction). As shown in the convention 240 of FIG. 2, various angles φ indicate angle of slope downwards, for example, from an imaginary horizontal plane (e.g., flat upper surface); whereas, dip refers to the direction towards which a dipping plane slopes (e.g., which may be given with respect to degrees, compass directions, etc.). Another feature shown in the convention of FIG. 2 is strike, which is the orientation of the line created by the intersection of a dipping plane and a horizontal plane (e.g., consider the flat upper surface as being an imaginary horizontal plane).

Some additional terms related to dip and strike may apply to an analysis, for example, depending on circumstances, orientation of collected data, etc. One term is "true dip" (see, e.g., $Dip_T$ in the convention 240 of FIG. 2). True dip is the dip of a plane measured directly perpendicular to strike (see, e.g., line directed northwardly and labeled "strike" and angle $\alpha_{90}$) and also the maximum possible value of dip magnitude. Another term is "apparent dip" (see, e.g., $Dip_A$ in the convention 240 of FIG. 2). Apparent dip may be the dip of a plane as measured in any other direction except in the direction of true dip (see, e.g., $\phi_A$ as $Dip_A$ for angle α); however, it is possible that the apparent dip is equal to the true dip (see, e.g., φ as $Dip_A$=$Dip_T$ for angle $\alpha_{90}$ with respect to the strike). In other words, where the term apparent dip is used (e.g., in a method, analysis, algorithm, etc.), for a particular dipping plane, a value for "apparent dip" may be equivalent to the true dip of that particular dipping plane.

As shown in the convention 240 of FIG. 2, the dip of a plane as seen in a cross-section perpendicular to the strike is true dip (see, e.g., the surface with φ as $Dip_A$=$Dip_T$ for angle $\alpha_{90}$ with respect to the strike). As indicated, dip observed in a cross-section in any other direction is apparent dip (see, e.g., surfaces labeled $Dip_A$). Further, as shown in the convention 240 of FIG. 2, apparent dip may be approximately 0 degrees (e.g., parallel to a horizontal surface where an edge of a cutting plane runs along a strike direction).

In terms of observing dip in wellbores, true dip is observed in wells drilled vertically. In wells drilled in any other orientation (or deviation), the dips observed are apparent dips (e.g., which are referred to by some as relative dips). In order to determine true dip values for planes observed in such boreholes, as an example, a vector computation (e.g., based on the borehole deviation) may be applied to one or more apparent dip values.

As mentioned, another term that finds use in sedimentological interpretations from borehole images is "relative dip" (e.g., $Dip_R$). A value of true dip measured from borehole images in rocks deposited in very calm environments may be subtracted (e.g., using vector-subtraction) from dips in a sand body. In such an example, the resulting dips are called relative dips and may find use in interpreting sand body orientation.

A convention such as the convention 240 may be used with respect to an analysis, an interpretation, an attribute, etc. (see, e.g., various blocks of the system 100 of FIG. 1). As an example, various types of features may be described, in part, by dip (e.g., sedimentary bedding, faults and fractures, cuestas, igneous dikes and sills, metamorphic foliation, etc.). As an example, dip may change spatially as a layer approaches a geobody. For example, consider a salt body that may rise due to various forces (e.g., buoyancy, etc.). In such an example, dip may trend upward as a salt body moves upward.

Seismic interpretation may aim to identify and/or classify one or more subsurface boundaries based at least in part on one or more dip parameters (e.g., angle or magnitude, azimuth, etc.). As an example, various types of features (e.g., sedimentary bedding, faults and fractures, cuestas, igneous dikes and sills, metamorphic foliation, etc.) may be described at least in part by angle, at least in part by azimuth, etc.

As an example, equations may be provided for petroleum expulsion and migration, which may be modeled and simulated, for example, with respect to a period of time. Petroleum migration from a source material (e.g., primary migration or expulsion) may include use of a saturation model where migration-saturation values control expulsion. Determinations as to secondary migration of petroleum (e.g., oil or gas), may include using hydrodynamic potential of fluid and accounting for driving forces that promote fluid flow. Such forces can include buoyancy gradient, pore pressure gradient, and capillary pressure gradient.

While petroleum expulsion and migration are mentioned, one or more other types of phenomena may be modeled. For example, a method can include modeling of one or more types of processes in geothermal and/or waste storage environments. For example, in such environment, hydrology may be modeled based at least in part on information acquired via one or more types of borehole tool sensors.

As shown in FIG. 2, the system 250 includes one or more information storage devices 252, one or more computers 254, one or more networks 260 and one or more modules 270. As to the one or more computers 254, each computer may include one or more processors (e.g., or processing cores) 256 and memory 258 for storing instructions (e.g., modules), for example, executable by at least one of the one or more processors. As an example, a computer may include one or more network interfaces (e.g., wired or wireless), one or more graphics cards, a display interface (e.g., wired or wireless), etc. As an example, imagery such as surface imagery (e.g., satellite, geological, geophysical, etc.) may be stored, processed, communicated, etc. As an example, data may include SAR data, GPS data, etc. and may be stored, for example, in one or more of the storage devices 252.

As an example, the one or more modules 270 may include instructions (e.g., stored in memory) executable by one or more processors to instruct the system 250 to perform various actions. As an example, the system 250 may be configured such that the one or more modules 270 provide for establishing the framework 170 of FIG. 1 or a portion thereof. As an example, one or more methods, techniques, etc. may be performed using one or more modules, which may be, for example, one or more of the one or more modules 270 of FIG. 2.

As mentioned, seismic data may be acquired and analyzed to understand better subsurface structure of a geologic environment. Reflection seismology finds use in geophysics, for example, to estimate properties of subsurface formations. As an example, reflection seismology may provide seismic data representing waves of elastic energy (e.g., as transmitted by P-waves and S-waves, in a frequency range of approximately 1 Hz to approximately 100 Hz or optionally less than 1 Hz and/or optionally more than 100 Hz). Seismic data may be processed and interpreted, for example, to understand better composition, fluid content, extent and geometry of subsurface rocks.

As an example, a method may include receiving detrital information and/or diagenetic information (e.g., optionally acquiring such information using one or more tools). For example, detrital information may pertain to particles of rock derived from the mechanical breakdown of preexisting rocks by weathering and erosion. As an example, detrital fragments may be transported to recombine and, through the process of lithification, become sedimentary rocks. As to diagenetic information, it may pertain to physical, chemical and/or biological alteration of sediments into sedimentary rock, for example, at relatively low temperatures and pressures that can result in changes to rock mineralogy and texture. For example, after deposition, sediments may be compacted as they are buried beneath successive layers of sediment and cemented by minerals that precipitate from solution. Grains of sediment, rock fragments and fossils may be replaced by other minerals during diagenesis. Porosity may decrease during one or more diagenetic processes; or, for example, increase via dissolution of minerals and dolomitization. Hydrocarbon generation may begin during diagenesis.

Diagenetic phenomena may occur as an initial stage of alteration of sediments and maturation of kerogen (e.g., at temperatures less than about 50 degrees C.). The type or types of hydrocarbon generated can depend on the type or types of organic matter in kerogen, the amount of time that has past, the ambient temperature and pressure, etc. Microbial activity can contributor to breakdown of organic matter and result in production of biogenic gas. Longer exposure to higher temperatures during diagenesis, catagenesis, and metagenesis can results in transformation of kerogen into liquid hydrocarbons and hydrocarbon gases.

As an example, a method may include calculating a detrital index and/or a diagenetic index. Such a method may aim to determine a proportion of depositional mineralogy versus diagenetic mineralogy. For example, consider the following equations for an example of a detrital index (Eqn. (1)) and an example of a diagenetic index (Eqn. (2)):

$$\text{Detrital Index} = (\text{Biotite} + \text{Muscovite} + \text{Orthoclase})/(\text{Biotite} + \text{Muscovite} + \text{Orthoclase} + \text{Quartz}) \qquad \text{Eqn. (1)}$$

$$\text{Diagenetic Index} = (\text{Dolomite} + \text{Pyrite} + \text{Anhydrite} + \text{Evaporites} + \text{Ankerite})/(\text{Dolomite} + \text{Pyrite} + \text{Anhydrite} + \text{Evaporites} + \text{Ankerite} + \text{Calcite}) \qquad \text{Eqn. (2)}$$

In Eqns. (1) and (2), composition values may be given as percentages. For example, a sample may be analyzed with respect to a percentage of biotite, muscovite, orthoclase, quartz, dolomite, pyrite, anhydrite, evaporates, ankerite and calcite; noting that various minerals may be provided in an equation or equations as examples. For example, one or more other minerals may be used to form equations where normalization may be with respect to quartz for a detrital index equation and for calcite with respect to a diagenetic index equation. As an example, an index may be inverted, for example, consider inverting one or both of Eqns. (1) and (2). In such an example, quartz and calcite may still act to "weight" or "normalize" the index values calculated via such equations. As an example, an index or indexes may be used to characterize a portion of a geologic environment.

As an example, composition values may be mineral-based and/or chemical-based. For example, where several minerals are of interest, an index may be formulated via minerals and/or may be formulated via chemical elements, chemical groups, etc. As an example, an index may optionally be formulated without a "normalization" value or values. For example, a trend may be determined for a region of rock via comparing index values that may include a numerator without a denominator as in the Eqns. (1) and (2), above.

Biotite is a phyllosilicate mineral within the mica group, with the approximate chemical formula $K(Mg,Fe)_3AlSi_3O_{10}(F,OH)_2$. Biotite may found in a wide variety of igneous and metamorphic rocks. For instance, biotite occurs in the lava of Mount Vesuvius and in the Monzoni intrusive complex of the western Dolomites. Biotite may be found as a constituent of metamorphic schists and it may form in suitable compositions over a wide range of pressure and temperature. A large single crystal of biotite may be in the form of 7 m$^2$ sheets (Iveland, Norway). Presence of biotite may be used, at least in part, to constrain ages of rocks (e.g., via potassium-argon dating, argon-argon dating, etc.). Argon may escape from a biotite crystal structure at high temperatures and partitioning of iron and magnesium between biotite and garnet may be sensitive to temperature.

Muscovite (e.g., common mica, isinglass, or potash mica) is a phyllosilicate mineral of aluminium and potassium with formula $KAl_2(AlSi_3O_{10})(F,OH)_2$ or $(KF)_2(Al_2O_3)_3(SiO_2)_6(H_2O)$.

Orthoclase (endmember formula $KAlSi_3O_8$) is a tectosilicate mineral tha can form igneous rock. The name is derived from the Greek for "straight fracture," because its two cleavage planes tend to be at right angles to each other. Alternative names include potassium feldspar and K-feldspar. Orthoclase can be found as a constituent of granite and other felsic igneous rocks and may forms large crystals and masses in pegmatite. As an example, slowly cooling within the earth, sodium-rich albite lamellae may form by exsolution, enriching remaining orthoclase with potassium. The resulting intergrowth of the two feldspars is called perthite.

Quartz is an abundant mineral in the Earth's continental crust, second after feldspar. Quartz can be made of a continuous framework of $SiO_4$ silicon-oxygen tetrahedra, with individual oxygen atoms being shared between two tetrahedra (e.g., $SiO_2$).

Dolomite is an anhydrous carbonate mineral composed of calcium magnesium carbonate, for example, consider $CaMg(CO_3)_2$. The term dolomite may refer to sedimentary carbonate rock, which is composed predominantly of mineral dolomite (e.g., dolostone). Dolomite may form under anaerobic conditions, for example, in supersaturated saline lagoons (e.g., Lagoa Vermelha and Brejo do Espinho, Brazil). Dolomite can develop in the presence of sulfate-reducing bacteria (e.g. *Desulfovibrio brasiliensis*).

Pyrite (iron sulfide, $FeS_2$) may be found associated with other sulfides or oxides in quartz veins, sedimentary rock, and metamorphic rock, as well as in coal beds and as a replacement mineral in fossils. Iron pyrite is unstable in the natural environment. Iron pyrite exposed to air and water decomposes into iron oxides and sulfate, a process that may be hastened by action of Acidithiobacillus bacteria (e.g., which can oxidize the pyrite to produce ferrous iron and sulfate).

Anhydrite is a mineral, anhydrous calcium sulfate, $CaSO_4$. Anhydrite may be found in evaporite deposits with gypsum. From an aqueous solution calcium sulfate may be deposited as crystals of gypsum and, when the solution contains an excess of sodium or potassium chloride, anhydrite may be deposited if temperature is above 40 degrees C. Anhydrite may be found in salt basins.

Evaporite refers to water-soluble mineral sediments that result from concentration and crystallization by evaporation from an aqueous solution. Evaporite can include marine (e.g., ocean deposits) and non-marine (e.g., found in standing bodies of water such as lakes). Evaporites may be considered sedimentary rocks.

Ankerite is a calcium, iron, magnesium, manganese carbonate mineral of the group of rhombohedral carbonates with formula: $Ca(Fe,Mg,Mn)(CO_3)_2$. In composition it is closely related to dolomite, but differs, having magnesium replaced by varying amounts of iron(II) and manganese. Ankerite may form series with dolomite and kutnohorite. In sediments, ankerite can occurs as authigenic, diagenetic minerals and as a product of hydrothermal deposition. Ankerite is a mineral of the dolomite-siderite series.

Calcite is a carbonate mineral and a most stable polymorph of calcium carbonate ($CaCO_3$); compared to minerals aragonite and vaterite. Aragonite can change to calcite, for example, at temperatures in a range of about 380 to about 470 degrees C.; vaterite is less stable. Calcite tends to dissolve upon exposure to acid. Calcite may be dissolved by groundwater or precipitated by groundwater, depending on several factors including the water temperature, pH, and dissolved ion concentrations. Although calcite is fairly insoluble in cold water, acidity can cause dissolution of calcite and release of carbon dioxide gas. Ambient carbon dioxide, due to its acidity, has a slight solubilizing effect on calcite. Calcite can exhibit retrograde solubility in which it becomes less soluble in water as temperature increases. When conditions are right for precipitation, calcite forms mineral coatings that can cement existing rock grains together or, for example, fill fractures. When conditions are right for dissolution, removal of calcite can increase porosity and permeability of rock (e.g., consider dissolution of calcium carbonate-rich rocks that can lead to expansion and collapse of cave systems, resulting in various forms of karst topography).

As an example, a carbonate may be defined as a salt of carbonic acid, which may be characterized by the presence of the carbonate ion (e.g., $CO_3^{2-}$). As an example, XRD and FTIR may be used to assess carbonate minerals. As an example, Mössbauer spectroscopy may be implemented to assess one or more minerals (e.g., as to state of iron, etc.), optionally in conjunction with one or more of XRD and FTIR. As an example, information as to carbonates (e.g., calcite, ferroan calcite, dolomite, ferroan dolomite, ankerite, siderite, etc.) may be plotted on a spectrum with respect to $XY(CO_3)_2$. As XRD and FTIR can measure concentrations of Mn, Fe, Mg in one or more carbonate minerals (e.g., based on different phenomena), use of XRD and/or FTIR information can allow for one or more XRD indexes, one or more FTIR indexes and/or one or more mixed XRD and FTIR indexes. As an example, a method may include comparing one or more FTIR index values to one or more XRD index values. Such a method may, for example, allow for identification of trends in diagenesis, classification of early and/or late diagenesis, etc.

As an example, FTIR information (e.g., FTIR data, analyzed data, etc.) may be utilized, for example, to characterize a formation that includes carbonate based at least in part on iron concentrations (e.g., different amounts of iron within calcite, etc.). As an example, FTIR information may be used to quantitatively and/or to quantitatively asses XRD information. As an example, FTIR information as to iron may aid in classifying one or more portions of a formation, for example, as to diagenesis (e.g., early diagenesis, late diagenesis, etc.). In such an example, such information may be linked to one or more other characteristics of a formation (e.g., porosity, permeability, etc.). As an example, a method can include receiving XRD data and FTIR data and assessing diagenesis of at least a portion of a formation based at least in part on such data (e.g., pick-up different generations of diagenesis, etc.). Such a method may include calculating one or more indexes (e.g., optionally based on individual and/or combined data sets).

As an example, a method may include receiving lithology scanner data and XRD data and calculating one or more indexes based on such data (e.g., data sets). Such indexes may be plotted with respect to a spatial dimension (e.g., depth) and, for example, compared to each other. As an example, XRD data may see muscovite and illite together while lithology scanner may distinguish muscovite and illite. In such an example, a trend derived from XRD data may differ from a trend derived from lithology scanner data. Such a difference may help to assess mineralogy of at least a portion of a formation.

As an example, a method may include receiving FTIR data (e.g., "raw" mineralogical data), lithology scanner data (e.g., calculated data) and XRD data (e.g., "raw" mineralogical data) and, for example, calculating indexes based at least in part on such data. For example, a method may include calculating values of an FTIR-based index, values of a lithology scanner-based index and values of an XRD-based index. In such an example, the values may be compared and may help to assess mineralogy of at least a portion of a formation.

As an example, a method may include characterizing material via chemical constituents as to chemical composition. As an example, a chemical fingerprint may be generated and compared to one or more known chemical fingerprints (e.g., a single fingerprint, a mixture of fingerprints, etc.). As an example, a method may include receiving trace element data (e.g., XRF data, etc.). Such a method may include modeling of a sample or samples based at least in part on the trace element data (e.g., as to sample mineralogy). As an example, a method may include building a solid solution model of carbonates. In such an example, a model may be based at least in part on data (e.g., XRF data, etc.). As an example, a model may be a diagenetic model, for example, that highlights chemical elements. In such an example, the chemical elements may correspond to one or more minerals (e.g., chemical make-up of one or more minerals). As an example, a model may be a detrital model, which may be based at least in part on chemical elements. In such an example, the chemical elements may correspond to one or more minerals (e.g., chemical make-up of one or more minerals).

As an example, a workflow may utilize mineralogy from one or more sources (e.g., lithology scanner, XRD, FTIR, etc.) to help distinguish rock history. Rock history can be used, for example, for predictive modeling and deconvolving rock mineralogy into deposition and diagenetic components. As an example, mineralogy data may be harnessed to improve spatial distribution of properties, for example, to aid in building, refining, etc. reservoir models, completion models, etc.

As an example, a method may include classifying rock based on trace element data (e.g., data from one or more of XRF, ICP-MS, organic geochemistry, mineralogy from XRD, etc.). Such a method may model rock as it exists today, without distinguishing the history of the rock. As an example, rock may be considered a composite of its depositional components, for example, as may be used for stratigraphy, and its diagenetic components, for example, as may be used for completion engineering. As an example, to help understand rock history, a method may include distinguishing between depositional and diagenetic components of rock. Such a method may aid in predictive modeling, for example, to improve reservoir and completion models.

As an example, a method can include analyzing rock samples for deposition and diagenesis. Such a method may include accessing one or more sidewall cores and one or more whole cores. Such a method can have associated acquisition and drilling costs as well as storage costs (e.g., for maintenance of cores). As an example, a workflow may reduce such costs. For example, a workflow may aim to separate depositional and diagenetic mineralogy without or with limited petrological analysis.

As an example, a workflow can utilize geochemical data from one or more sources to help determine the proportion of depositional mineralogy versus diagenetic mineralogy. As an example, mineralogy can be separated by a series of indices into component parts (e.g., detrital) and, for example, processed via one or more frameworks, for example, for modeling stratigraphy, completion engineering.

As an example, a geologic environment can include igneous deposits. As an example, igneous deposits may be volcanic deposits stemming from phenomena such as, for example, lahars, pyroclastic flows, and underwater eruptions. As an example, an igneous deposit may include bentonite, an absorbent aluminum phyllosilicate. As an example, an igneous deposit may exist as an ash bed. As an example, a devitrified (e.g., weathered volcanic glass) ash-fall beds can include bentonite. As an example, an igneous deposit may be characterized along a spectrum from an original deposit to a highly altered volcanic deposit (e.g., depending on conditions). As an example, an igneous deposit may be characterized as a fall, a flow, etc.

As an example, an igneous deposit may exist in an unconventional basin or play. For example, interbedded weathered ash beds may exist in unconventional plays. The term "unconventional" may refer to a resource or resources such as, for example, oil and natural gas. A geologic environment may be characterized, for example, as to one or more of porosity, permeability, fluid trapping mechanism, or other characteristics, which may differ from so-called "conventional" sandstone and carbonate reservoirs. Coalbed methane, gas hydrates, shale gas, shale oil, fractured reservoirs, and tight gas sands may be considered to be unconventional resources (e.g., in an "unconventional" environment, play, etc.).

As an example, an igneous deposit in a geologic environment may have an effect on initiation and retention of fracture conductivity through time, which may negatively impact performance of well drilled into that geologic environment. As an example, a method can include detecting (e.g., and optionally quantifying) one or more igneous deposits in a geologic environment. Such a method may help during a workflow that includes selecting one or more targets, for example, for lateral placement. Such a method may, for example, assist with well design and completions to mitigate production problems where interaction with one or more igneous deposits may be practically unavoidable.

As an example, ash can be volcanic ash produced by one or more volcanic eruptions. A volcanic eruption can produce material such as tephra that is propelled into the air. Where pieces of ejecta are small, the material may be classified as volcanic ash, for example, consider particles less than 2 mm in diameter, sand-sized or smaller. Such particles can be slaggy pieces of magma and rock that have been tossed into the air by outbursts of steam and other gases.

As an example, a method can include detecting one or more igneous deposits in a geologic environment (e.g., weathered ash beds, etc.). Such a method may include receiving information from one or more types of equipment. For example, consider information acquired via one or more of high resolution dielectric dispersion measurement equipment, micro-resistivity measurement equipment, density and photoelectric factor measurement equipment, borehole image log measurement equipment, etc.

As an example, a method can include receiving low resolution geochemistry and neutron porosity logs that may be then used to refine an interpretation of an igneous deposit or deposits. As an example, petrological analysis may be performed, for example, on one or more samples (e.g., core, cutting, etc.). Such an analysis may provide trends in petrology, etc., which may be part of a workflow. Petrological information may be combined with other information, for example, for validation, etc.

As an example, a method may include receiving dielectric logs at different frequencies and array spacings with measured micro-resistivity data (e.g., one or more curves from micro spherically focused logging (Micro-SFL or MSFL) tool images). In such an example, the method may include detecting weathered ash and, for example, computing the occurrence and thicknesses variations along a borehole at one or more selected resolutions.

As an example, an igneous deposit may be detected using spectral gamma ray logs. Natural spectral gamma ray equipment may measure concentrations of potassium (K), uranium (U) and thorium (Th) along a borehole. Concentration values from such a technique can allow for interpretations of different depositional settings (e.g., reducing versus oxidizing conditions, etc.). As an example, high concentrations of thorium may be associated with heavy minerals and volcanic ash beds. High concentrations of particular elements resistant to diagenesis like titanium (Ti), niobium (Nb), zirconium (Zr), and yttrium (Y), together with Th, as mentioned, can be indicators of weathered volcanic ash beds. The resolution of gamma ray-based equipment may be about 36 cm. As such a resolution, gamma ray-based detection may fail to detect small interbedded ash beds. Such igneous deposits may be of interest as to exploration, development, production, etc. of a resource or resources from a geologic environment. For example, an igneous deposit may cause disruption during a completion phase of a geologic environment.

As an example, a neutron-based technique may compare enrichments of Ti or silica (Si) to aluminum (Al), which may be attributed to terrigeneous input or, for example, associated with weathered volcanic ash. To determine whether a trace element is volcanic or detrital, a method may employ various elemental ratios. A neutron-based technique may have a vertical resolution of about 36 cm. As mentioned, an igneous deposit may impact a completion. For example, an ash bed with a thickness of about 3 cm or less may impact completion. As such igneous deposit thickness is less than the aforementioned equipment resolutions (e.g., gamma ray and neutron), such techniques may fail to detect one or more igneous deposits.

Figure 3:
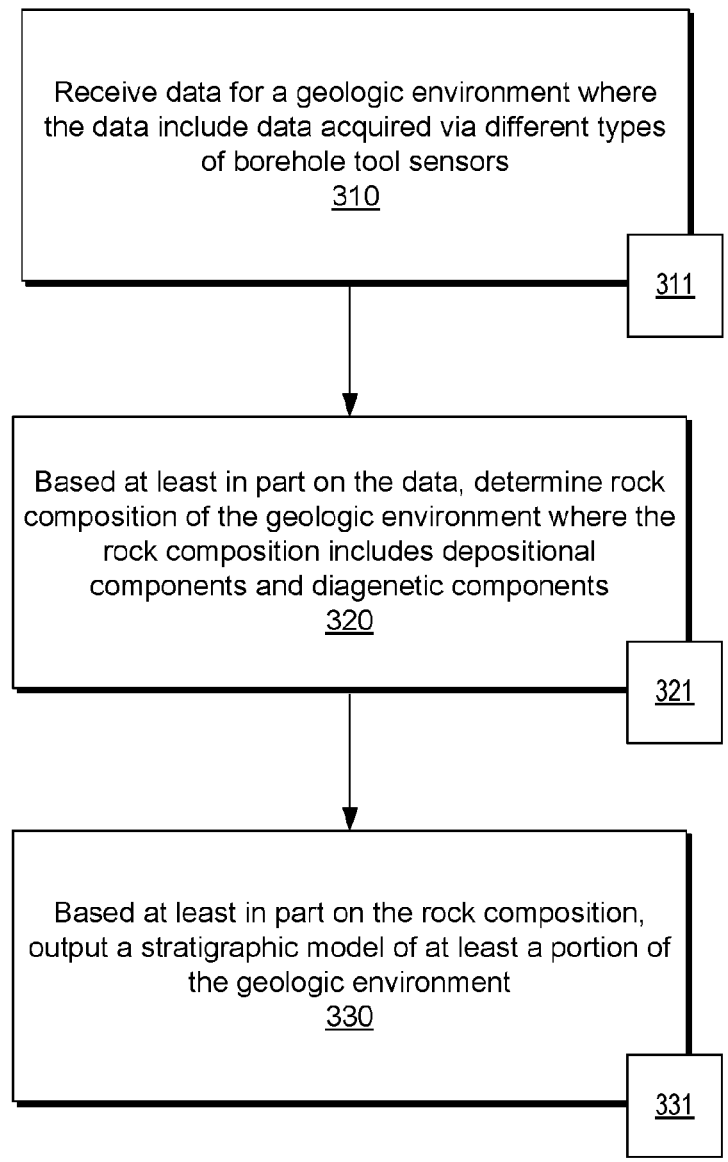
FIG. 3 illustrates an example of a method.

FIG. 3 shows an example of a method 300 that includes a reception block 310 for receiving data for a geologic environment where the data include data acquired via different types of borehole tool sensors; a determination block 320 for, based at least in part on the data, determining rock composition of the geologic environment where the rock composition includes depositional components and diagenetic components; and an output block 330 for, based at least in part on the rock composition, outputting a stratigraphic model of at least a portion of the geologic environment.

As an example, determining rock composition can include determining detrital mineral composition values associated with at least one of a plurality of depositional components and calculating a detrital index value based at least in part on the detrital mineral composition values. Such an example can include, based at least in part on the detrital index value, attributing a portion of a stratigraphic model to a particular geological source.

As an example, determining rock composition can include determining diagenetic mineral composition values associated with at least one of a plurality of diagenetic components and calculating a diagenetic index value based at least in part on the diagenetic mineral composition values. Such an example can include, based at least in part on the diagenetic index value, attributing a portion of a stratigraphic model to a particular geological source.

As an example, a method can include elemental analysis. For example, data may be analyzed for various elements, which may be, for example, elements associated with components of rock. As an example, a method that includes elemental analysis can include stoichiometric analysis where, for example, stoichiometry of minerals, etc. may be considered.

As an example, elemental analysis may be utilized to determine an index or indexes (e.g., diagenetic index, detrital index, other index, etc.). As an example, a method can include performing an elemental analysis based at least in part on information acquired via a borehole tool or borehole tools and, for example, calculating values for minerals based at least in part on the elemental analysis.

As an example, data can include XRD data and/or FTIR data. For example, such data may pertain to carbonate minerals. As an example, carbonate minerals may be analyzed as part of a solid solution series (e.g., consider dolomite-ankerite, etc.). As an example, a method can include analyzing data for carbonates (e.g., calcite, ferroan calcite, dolomite, ferroan dolomite, ankerite, siderite, etc.) and plotting analyzed data on a spectrum, for example, with $XY(CO_3)_2$. As an example, XRD data and/or FTIR data may indict concentrations of various minerals, noting that these two techniques can measure concentrations of, for example, Mn, Fe and Mg in minerals differently. As an example, a method can include receiving XRD data and FTIR data and interpreting an index (e.g., a diagenetic index) or indexes based on XRD data and/or based on FTIR data. As an example, a method can include comparing an index based on XRD data to an index based on FTIR data, etc.

As an example, a method may utilize a bulk chemistry approach. For example, consider constructing a solid solution model of carbonates from X-ray fluorescence (XRF) and constructing a diagenetic model, for example, via various chemical elements.

As an example, a method can include determining rock composition of a geologic environment by determining detrital mineral composition values associated with at least one of a plurality of depositional components and calculating a detrital index value based at least in part on the detrital mineral composition values; and determining diagenetic mineral composition values associated with at least one of a plurality of diagenetic components and calculating a diagenetic index value based at least in part on the diagenetic mineral composition values. In such an example, the method can include, based at least in part on the detrital index value and the diagenetic index value, attributing a portion of a stratigraphic model of the geologic environment to a particular geological source.

As an example, a stratigraphic model can be or include a reservoir model. As an example, a stratigraphic model can be or include a completion model (e.g., a completions model). As an example, a stratigraphic model can be or include a reservoir model and a completion model.

As an example, a method can include a detrital index value that is normalized by a quartz composition value. As an example, a method can include a diagenetic index value that is normalized by a calcite composition value. As an example, a method can include a detrital index value that is normalized by a quartz composition value and a diagenetic index value that is normalized by a calcite composition value. As an example, a method can include calculating one or more non-normalized index values (e.g., a non-normalized detrital index value and/or a non-normalized diagenetic index value, etc.). As an example, a method can include analyzing data and/or indexes for one or more trends.

As an example, a method can include determining that rock composition of a geologic environment includes at least one igneous deposit. For example, consider a scenario where at least one of the at least one igneous deposit has a thickness less than approximately 10 cm or, for example, less than approximately 5 cm or, for example, less than about 2.5 cm.

As an example, a method can include implementing different types of borehole tool sensors where at least one of the types of implemented borehole tool sensors acquires raw data with a resolution less than approximately 10 cm.

As an example, different types of borehole tool sensors can include, for example, one or more of a micro-resistivity sensor, a photoelectric factor sensor, an image sensor, a dielectric and conductivity dispersion sensor, a neutron porosity sensor, and an ultrasonic sensor.

As an example, a method can include adjusting a completion plan based at least in part on an identified at least one igneous deposit. For example, consider a stratigraphic model that includes an igneous deposit where a completion is to be constructed through the igneous deposit. In such an example, the completion plan may account for the presence of the igneous deposit. As an example, an igneous deposit can be or include a weathered volcanic ash bed.

As an example, a method can include receiving data for a geologic environment where the data include data acquired via different types of borehole tool sensors; based at least in part on the data, determining rock composition of the geologic environment where the rock composition includes depositional components and diagenetic components; and, based at least in part on the rock composition, outputting a stratigraphic model of at least a portion of the geologic environment. In such an example, the data can include sonic data, NMR data and gamma ray spectroscopy data.

As an example, a method can include determining at least one pore characteristic that is or includes a surface to volume ratio or a volume to surface ratio based at least in part on a portion of NMR data and/or determining at least one value for the Thomsen gamma parameter based at least in part on at least a portion of sonic data.

As an example, a system can include a processor; memory accessibly by the processor; instructions stored in the memory and executable by the processor to instruct the system to receive data for a geologic environment where the data include data acquired via different types of borehole tool sensors; based at least in part on the data, determine rock composition of the geologic environment where the rock composition includes depositional components and diagenetic components; and, based at least in part on the rock composition, output a stratigraphic model of at least a portion of the geologic environment.

As an example, one or more computer-readable storage media can include processor-executable instructions where the processor-executable instructions include instructions to instruct a computer to receive data for a geologic environment where the data include data acquired via different types of borehole tool sensors; based at least in part on the data, determine rock composition of the geologic environment where the rock composition includes depositional components and diagenetic components; and, based at least in part on the rock composition, output a stratigraphic model of at least a portion of the geologic environment.

The method 300 is shown in FIG. 3 in association with various computer-readable media (CRM) blocks 311, 321 and 331 (e.g., non-transitory media that are not carrier waves and that are not signals). Such blocks generally include instructions suitable for execution by one or more processors (or cores) to instruct a computing device or system to perform one or more actions. While various blocks are shown, a single medium may be configured with instructions to allow for, at least in part, performance of various actions of the method 300. As an example, a computer-readable storage medium (CRM) is a non-transitory computer-readable storage medium that is not a carrier wave and that is not a signal. One or more CRM blocks may be provided for graphical user interfaces (GUIs), etc. One or more CRM blocks may be provided for rendering information to a display, etc. (e.g., consider rendering a model to a display, etc.).

Figure 4:
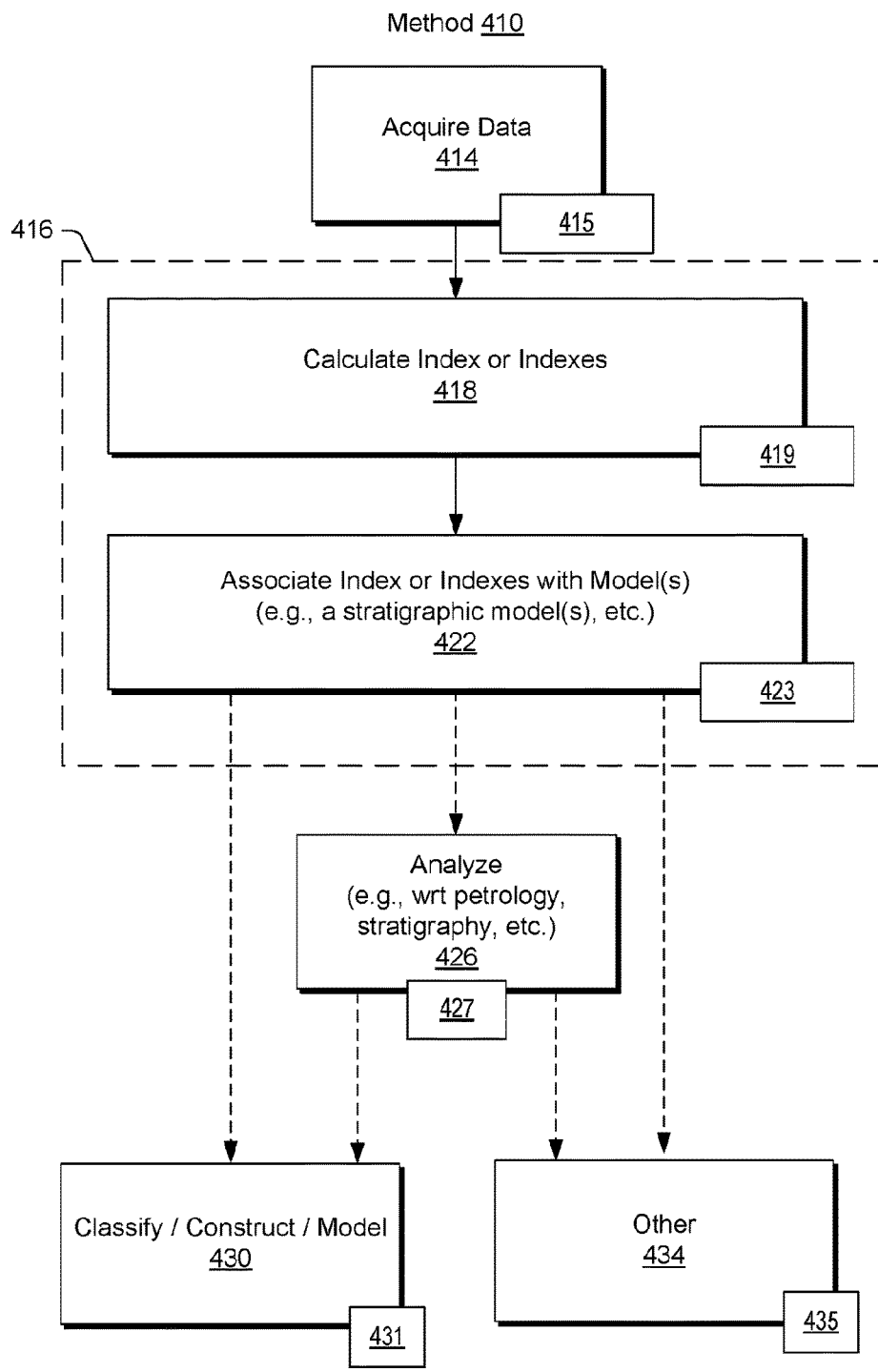
FIG. 4 illustrates an example of a method.

FIG. 4 shows an example of a method 410, which may be a workflow. As shown, the method 410 includes an acquisition block 414 for acquiring data; a calculation block 418 for calculating one or more indexes based at least in part on the acquired data; an association block 422 for associating the one or more indexes with one or more models (e.g., consider a stratigraphic model, etc.); an analysis block 426 for analyzing the associated information with respect to one or more of petrology, stratigraphy, etc.; a classification, construction, modeling block 430 for one or more of classifying rock, constructing stratigraphic units and modeling; and an other block 434 for performing one or more other processes.

In the example of FIG. 4, the blocks 418 and 422 may form a process 416, which may be implemented in one or more methods, workflows, etc. As an example, the calculation block 418 may include calculating a detrital index and/or a diagenetic index (see, e.g., Eqns. (1) and (2), above). As an example, the association block 422 may include associating index values with positional information such as, for example, stratigraphy (e.g., stratigraphic information), which may characterize a model or models of a subterranean environment. As an example, the association block 418 may include plotting index values within a framework (e.g., PETREL®, TECHLOG®, etc.). For example, a framework may include stratigraphic information and the association block 418 may include associating index values with the stratigraphic information and, for example, rendering to a display one or more plots that illustrate index values in a spatial and/or temporal context (e.g., 1 D, 2D, 3D, 4D, etc.).

As to the acquisition block 414, data may be acquired from equipment that is implemented in the field or, for example, field data may be received via a network, a storage device, etc. As an example, acquisition equipment may include wireline equipment, core sample analysis equipment, cuttings analysis equipment, etc.

As an example, the analysis block 426 may include validating one or more index values based at least in part on one or more other types of information such as, for example, petrological information and stratigraphic information.

As an example, the classification, construction and modeling block 430 may include one or more of refining rock classifications, constructing stratigraphic units (e.g., as to basin and petroleum systems modeling, optionally as inputs to a framework or frameworks) and constructing a model such as a completion model (e.g., for input to a framework or frameworks).

As an example, a completion model (e.g., or completions model) may be part of a framework such as a simulation framework that may include one or more modules that can stimulate a geologic environment, for example, to generate one or more fractures. For example, consider the commercially available MANGROVE® engineered stimulation design package that may be operated in conjunction with a framework such as, for example, the PETREL® framework (e.g., optionally in the OCEAN® framework). The MANGROVE® package may be operated as a hydraulic fracturing simulator and may be, for example, integrated into one or more seismic-to-simulation workflows (e.g., for conventional and/or unconventional reservoirs). As an example, the MANGROVE® package may be implemented to grid and model complex fractures, which may be used for reservoir simulation.

As an example, the other block 434 may include distinguishing rock properties for one or more mining operations (e.g., exploration of alluvial diamond mines, etc.), distinguishing hydrothermal alterations in geothermal exploration (e.g., as to sandstones, siltstones, mudstones, etc.; consider the Salton Sea Geothermal Project, etc.), and distinguishing rock in construction projects to characterize subsurface geology (e.g., as to tunnels, foundations, etc.).

The method 410 is shown in FIG. 4 in association with various computer-readable media (CRM) blocks 415, 419, 423, 427, 431 and 435. Such blocks can be computer-readable storage media blocks.

Figure 5:
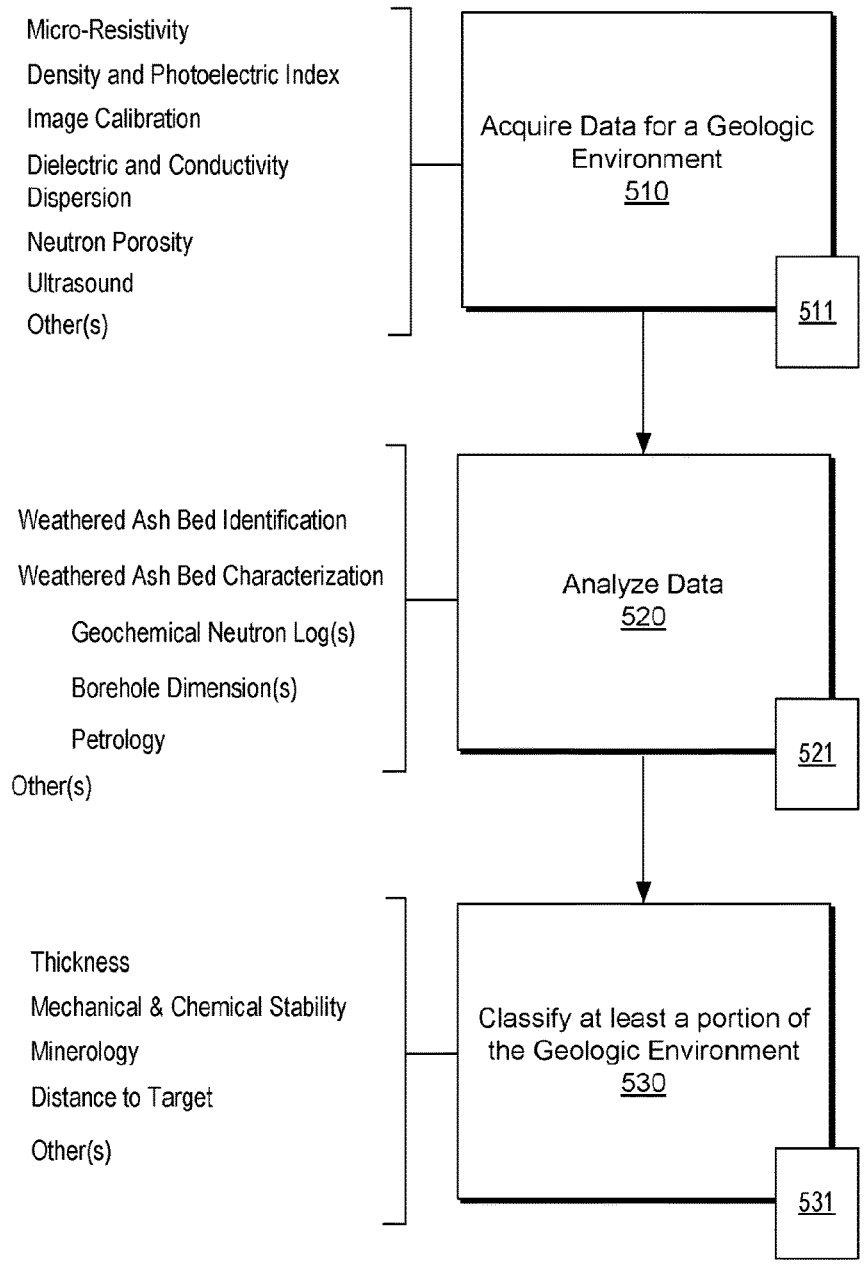
FIG. 5 illustrates an example of a method.

FIG. 5 shows an example of a method 500 that includes an acquisition block 510 for acquiring data for a geologic environment, an analysis block 520 for analyzing the data, and a classification block 530 for classifying at least a portion of the geologic environment based at least in part on the analysis of the data.

As shown in the example of FIG. 5, the acquisition block 510 may acquire data (e.g., and/or receive data) as measured via one or more techniques. Such techniques may include a micro-resistivity technique, a density and photoelectric factor or index technique, an image calibration technique, a dielectric and conductivity dispersion technique, a neutron porosity technique, an ultrasound technique, etc.

As shown in the example of FIG. 5, the analysis block 520 may analyze at least a portion of the acquired data to identify an igneous deposit (e.g., a weathered ash bed, etc.), to characterize an igneous deposit (e.g., a weathered ash bed, etc.), etc.

As shown in the example of FIG. 5, the classification block 530 may classify at least a portion of a geologic environment based at least in part on an analysis. A classification may consider thickness, mechanical stability and/or chemical stability, mineralogy, distance to a target, etc.

The method 500 is shown in FIG. 5 in association with various computer-readable media (CRM) blocks 511, 521 and 531. Such blocks can be computer-readable storage media blocks. While various blocks are shown, a single medium may be configured with instructions to allow for, at least in part, performance of various actions of the method 500.

As an example, a method can include receiving data for a geologic environment, the data acquired via a plurality of different measurement techniques; analyzing the data as to the presence of at least one igneous deposit; and classifying at least a portion of the geologic environment based at least in part on the analyzing. In such an example, at least one of the at least one igneous deposit may include a thickness less than approximately 10 cm, a thickness less than approximately 5 cm, and/or a thickness less than approximately 2.5 cm. As an example, a thickness criterion or thickness criteria may be implemented as part of a method that includes analyzing data. As an example, such a criterion or criteria may be based at least in part on a resolution of a measurement technique (e.g., an equipment-based resolution, etc.). As an example, a method may include an adjustable thickness parameter, which may be adjusted based on a specification (e.g., equipment, etc.), an operation, a model, etc. As an example, a thickness parameter may be selected based at least in part on a development plan, a completion plan, etc.

As an example, a method can include detecting igneous deposits through wireline logs in organic shale plays. As an example, a method may include preparing data (e.g., processing acquisition tool data, etc.); detecting one or more igneous deposits based at least in part on data from a plurality of sources (e.g., different types of acquisition tools); and classifying one or more igneous deposits.

As an example, data from a plurality of sources may act to combine pieces of information that may each relate to one or more possible aspects of an igneous deposit. As an example, information may be processed for igneous deposit identification (e.g., in a data preparation or conditioning process) and combined (e.g., as part of a data integration process). As to classification of one or more detected igneous deposits, a method may reference a matrix of criteria such as, for example, thickness criteria, mineralogical criteria, mechanical strength criteria, distance to target criteria, etc. In such an example, a method may assess and rank detected igneous deposits. As an example, one or more detected igneous deposits may be associated with one or more recommendations as to a completion compatibility study, a completion planning model, etc. Such recommendations may help to mitigate possible hazards associated with one or more individual igneous deposits. As an example, a method may include an automated process that can classify one or more detected igneous deposits. Such a method may be automatized depending on one or more factors such as, for example, available input, specific reservoir conditions, etc.

As an example, a workflow may include detecting one or more igneous deposits and modeling the one or more igneous deposits in a simulation model. For example, a simulation model may be a reservoir simulation model, a completions simulation model, a petroleum systems simulation model, etc.

As an example, a method may include processing high resolution micro-resistivity log information. Such a method may optionally operate without filtering of raw micro-log tool data. As an example, depth-matching depth shift may be performed. As an example, micro-log resistivity log information may optionally be used as part of a borehole image calibration process.

As an example, a Micro-Cylindrically Focused Log (MCFL) tool may be used to acquire resistivity data such as, for example, output as B0_HR, B1_HR and B2_HR, corresponding to a main button measurement and two shallower measurements. In such an example, B1_HR and B2_HR may offer a better vertical resolution than B0_HR. As an example, in case of logs in mudstone formation where no mudcake build or invasion takes place, data may be used as to formation resistivity.

As an example, a method can include receiving sonic, NMR, and gamma ray spectroscopy log data and analyzing such data in a manner that can integrate information therein within a geologic context. As an example, data can include mechanical data. As an example, various types of data that include types such as sonic, NMR and gamma ray spectroscopy data can be analyzed for predictive modeling of rock. As an example, such predictive modeling can be for rock that is at a distance from a surface of a bore. For example, a method can include receiving and analyzing data to predict depositional and/or diagenetic characteristics of rock that is located a distance from a surface of rock that defines a bore in a geologic environment.

As an example, a method can include modeling where modeling can provide information as to one or more of mineral and mechanical stratigraphy, hydrocarbon migration and timing of porosity generation, generation of completion logs, and development of textural models of the rock formations.

As an example, various mechanical properties of rocks can be used for completion data (e.g., consider Thomson's gamma from sonic data). However, such logs may be lacking as to a geologic context, which can confound determinations as to why various rocks behave as they do. As such, sonic data alone, from a given bore (e.g., well), may provide poor estimates as to how rock surrounding one or more other bores might behave (e.g., consider bores within a neighborhood defined by a distance, etc.). As an example, mineral indices from a gamma ray spectroscopy tool can provide geologic context of a rock; however, they may be lacking as to mechanical data for a completion.

As an example, a workflow can include integrating information of a bore as acquired using various types of equipment (e.g., sonic, NMR and gamma ray spectroscopy) such that that geologic data can be used to predict conditions away from that particular bore. In such an example, the predicted conditions may aid in planning, executing, etc. operations as to one or more other bores (e.g., wells, etc.). As an example, a model can be generated that extends spatially to one or more regions where a bore may be drilled into a geologic environment and/or where a bore that exists may be further worked upon, completed, etc.

Figure 6:
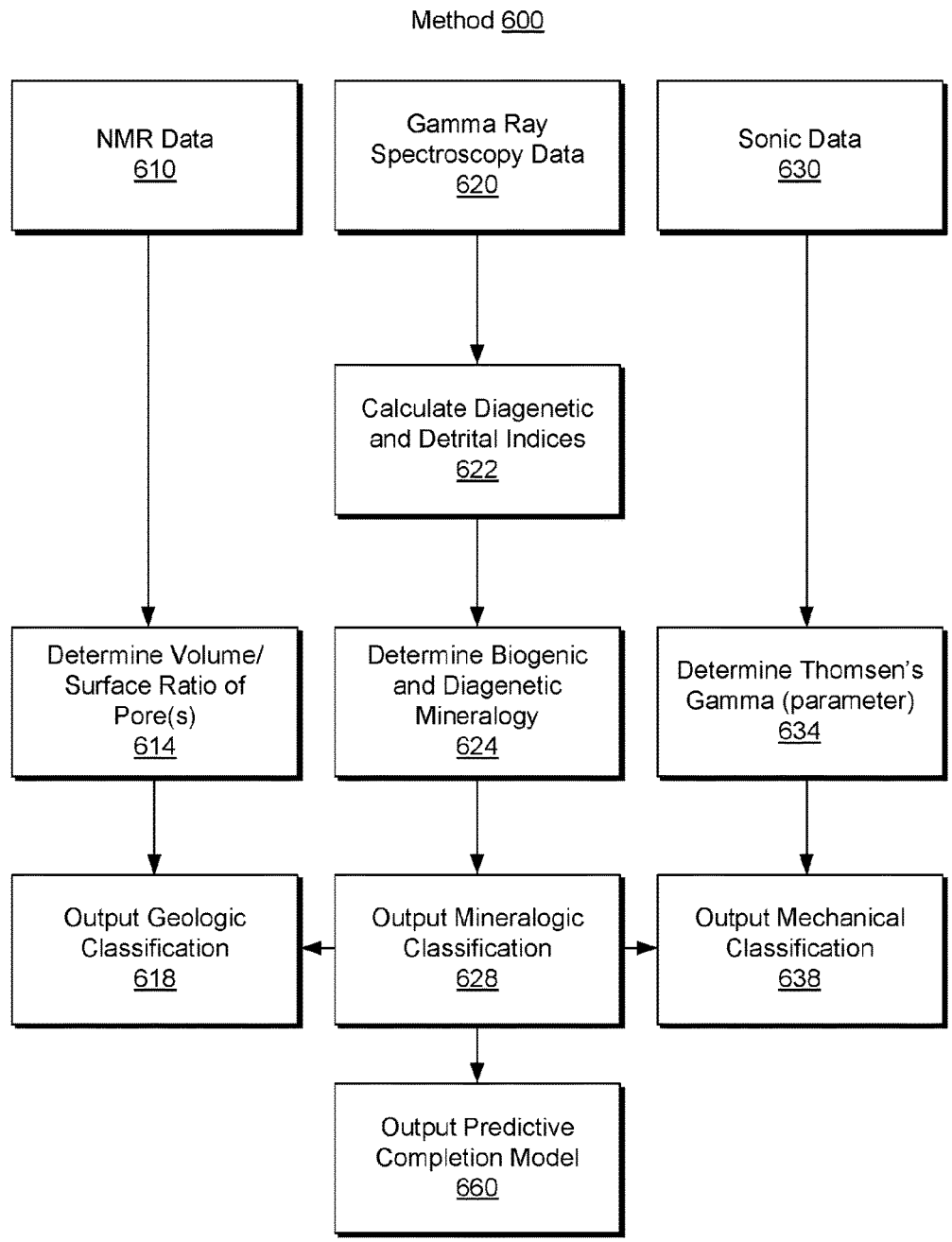
FIG. 6 illustrates an example of a method.

FIG. 6 shows an example of a method 600 that includes reception blocks 610, 620 and 630 for receiving NMR data, gamma ray spectroscopy data and sonic data, respectively. In such an example, the received data can be data associated with a single bore in a geologic environment. For example, such a bore may be an exploratory bore, a bore to be completed to become an operational well, etc. As an example, a bore may be in a field where multiple bores are to be drilled (e.g., within a planned area of the field).

In the example of FIG. 6, the method 600 includes three determination blocks 614, 624 and 634 for determining various values. For example, the determination block 614 can include determining volume/surface ratio of a pore or pores; the determining block 624 can include determining biogenic and diagenetic mineralogy, for example, based at least in part on a calculation block 622 where diagenetic and detrital indices may be calculated based at least in part on at least a portion of the gamma ray spectroscopy data; and the determination block 634 can include determining Thomsen's gamma.

As shown in the example of FIG. 6, the method 600 includes three output blocks 618, 628 and 638 that can include outputting geologic classification(s), outputting mineralogic classification(s) and outputting mechanical classification(s). The method 600 includes another output block 660 for outputting a predictive model that may be a predictive completion model. Such a model may be suitable for use in determining one or more characteristics of a region of a geologic environment where a bore exists or is to be drilled and completed, for example, to become an operational well.

The method 600 can be associated with one or more computer-readable media (CRM) blocks. Such blocks can be computer-readable storage media blocks. As an example, a single medium may be configured with instructions to allow for, at least in part, performance of various actions of the method 600.

Rocks may be complexes of primary minerals, fossils, and organic materials that form at the time they are deposited, and secondary minerals that form after deposition. As an example, primary minerals may be used for stratigraphic correlation across a basin while secondary minerals may impart physical properties (e.g., as may be measured for completion engineering and design).

Stratigraphic and diagenetic effects can exhibit different spatial distributions. As such, attributing mineralogy spatially can improve prediction of reservoir and rock properties (e.g., within a play, a basin, etc.). As an example, a workflow can include distinguishing different types of minerals and grouping them in stratigraphic intervals. Such an approach may be applied to enhance a stratigraphic model, a completion model, etc.

As an example, a stratigraphic model may provide for stratigraphic analysis. For example, a stratigraphic analysis can include an analysis of one or more of the history, composition, relative ages and distribution of strata, and the interpretation of strata to elucidate Earth history. As an example, the comparison, or correlation, of separated strata can include study of one or more of their lithology, fossil content, and relative or absolute age, or lithostratigraphy, biostratigraphy, and chronostratigraphy. As an example, a stratigraphic model can include zones. For example, a method can include outputting information that associates one or more characteristics with a portion of a geologic environment where collectively the one or more characteristics may define a zone.

Figure 7:
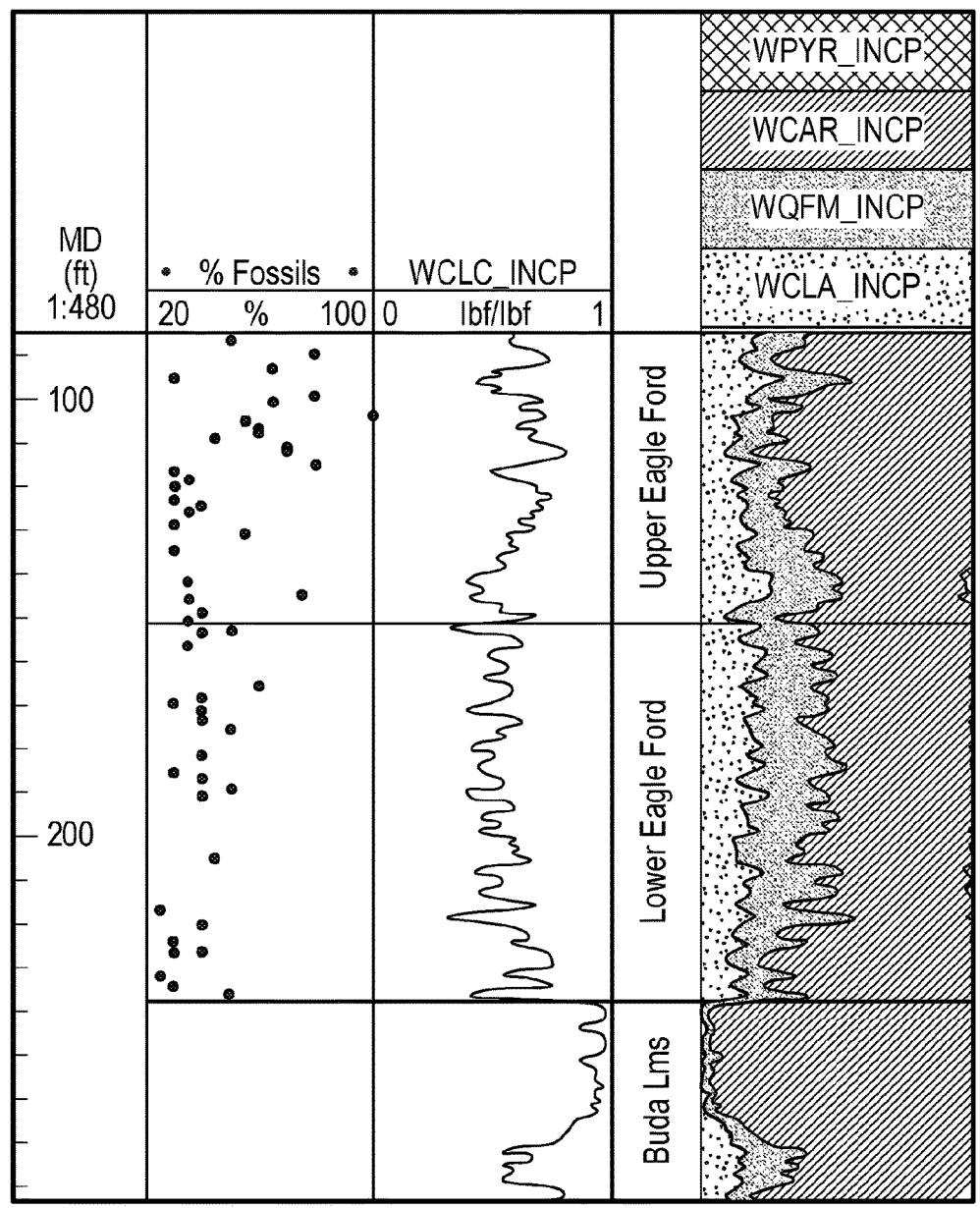
FIG. 7 illustrates examples of plots.

As an example, a workflow may include receiving information as to trace mineral content within rock (e.g., rock composition) to distinguish the environment in which the rock was formed. For example, FIG. 7 shows an example of a plot 700 that includes various types of information associated with a spatial dimension (e.g., depth). As shown, the plot 700 includes information as to the Eagle Ford Formation, which includes sedimentary rock from the Late Cretaceous age (e.g., including organic matter-rich fossiliferous marine shale).

Specifically, the plot 700 shows information for a well in the Eagle Ford Formation in a region dominated by carbonate and specifically calcite where it may be unclear as to what distinguishable rock types exist within the carbonate matrix. As an example, a change in fossil count with respect to depth may suggest a difference in rock composition (e.g., and properties) between the Upper and Lower Eagle Ford (see labels in the plot 700).

In the plot 700, bulk mineralogy suggests that the Upper and Lower Eagle Ford Formation include mineralogy with differences that are relatively small. However, the fossil count, which is based on petrologic analysis, indicates that the carbonates of the upper and lower Eagle Ford Formation come from different sources. Thus, while the total carbonate may be comparable (e.g., relatively small differences), the source and properties can differ.

As an example, the detrital index and/or the diagenetic index may be applied to data acquired in a well of a formation (e.g., the Eagle Ford Formation, etc.). Such indices may utilize trace mineral information. For example, the detrital index (Eqn. 1) may use depositional (e.g., biotite, muscovite, orthoclase) information, which may be "normalized" (e.g., divided by, etc.) quartz to extract depositional mineralogy.

As an example, a method can include calculating a diagenetic index based on diagenetic mineral composition values in a localized environment, optionally where the diagenetic index is normalized by a calcite value. As an example, a method can include calculating a detrital index based on detrital mineral composition values in a localized environment, optionally where the detrital index is normalized by a quartz value. As an example, a method can include calculating a detrital index and calculating a diagenetic index.

Figure 8:
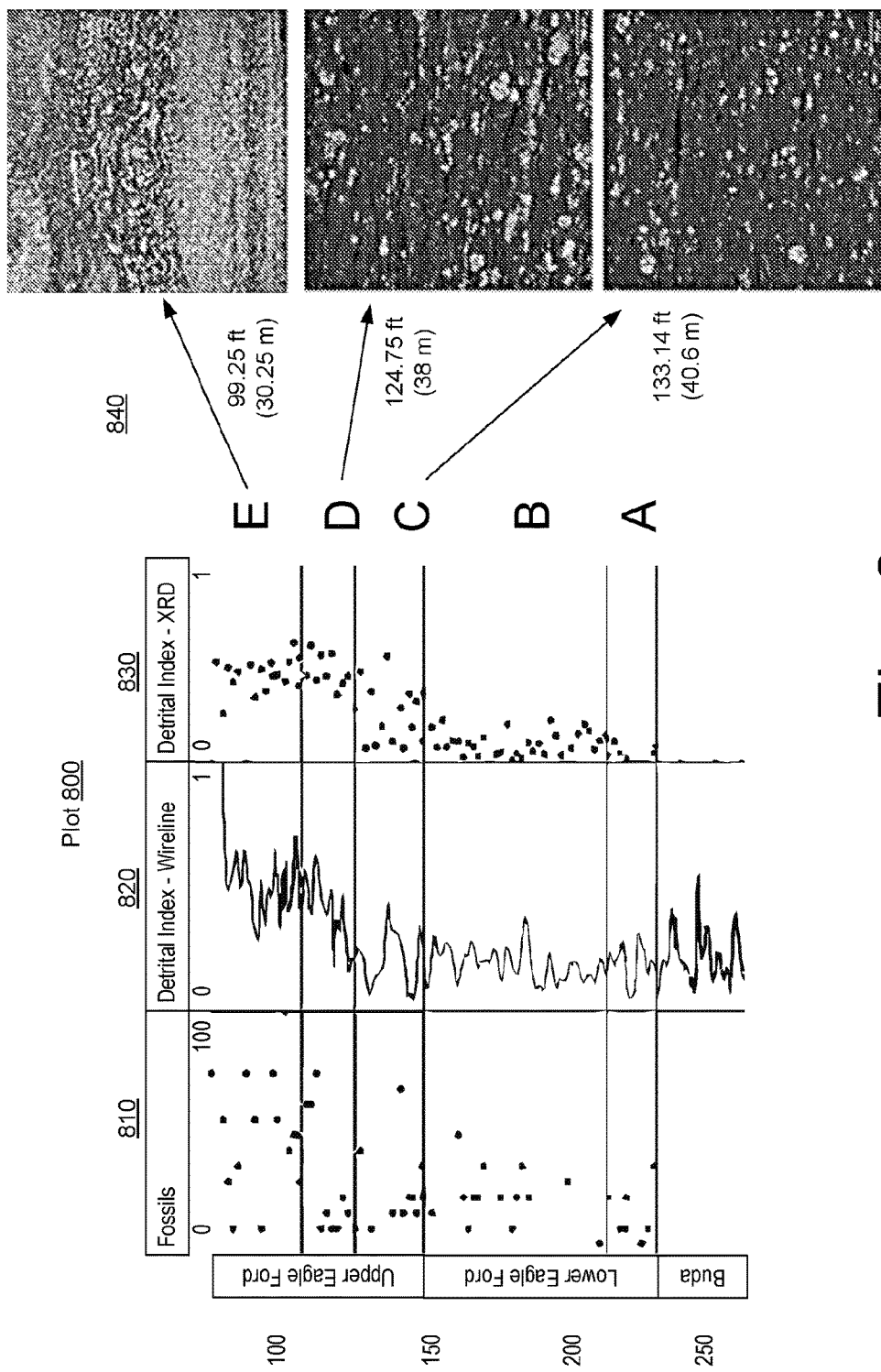
FIG. 8 illustrates examples of plots and examples of images.

FIG. 8 shows an example of a plot 800 that includes fossil values 810 and detrital index values 820 and 830 for two different types of acquired data as plotted against a spatial dimension (e.g., depth). FIG. 8 also shows stratigraphic information 840 for an associated region of the Eagle Ford Formation.

In the plot 800, the detrital index values 820 are based on wireline acquired data (e.g., lithology scanning technology) and the detrital index values 830 are based on XRD data. As shown, the stratigraphic units labeled A, B, C, D and E match changes determined by the detrital index values. The fossil values 810 are fossil counts based on petrologic analysis, as measured from thin sections (e.g., final column), which can provide a measure of "ground truth" (e.g., to validate one or more detrital index values, a detrital index equation, underlying detrital data, etc.). The detrital index values 830 based on XRD data account for illite while the detrital index values 820 based on the wireline data do not, which can explain discrepancies in matching (e.g., validation) of the D stratigraphic unit (see, e.g., portion of Upper Eagle Ford).

As an example, a workflow can include calculating a diagenetic index (see, e.g., Eqn. (2)) that highlights diagenetic elements of a rock. Such an approach may act to reduce the influence of minerals that may be found in high concentrations or, for example, that could be detrital and diagenetic. A diagenetic index may be applied to characterization of source rocks that are argillaceous. As an example, a method may include calculating one or more metrics based at least in part on a detrital index and based at least in part on a diagenetic index. In such an example, the metric or metrics may help to define rock classes or intervals that can be used for modeling stratigraphy, modeling completions, etc. (e.g., within basin, etc.).

Figure 9:
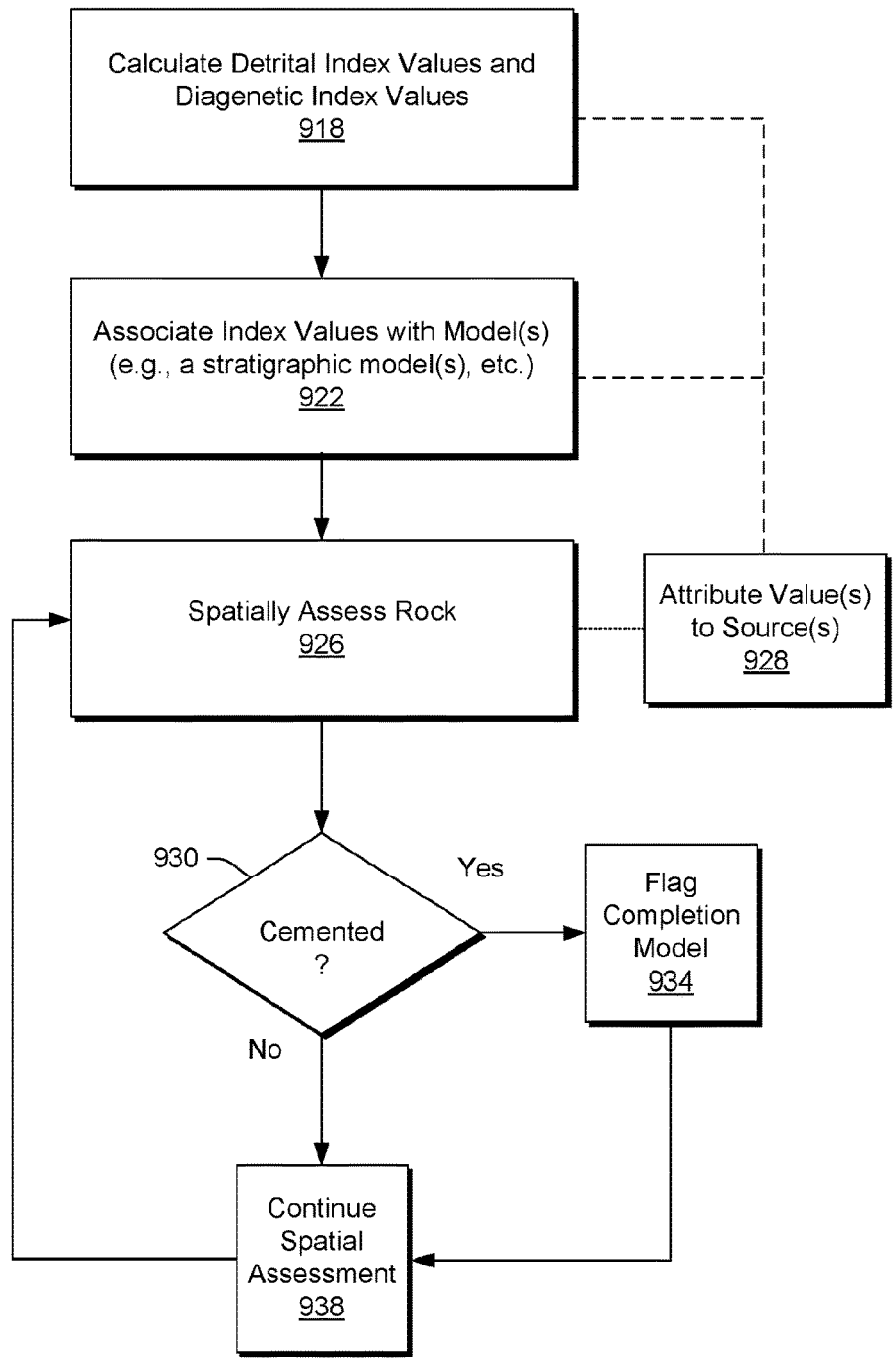
FIG. 9 illustrates an example of a method.

FIG. 9 shows an example of a method 910 that includes a calculation block 918 for calculating detrital index values and diagenetic index values, an association block 922 for associating the index values with a model or models, an assessment block 926 for spatially assessing rock based at least in part on the index values (see, e.g., attribution block 928 for attributing rock(s) to a source(s)), a decision block 930 for deciding whether a spatial region is cemented, a flag block 934 for flagging a completion model as to a cemented region, and a continuation block 938 for continuing a spatial assessment of rock. As shown in the example of FIG. 9, a cemented region may be indicated via one or more index values associated with spatial coordinates (e.g., of a model of a subterranean environment). In such an example, the region may be flagged in a completion framework such that completion modeling (e.g., planning, etc.) may account for the cemented region (e.g., as to drilling, casing, etc.). As an example, the method 910 of FIG. 9 may be part of a workflow.

In the example of FIG. 9, the attribution block 928 may include accessing one or more fingerprints that may be associated with one or more sources. For example, consider a chemical fingerprint, a mineralogical fingerprint, etc. As an example, a detrital index value may be compared to an index value that is based at least in part on a compositional fingerprint of rock. In such an example, where a match occurs (e.g., within error limits, etc.), the detrital index value may indicate that rock upon which the detrital index value is based may be attributed to a particular source.

As an example, a method can include calculating a detrital index value based at least in part on detrital mineral composition values of a geologic environment; and based at least in part on the detrital index value, attributing a portion of the geologic environment to a particular geological source. In such an example, the detrital index value may be calculated based at least in part on a quartz composition value, for example, the index may be normalized by a quartz composition value.

As an example, a particular geological source can include a chemical fingerprint. As an example, an index value may provide for attributing a portion of a geologic environment to a geologic source based at least in part on a chemical fingerprint (e.g., which may be cast as an index value, etc.). As an example, a particular geological source can include a mineralogical fingerprint. As an example, an index value may provide for attributing a portion of a geologic environment to a geologic source based at least in part on a mineralogical fingerprint (e.g., which may be cast as an index value, etc.).

As an example, a method can include calculating a detrital index value based at least in part on detrital mineral composition values of a geologic environment and calculating a diagenetic index value based at least in part on diagenetic mineral composition values of the geologic environment. Such a method may include attributing a portion of the geologic environment to a particular geological source is based at least in part on the diagenetic index value and based at least in part on the detrital index value.

As an example, a method can include calculating a diagenetic index value based at least in part on diagenetic mineral composition values of a geologic environment; and based at least in part on the diagenetic index value, attributing a portion of the geologic environment to a particular geological source. In such an example, the diagenetic index value may be calculated based at least in part on a calcite composition value, for example, the index may be normalized by a calcite composition value.

As an example, a particular geological source can include a chemical fingerprint. As an example, one or more index values may provide for attributing a portion of a geologic environment to a geologic source based at least in part on a chemical fingerprint (e.g., which may be cast as an index value, index values, etc.). As an example, a particular geological source can include a mineralogical fingerprint. As an example, one or more index values may provide for attributing a portion of a geologic environment to a geologic source based at least in part on a mineralogical fingerprint (e.g., which may be cast as an index value, index values, etc.).

As an example, a system can include a processor; memory accessibly by the processor; and one or more modules stored in the memory where the one or more modules include processor-executable instructions to instruct the system and where the instructions include instructions to calculate a detrital index value based at least in part on detrital mineral composition values of a geologic environment, and calculate a diagenetic index value based at least in part on diagenetic mineral composition values of a geologic environment. In such an example, the detrital index value may be calculated based at least in part on a quartz composition value, for example, the detrital index may be normalized by a quartz composition value; and/or the diagenetic index value may be calculated based at least in part on a calcite composition value, for example, the diagenetic index may be normalized by a calcite composition value.

As an example, a system can include instructions to, based at least in part on a detrital index value, attribute a portion of the geologic environment to a particular geological source. As an example, a system can include instructions to, based at least in part on the diagenetic index value, attribute a portion of the geologic environment to a particular geological source. As an example, a system can include instructions to, based at least in part on a detrital index value and based at least in part on a diagenetic index value, attribute a portion of the geologic environment to a particular geological source.

As an example, a system can include instructions to calculate a plurality of detrital index values for at least a portion of a geologic environment and/or instructions to calculate a plurality of diagenetic index values for at least a portion of the geologic environment.

As an example, a system can include instructions to model a completion in a geologic environment based at least in part on a detrital index value and/or instructions to model a completion in the geologic environment based at least in part on the diagenetic index value. As an example, a system can include instructions to calculate a metric value based at least in part on a detrital index value and based at least in part on a diagenetic index value. As an example, a system can include instructions to characterize at least a portion of a geologic environment with respect to cementation based at least in part on one or more index values (e.g., detrital and/or diagenetic index values).

Figure 10:
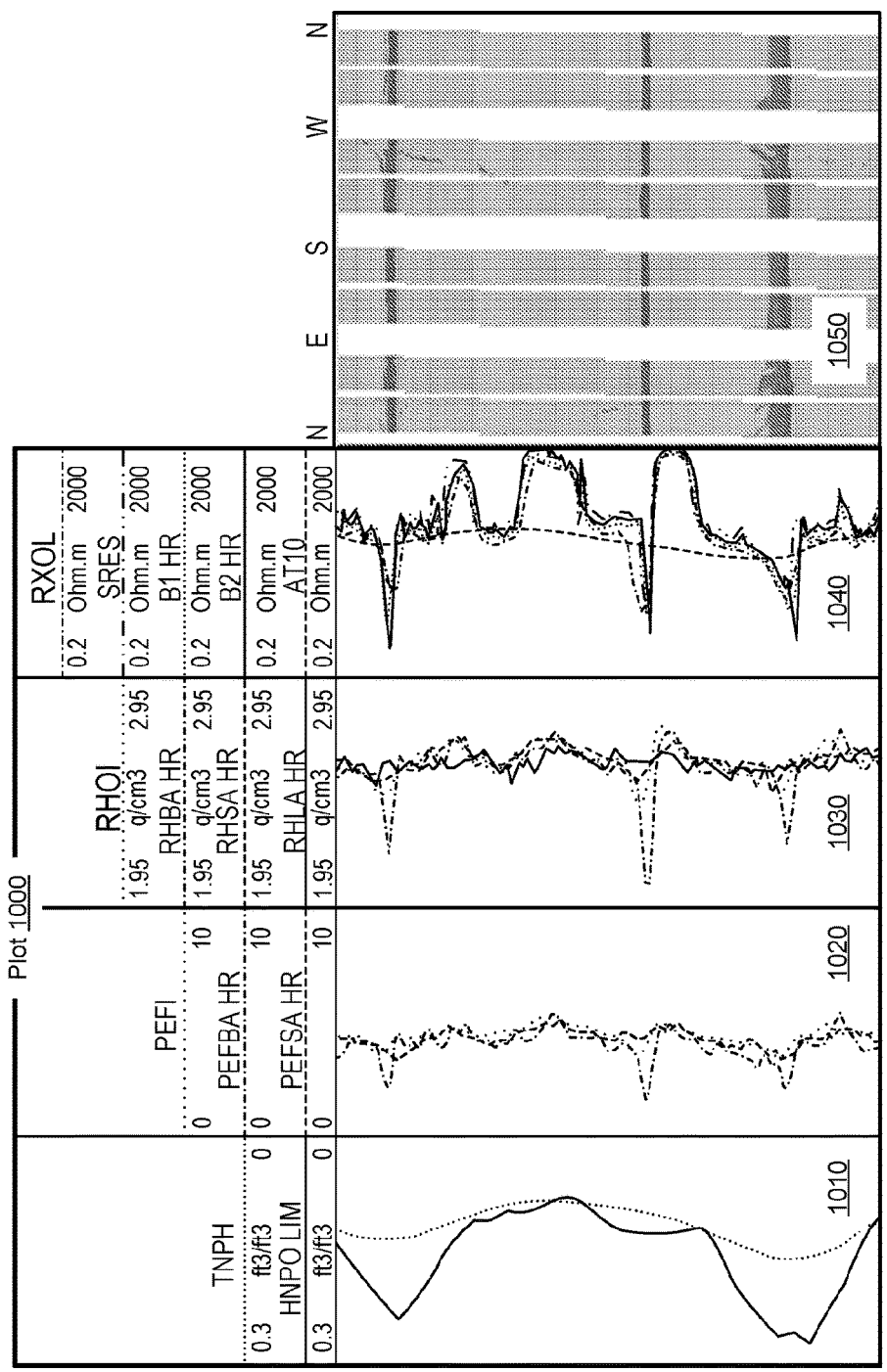
FIG. 10 illustrates examples of plots.

As mentioned with respect to the method 500 of FIG. 5, data may be analyzed as to one or more characteristics such as, for example, one or more characteristics of an igneous deposit. FIG. 10 shows an example of a plot 1000 that includes five tracks of data 1010, 1020, 1030, 1040 and 1050. The track 1040 shows an example of a high resolution processed micro-resistivity log (e.g., curves corresponding to B1_HR and B2_HR). In the track 1040, these curves may be compared with another curve, which corresponds to lower resolution data using micro resistivity RXOI. In the track 1040 data, igneous deposits (e.g., ash beds) can be detected as low resistivity peaks (see, e.g., the curves that correspond to B1_HR and B2_HR). As an example, a method may include processing data to output high resolution shallow resistivities, which may allow, at least in part, for detection of one or more igneous deposits.

As an example, a method can include processing density and photoelectric factor (PE) log data. As an example, such a method can process such data in a manner that allows for retrieving information on igneous deposits as thin as about 2.5 cm (e.g., a thickness of about one inch). Density tends to be related to porosity of an igneous deposit while PE may provide an indication as to composition. As an example, a tool with at least one short detector (e.g., less than about 15 cm) spacing may be used to provide for detection of igneous deposits of about 2.5 cm.

As an example, a three-detector litho-density tool may be implemented for acquisition of data. As an example, a method may include computing high resolution mono-sensor density and PE for backscatter. As an example, where mudcake does not form in front of an organic shale, backscatter density and PE may represent formation density and PE. As an example, short spacing density and PE together with long spacing density may be used to quality control backscatter output.

In FIG. 10, the tracks 1020 and 1030 show PE (PEFI) and "Very High Resolution" (VHR) density (RHOI), which may be compared with high resolution backscatter data (RHBA_HR), short spacing (RHSA_HR) and long spacing (RHLA_HR) mono-sensor densities. While the RHOI data show dynamics somewhat akin to RHSA_HR, the RHOI data is insufficient for igneous deposit detection; igneous deposits are shown by RHBA_HR, as well as PEFBA_HR.

As an example, a method can include image calibration. Image calibration may include conversion of conductive curves into a synthetic resistivity curve (SRES), for example, using a true resistivity log. The selection of the reference resistivity log can impact calibrated image resistivity. Image average resistivity calibration may be performed using high resolution resistivity, for example, as explained above, in case of mudstone. As an example, a method can include depth matching prior to image calibration. Such an approach may avoid introduction of biases and distortion (e.g., due to lower resolution and potential shoulder bed effects). In the instance that a micro log is unavailable, low resolution resistivity data may be used, for example, in a manner that aims to avoid biases and distortion effects (e.g., provided a button-averaged log used for calibration is filtered over a resolution of the calibration curve).

In FIG. 10, track 1040 shows the image average resistivity (SRES) calibrated with micro resistivity (B1_HR) while the track 1050 shows image data. The calibration appears as a linear function in the logarithmic scale. B1_HR and B2_HR show a vertical resolution akin to the button-averaged image resistivity. For reference, vertical resolution induction resistivity AT10 is plotted in the track 1040 of FIG. 10. As an example, data as in the track 1040 may be used for igneous deposit detection. For example, one or more ash beds may be detected as low resistivity/conductive dark beds on a static normalized image with low SRES value. As an example, a method can include processing data to output image-averaged resistivity and resistivity images, calibrated (scaled), static and dynamic.

Referring to FIG. 10, the tracks, which are shown with a dimension in feet (e.g., depth), include a neutron porosity track 1010, a photoelectric factor track 1020, a density track 1030, a micro resistivity track 1040 and a static borehole image track 1050. As explained above, igneous deposits may be detected via processing and analysis of data (see, e.g., PEFBA_HR, RHBA_HR, B1_HR, B2_HR, and SRES and as conductive response on the static image of the track 1050).

As an example, a method can include processing of dielectric dispersion logs. For example, a method can include high resolution processing of apparent conductivity and apparent permittivity curves. As an example, dielectric logs can allow for measuring permittivity, which is sensitive to water content in a formation. As an example, one or more ash beds may be detected as thin beds with high conductivity and permittivity values. As an example, processing may provide for unfiltered apparent permittivity and conductivity. As an example, a deconvolution algorithm may be implemented to reconstruct shoulder-bed effect-free permittivity and conductivity. As an example, individual array data may be processed independently to preserve radial information. As an example, arrays for a given frequency may share a common formation model. As an example, an inclusive algorithm may be employed that increases robustness of results and that permits estimation of size and properties of one or more igneous deposits thinner than about 5 cm (e.g., about 1 inch to about 2 inch resolution).

Figure 11:
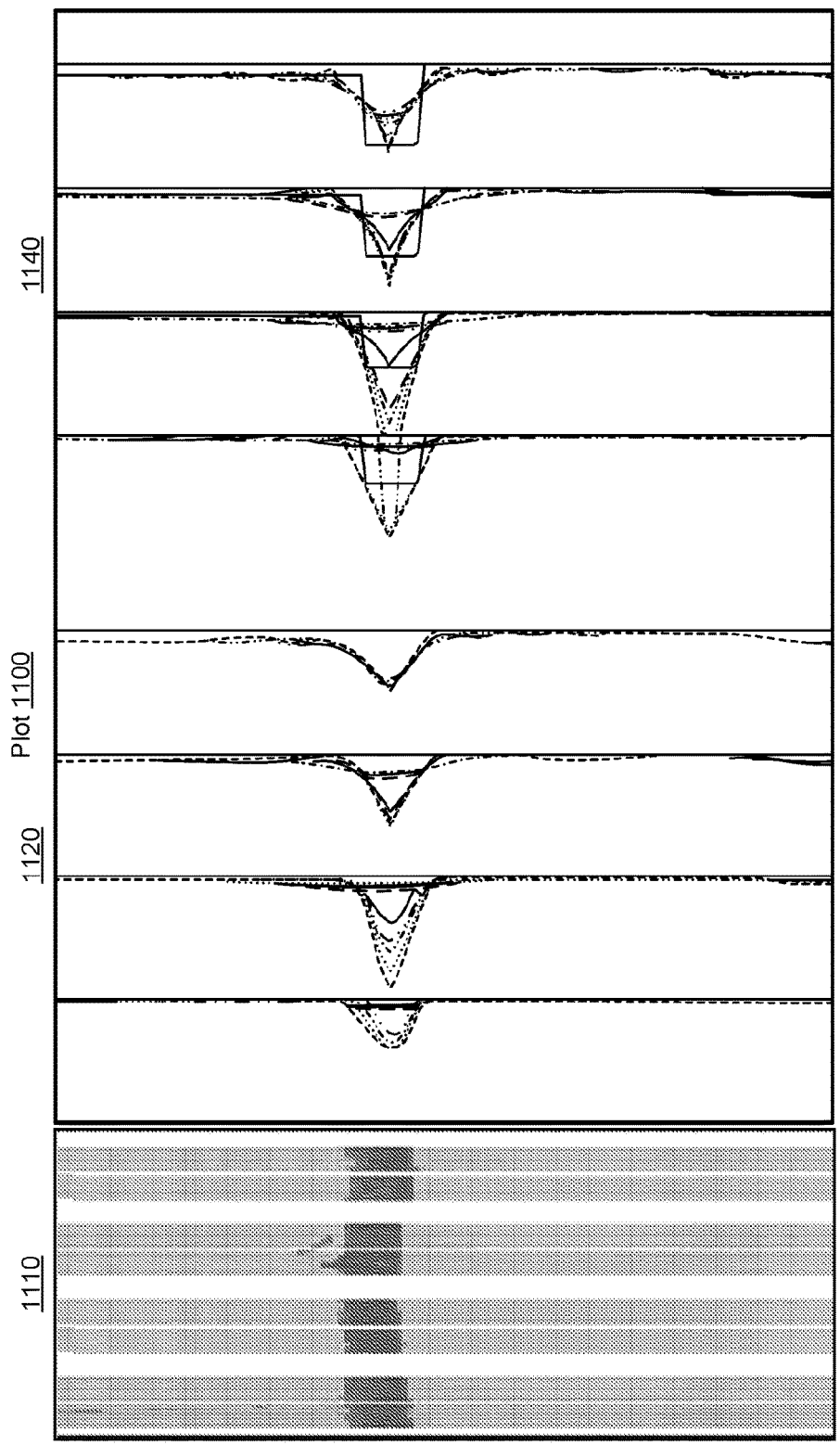
FIG. 11 illustrates an example of a compositional model of materials with respect to various measurement techniques.
Figure 12:
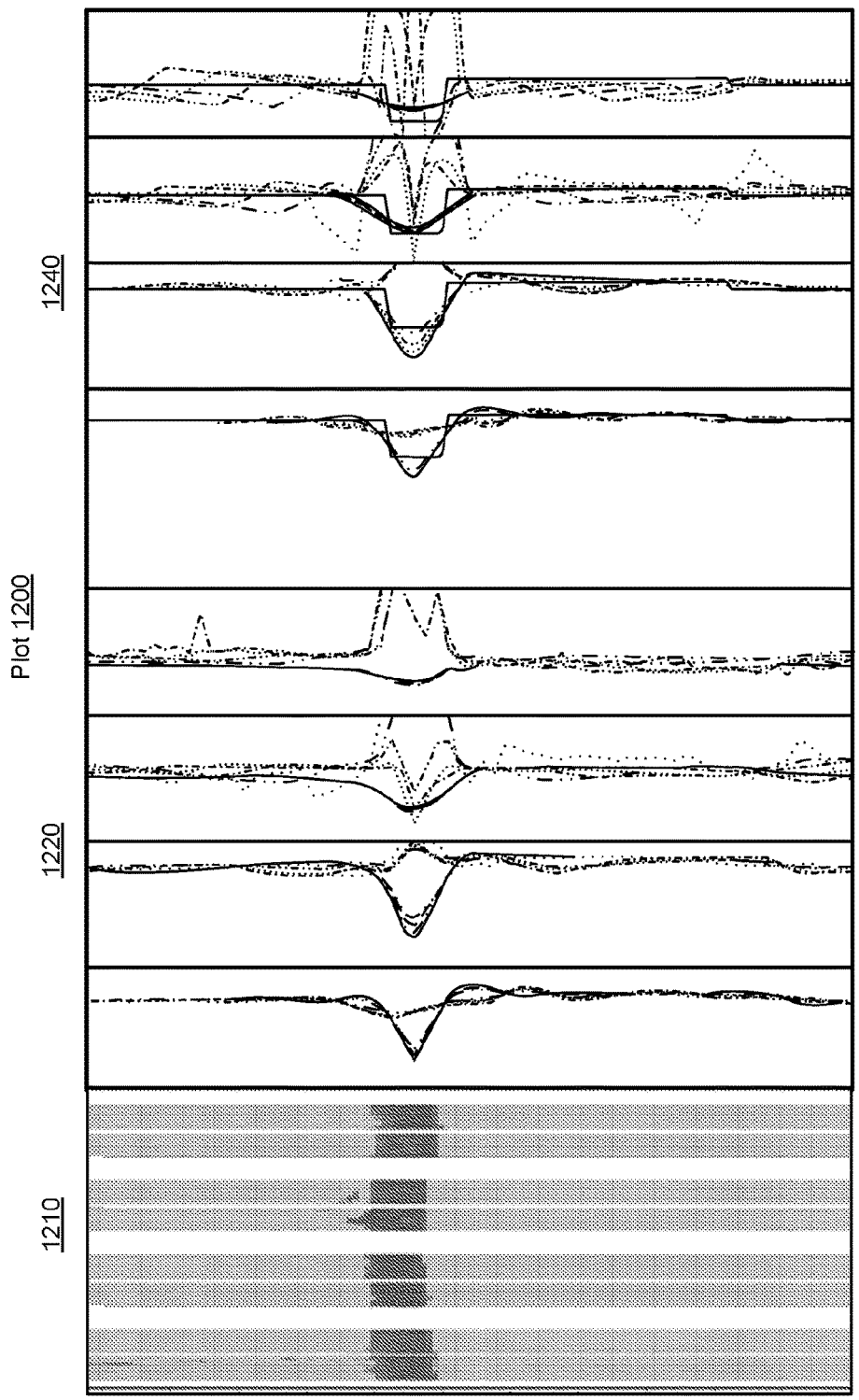
FIG. 12 illustrates an example of a plot.

FIG. 11 shows an example of a plot 1100 and FIG. 12 shows an example of a plot 1200. The plots 1100 and 1200 show examples of quantification. As an example, a detected ash bed may be compatible with about a 1 inch size (e.g., about 2.5 cm), of about a 20 p.u. of water content, a texture parameter of about 2.6 (e.g., representing a value of Archie's exponent "m") and about a 130 ppk water salinity.

As an example, one or more options may be selected for processing of dielectric dispersion log information. As an example, a method can include integration of data from a plurality of sources selected from, for example, available logs (e.g., complementary logs, etc.). As an example, where an imager tool with suitable image quality or a microresistivity with suitable resolution are available, the size of igneous deposits may be fixed based at least in part on such specifications and, for example, dielectric dispersion logs may be used to estimate igneous deposits properties, in term of water content, and potentially texture parameter and water salinity.

As an example, a method can include processing data via an iterative adjustment technique that is based at least in part on one or more formation properties. Such an approach may aim to match log data. As an example, for a given frequency, arrays may be used simultaneously, while the different frequencies are linked through a dispersion model. As an example, electrical anisotropy of one or more non-ash bearing beds may be added to such a dispersion model. As an example, one or more dielectric dispersion logs may be used to estimate size and/or properties of one or more igneous deposits. As an example, a method may include outputting apparent permittivity and conductivity and, for example, igneous deposit water content.

As an example, a method can include neutron porosity log processing. For example, alpha processing based on near detector counts may provide for a desired resolution for a given tool geometry. Neutron log values can vary depending on porosity and, for example, clay content through hydroxyl and clay water contribution and maturity though loss of hydrogens in the organic matter. As an example, raw tool data may be processed and output may be in limestone units.

Referring again to FIG. 10, the track 1010 shows a comparison between a first resolution neutron porosity (TNPH) and a second, higher resolution neutron porosity (HNPO_LIM). As mentioned, FIGS. 10, 11 and 12 show plots 1000, 1100 and 1200, respectively. As mentioned, the plot 1100 shows dielectric dispersion apparent conductivity, comparison between a log and a simulation. Specifically, tracks 1110 show image data, four tracks 1120 present log data while the remaining four tracks 1140 show simulated data. Solid lines that form "block" like shapes represent a model. As mentioned, the plot 1200 shows dielectric dispersion apparent permittivity, comparison between a log and a simulation. Specifically, tracks 1210 show image data, four tracks 1220 present log data while the remaining four tracks 1240 show simulated data. Solid lines that form "block" like shapes represent a model.

As an example, a method may include acquiring data using an ultrasonic imager tool. Such a tool may include components that can scan a circumference and/or a portion of a circumference. As an example, a tool may include a transducer mounted on an ultrasonic rotating sub (USRS). As an example, a transmitter may emit ultrasonic pulses between about 200 kHz and about 700 kHz. As an example, a sensor may measures received ultrasonic waveforms reflected from interfaces within a formation, etc. As an example, an ultrasonic imager tool may provide high angular and vertical resolutions, for example, for detection of channels, etc., as narrow as about 3 cm (e.g., about 1.2 in). As an example, an ultrasonic imager tool may acquire information as to a completion, for example, consider pipe-to-cement bond quality, downhole pipe condition, etc. Such a tool may provide for casing inspection and monitoring applications including, for example, corrosion detection, identification of internal and external damage or deformation, casing thickness analysis for collapse, burst pressure calculations, etc.

As mentioned, a method can include preparing data from one or more sources where such data may relate to one or more possible aspects of an igneous deposit. As an example, such information may be processed to enhance identification and characterization of weathered ash beds.

Figure 13:
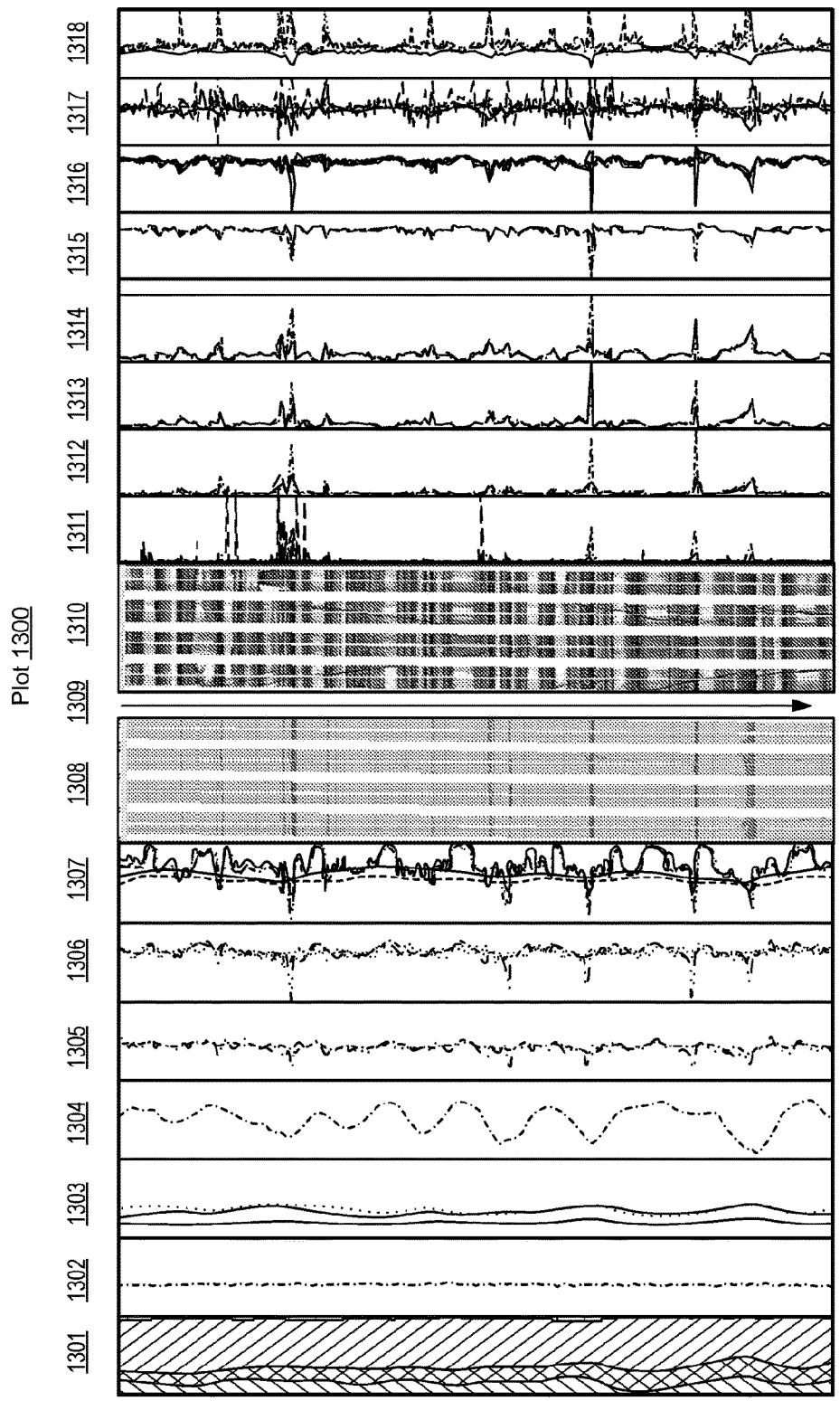
FIG. 13 illustrates an example of a plot.

FIG. 13 shows an example of a plot 1300 that includes integrated high resolution data for igneous deposit detection and characterization where the depth scale is in feet. The plot 1300 includes tracks 1301 to 1318 where track 1309 is a depth direction scale.

In FIG. 13, the track 1301 shows qualitative lithology based on an elemental spectroscopy tool. Optionally, tracks with elemental dry weight relevant for igneous deposit characterization may be added.

In FIG. 13, the track 1302 presents borehole diameter measured by a caliper device. As indicated, the hole is relatively regular in the section, but other sections display washouts. Borehole diameter measured by high resolution caliper provides a measure bed competence. Increased caliper in front of an igneous deposit shows its low consolidation and indicates that fracture may propagate preferentially in the igneous deposits depending on the fracturing fluid composition, but embedment can be a consideration. Caliper data may be analyzed as to mechanical and/or chemical stability of at least a portion of a formation. Caliper data may provide evidence of mechanical stability and/or chemical stability.

In FIG. 13, the track 1303 presents natural gamma ray spectroscopy logs, including potassium, thorium and uranium concentrations. These logs can help with observation of correlations between igneous deposit presence and elemental concentration responses; however, vertical resolution of these logs can impede a clear igneous deposit identification.

In FIG. 13, the track 1304 presents high resolution thermal neutron porosity (HNPO_LIM). Igneous deposit presence does affect the neutron porosity, but not equivocally. An increase of clay content in the non-igneous deposit bearing beds also increases the thermal neutron porosity as seen on the bottom part of the log.

In FIG. 13, the track 1305 presents backscatter and short spacing High Resolution photoelectric factors. In this track, igneous deposits can be identified with a decrease of the PE (PEFB_HR), related to an increase of the porosity and a change in lithology.

In FIG. 13, the track 1306 presents backscatter, short spacing and long spacing High Resolution densities. The backscatter density does mark the presence of igneous deposits (RHBA_HR).

In FIG. 13, the track 1307 presents different resistivity, including high resolution micro-resistivities (B1_HR and B2_HR), image averaged calibrated resistivity (SRES) and induction resistivity (AT90 and AT10) for reference.

In FIG. 13, the tracks 1308 and 1310 are static and dynamic images. Igneous deposits (e.g., ash beds) can be detected, for example, as conductive (dark) or low resistivity beds in the static images.

In FIG. 13, the tracks 1311 to 1314 present the apparent conductivity from dielectric dispersion measurements, from low frequency F0 on the track 1311 up to highest frequency F3 in track 1314. In FIG. 13, the tracks 1315 to 1318 present the apparent permittivity from dielectric dispersion measurements, from high frequency F3 on the track 1315 down to lowest frequency F0 in track 1318. Igneous deposits (e.g., ash beds) can be identified, with different patterns depending on the size and properties of the igneous deposits.

The igneous deposits identified in FIG. 13 tend to be about inch sized (e.g., about a two centimeters to about three centimeters) and do not develop visible washout nor unexplained patterns on resistivity and dielectric logs. While it may seem that the dielectric logs are missing the upper igneous deposit, a closer look at the image shows that the igneous deposit does not cover the full borehole circumference. In such a scenario, the dielectric pad passed in front of the section without igneous deposits. This observation indirectly confirms the image, and this event is likely a local event (e.g., not affecting stimulation).

As shown, data may be acquired and processed to allow for detection of igneous deposits. Geologically, igneous deposits can differ; as such, igneous deposits may be flagged based on one or more of thickness, mineralogy, distance to a target and mechanical strength.

Figure 14:
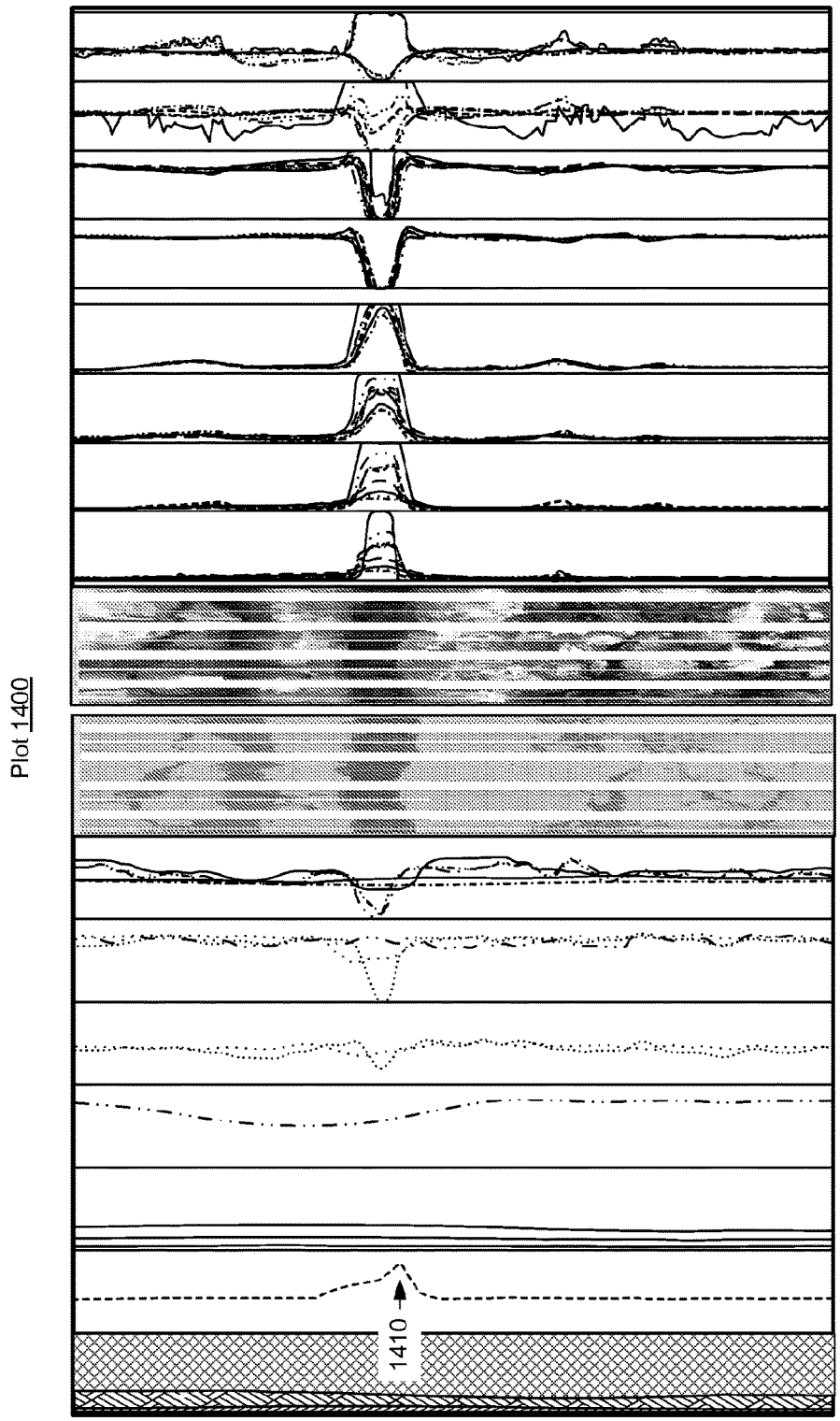
FIG. 14 illustrates examples of plots.

FIG. 14 shows an example plot 1400 that includes an example of an ash bed that has been flagged (e.g., as part of a workflow, etc.). In the example of FIG. 14, the thickness of the flagged ash bed is about 5 cm (e.g., about 2 inches) and it has developed a washout (see, e.g., label 1410 as to the caliper track).

FIG. 14 shows dielectric logs that include patterns that have different origin than shoulder bed effects. Specifically, they are affected by a radial layer of degraded ash bed. Such an ash bed may impact stimulation. As shown in the plot 1400, as to the ash bed, there exists evidence of low resistivity, high conductivity, and a dielectric peak indicating high permittivity. Such evidence may indicate presence of smectite rich ash bed, which may interact with water (e.g., in drilling mud, etc.) and lead to chemical instability. Such a region may be of interest with respect to completion planning, execution, etc. As an example, a completion may be analyzed using a tool (e.g., ultrasonic imager tool), for example, to examine one or more regions where an ash bed may have been detected. While an ash bed is mentioned with respect to FIG. 14, such an approach may provide for detection of one or more other types of igneous deposits.

As an example, igneous deposits may be categorized or ranked in a matrix in a manner that can allow for visualization (e.g., rendering to a display, a printer, etc.) such that a user may examine possible effects on completion and the variability of the igneous deposits.

FIG. 15 shows an example of a table 1500, which includes an example of various matrix criteria that may be implemented to assess individual igneous deposits and make recommendations, for example, as to completion fluids and location of completion stages, which may act to mitigate possible hazards associated with one or more of the individual igneous deposits. As an example, a method can include making recommendations, for example, to help mitigate one or more hazards associated with one or more igneous deposits.

As an example, a method can include receiving data for a geologic environment, the data acquired via a plurality of different measurement techniques; analyzing the data as to the presence of at least one igneous deposit; and classifying at least a portion of the geologic environment based at least in part on the analyzing. In such an example, at least one of the at least one igneous deposit can include a thickness less than approximately 10 cm, a thickness less than approximately 5 cm and/or a thickness less than approximately 2.5 cm. As an example, at least one of the plurality of different measurement techniques may acquire raw data with a resolution less than approximately 10 cm (e.g., or less than approximately 5 cm, or less than approximately 2.5 cm, etc.). As an example, a method can include processing raw data.

As an example, a plurality of different measurement techniques can include at least one technique selected from a group of micro-resistivity techniques, density and photoelectric factor or index techniques, image calibration techniques, dielectric and conductivity dispersion techniques, neutron porosity techniques, and ultrasound techniques (e.g., ultrasonic techniques).

As an example, a method can include flagging a portion of a geologic environment based at least in part on the presence of an igneous deposit and, for example, adjusting a completion plan based at least in part on the flagging.

As an example, an igneous deposit may be or include a weathered volcanic ash bed. As an example, an igneous deposit can include bentonite.

As an example, a method can include classifying that includes accessing at least one criterion. For example, consider accessing at least one completion-related criterion and then classifying (e.g., based at least in part on one or more criteria). As an example, a criterion can include at least one member selected from a group of thickness criteria, mechanical stability criteria, chemical stability criteria, and mineralogical criteria; and/or a distance to a target criterion where the target may be specified as a location in a geologic environment.

As an example, a method can include acquiring data via at least one of a plurality of different measurement techniques. Such a method may include processing such data, optionally in a manner to enhance detection of an igneous deposit or igneous deposits.

As an example, a system can include a processor; memory accessibly by the processor; one or more modules stored in the memory where the one or more modules include processor-executable instructions to instruct the system and where the instructions include instructions to receive data for a geologic environment, the data acquired via a plurality of different measurement techniques; analyze the data as to the presence of at least one igneous deposit; and classify at least a portion of the geologic environment based at least in part on the analysis of the data. In such an example, at least one of the plurality of different measurement techniques may acquire raw data with a resolution less than approximately 10 cm (e.g., and/or 5 cm and/or 2.5 cm) and such a system may include instructions to process the raw data.

As an example, one or more computer-readable media can include processor-executable instructions where the processor-executable instructions include instructions to instruct a computer to receive data for a geologic environment, the data acquired via a plurality of different measurement techniques; analyze the data as to the presence of at least one igneous deposit; and classify at least a portion of the geologic environment based at least in part on the analysis of the data. In such an example at least one of the plurality of different measurement techniques may acquire raw data with a resolution less than approximately 10 cm (e.g., and/or 5 cm and/or 2.5 cm) and the instructions may include instructions to process the raw data.

As an example, one or more computer-readable media may include processor-executable instructions to flag a portion of a geologic environment based at least in part on presence of an igneous deposit and instructions to adjust a completion plan based at least in part on the flagged portion of the geologic environment.

As mentioned, a method can include combining NMR, sonic, and lithology scanner wireline logs to develop completion logs that include geologic meaning. In such an example, geologic meaning embedded within rocks can allow for predictive modeling of a completion, for example, in a near and/or a far wellbore environment.

Figure 16:
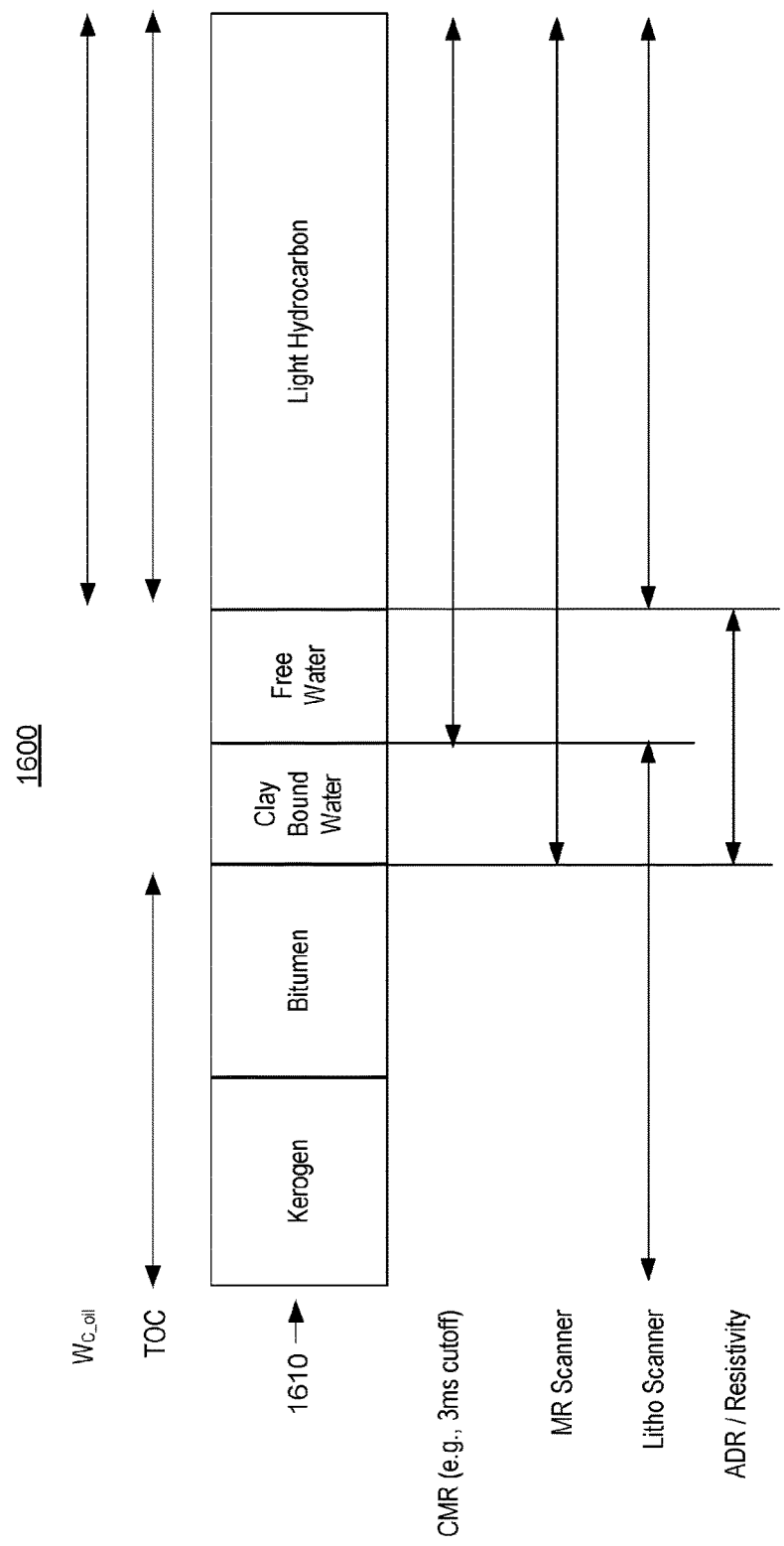
FIG. 16 illustrates an example of a compositional model of materials with respect to various measurement techniques.

FIG. 16 shows an example of a petrophysical model for tight oil reservoirs and a response of various logging tools to the different constituents. The model 1610 shows constituents of a tight oil reservoir. Above the model 1610, FIG. 16 shows that $W_{C\text{-}oil}$ includes organic carbon in light oil (both bound and movable), while TOC includes organic carbon in light oil as well as kerogen and bitumen. The weight fraction of carbon associated with light oil, $W_{C\text{-}oil}$, may be computed as the weight fraction of light oil in the formation multiplied by the fractional weight of carbon in oil, which may be about 0.82 to about 0.86 grams C per gram oil.

In FIG. 16, below the model 1610, various logging tool ranges are illustrated to show which constituents each tool may be expected to be responsive. As an example, a combinable magnetic resonance (CMR) tool or other type of magnetic resonance (MR) tool may be utilized. As an example, a CMR tool may be a tool that includes one or more features of a tool such as, for example, the CMR-Plus™ combinable magnetic resonance tool marketed by Schlumberger Limited (Houston, Tex.).

As an example, a method can include acquiring borehole NMR data for T1 (longitudinal relaxation or spin-lattice relaxation) and/or T2 (transverse relaxation or spin-spin relaxation). As an example, deterioration of an NMR signal can be analyzed in terms of separate processes where each process can include its own time constant. For example, one process, associated with T1, can be responsible for loss of signal intensity while another process, associated with T2, can be responsible for broadening of a signal. Stated more formally, T1 can be the time constant for the physical processes responsible for the relaxation of the components of the nuclear spin magnetization vector M parallel to the external magnetic field, B0 and T2 relaxation can affect the components of M perpendicular to B0. Relaxation can depend on temperature and, for example, there can also be a pressure dependence as to relaxation, for example, in relationship to an environment (e.g., a pore space, etc.).

As an example, NMR data may be or include hydrogen NMR data as may be associated with one or more constituents that include hydrogen. As an example, consider NMR data that can be analyzed as to different populations of protons. For example, consider hydroxyls from clay (e.g., $T2<\sim0.1$ ms, $\sim10<T1/T2<\sim100$), water ($T1/T2\sim2$), and in certain situations organic matter ($10<T1/T2<\sim100$). As an example, methane may be distinguished with a particular T1/T2 ratio. NMR data may be analyzed according to a model such as, for example, a pore model that can include a bulk volume with a volume fraction $f_b$ and a surface layer with a volume fraction $f_s$ where, for example, $f_b+f_s\sim1$. In such an example, due to molecular diffusion, an exchange can exist between the surface and bulk volumes, which may be characterized by an exchange time. As an example, NMR data may provide information for one or more fluid properties.

As to methane, T1 and T2 can increase with pressure and, for example, be in a range of about 500 ms to about 5000 ms for methane pressure between about 25 bar up to about 200 bar. As an example, at low temperature (e.g., about 100K), the T1/T2 ratio of methane can increase considerably (e.g., to be ~10 or more), for example, due to anisotropic rotational motions at the surface, with the existence of two correlation times. In such an example, T1 will then be sensitive to the fast correlation time, while T2 to the slow one. In a partially saturated porous media, relaxation of methane still occurs, although weaker despite water wetting the surface.

A MR tool can provide for acquiring data as to nuclear magnetic properties of one or more constituents in a formation. Such an approach may utilize one or more Larmor frequencies as may be determined in part via one or more gyromagnetic ratios (e.g., H-1 of 42.58, P-31 of 17.24, etc.). As an example, an NMR log can include T1 and/or T2 data at various depths. As an example, by running an NMR tool with different acquisition parameters, information germane to hydrocarbon typing, diffusion, etc., may be acquired.

As an example, NMR measurements obtained via an MR tool may be analyzed as to T2 information. As an example, NMR data may be analyzed to extract lithology-independent formation porosity and, for example, to separate T2 distributions for fluids such as, for example, brine and oil. As an example, a hydrocarbon-corrected bound-water volume and permeability may be computed from T2 distributions.

In the example model 1610 of FIG. 16, as to the CMR tool, an example cutoff is given of about 3 ms; noting that one or more other cutoff values can be used. For example, cutoff values of about 2.9 ms or about 3.1 ms can be used. As an example, a range may be from about 0 ms to about several milliseconds.

As an example, a T2 distribution above a value such as about 3 ms can be used to quantify light oil and free water contributions. This is because the other components of the T2 distribution, namely the bitumen and the clay bound water, have relaxation times less than that value. As an example, an amount of clay bound water can be estimated as a percentage of the weight of the clay content determined using a tool such as a gamma ray spectroscopy tool. The total water which includes clay bound water and free water may be determined using a dielectric dispersion logging tool. As an example, quantity of light oil may be calculated from a difference between NMR T2 distributions above a value (e.g., about 3 ms) and a free-water volume derived from one or more other tools. As an example, a TOC can be measured using a gamma ray spectroscopy tool. As an example, carbon saturation index (CSI) and reservoir producability index (RPI) can be calculated using the light oil and TOC quantities.

As an example, NMR data can be utilized to determine pore information. For example, T2 decay associated with a single pore size in water-saturated rocks tends to be proportional to the pore size. As an example, measured T2 decay can be a sum of various types of T2 decays (e.g., associated with different types of pore environments) because reservoir rocks can include a distribution of pore sizes and can include more than one fluid type. For example, a CMPG T2 spin-echo train can include a distribution of T2 decays, rather than a single T2 decay. In such an example, exponential decay may be described as follows:

$$M(t) = \sum M_i(0)e^{-\frac{t}{T2_i}}$$

where M(t)=measured magnetization at t; $M_i(0)$=initial magnetization from the ith component of relaxation; and $T2_i$=decay constant of the i th component of transverse relaxation. The summation is over the entire sample (e.g., pores of various sizes and/or shapes and different types of fluid).

Decay can be multi-exponential for a porous medium that includes pores of different sizes and one or more wetting phases. As an example, surface relaxation can dominate when a short inter-echo spacing is used and a formation is brine saturated. Under such a condition, T2 tends to be directly proportional to pore size. When pores are assumed to have similar geometric shape, the largest pores tend to have the lowest surface/volume (S/V) and, thus, the longest T2. Medium-size pores have smaller S/V, yielding shorter T2 values. The smallest pores have the highest S/V and the shortest T2 values. As an example, an equation such as the following approximate equation may be utilized to estimate S/V (e.g., where in the exponent (1/T2) is replaced with an S/V term).

$$M(t) = \sum M_i(0)e^{-\rho\left(\frac{S}{V}\right)_i t}$$

As an example, pores unresolved by optical microscopy may exhibit a threshold of about 85 milliseconds or less for the NMR longitudinal relaxation time constant (T1), for example, which can correspond to an optical resolution limit of 5 microns diameter.

As an example, NMR data may be analyzed to determine surface/volume values and/or volume/surface values of pores. For example, T1 and/or T2 information from NMR data may be analyzed to determine one or more characteristics of pores, which may include surface information, volume information or a combination of surface and volume information (e.g., S/V and/or V/S).

As to determination of biogenic and diagenetic mineralogy, these may be based at least in part on detrital and diagenetic indices. As an example, a method may include calculating a detrital index and/or a diagenetic index. Such a method may aim to determine a proportion of depositional mineralogy versus diagenetic mineralogy. As an example, a sample may be analyzed with respect to a percentage of biotite, muscovite, orthoclase, quartz, dolomite, pyrite, anhydrite, evaporates, ankerite and calcite; noting that various minerals may be provided in an equation or equations as examples. For example, one or more other minerals may be used to form equations where normalization may be with respect to quartz for a detrital index equation and for calcite with respect to a diagenetic index equation. As an example, an index may be inverted. In such an example, quartz and calcite may still act to "weight" or "normalize" the index values calculated via such equations. As an example, an index or indexes may be used to characterize a portion of a geologic environment.

As mentioned, rocks may be characterized by types such as, for example, sedimentary rocks like sandstone and limestone (e.g., formed at the Earth's surface through deposition of sediments derived from weathered rocks, biogenic activity or precipitation from solution). As an example, a biogenic substance can be defined as a substance produced by life processes. For example, it may be either constituents, or secretions, of plants and/or animals. A biogenic substance may be a biomolecule or biomolecules.

As an example, an earthen formation can include layers of media where elasticity of the media may be isotropic, anisotropic or isotropic in certain aspects and anisotropic in others. As an example, crustal rock may be anisotropic yet transversely isotropic "TI" (e.g., locally polar anisotropic). Knowledge of isotropy, anisotropy, etc. can assist with, for example, planning and execution of exploration and development operations of a reservoir or reservoirs within a formation.

As an example of parameters that can characterize anisotropy of media (e.g., seismic anisotropy), consider the Thomsen parameters ε, δ and γ (see, e.g., Thomsen, "Weak elastic anisotropy", Geophysics, Vol. 51, No. 10, pp. 1954-1966, October 1986). The Thomsen parameter δ can describe offset effects (e.g., short offset). As to the Thomsen parameter ε, it can describe offset effects (e.g., a long offset) and can relate to a difference between vertical and horizontal compressional waves (e.g., P or P-wave or quasi compressional wave qP or qP-wave). As to the Thomsen parameter γ, it can describe a shear wave effect. For example, consider an effect as to a horizontal shear wave with horizontal polarization to a vertical shear wave. The Thomsen parameters ε and γ may be estimated from wave data while estimation of the Thomsen parameter δ involves access to additional information. As noted by Thomsen (1986), the parameter δ controls most anisotropic phenomena of a medium of interest in geophysics, some phenomena of which are non-negligible even when anisotropy is considered to be weak.

The Thomsen parameter γ may be represented as follows using terms of an elastic modulus matrix:

$$\gamma \equiv \frac{C_{66} - C_{44}}{2C_{44}}$$

Referring again to the example method 600 of FIG. 6, a base model can be output based on a combination of data from three wireline logs: sonic, NMR, and gamma ray spectroscopy. The method 600 of FIG. 6 can be a workflow. As an example, highlights can be given as to an associated primary function of each log in building information to construct a predictive model. For example, gamma ray spectroscopy data can be utilized for mineralogic classification. The detrital and diagenetic indices can be used to further develop biogenic vs. diagenetic minerals within rock. Mineral classification can then combined with volume/surface ratio (e.g., or surface/volume ratio, etc.) obtained from NMR.

Figure 17:
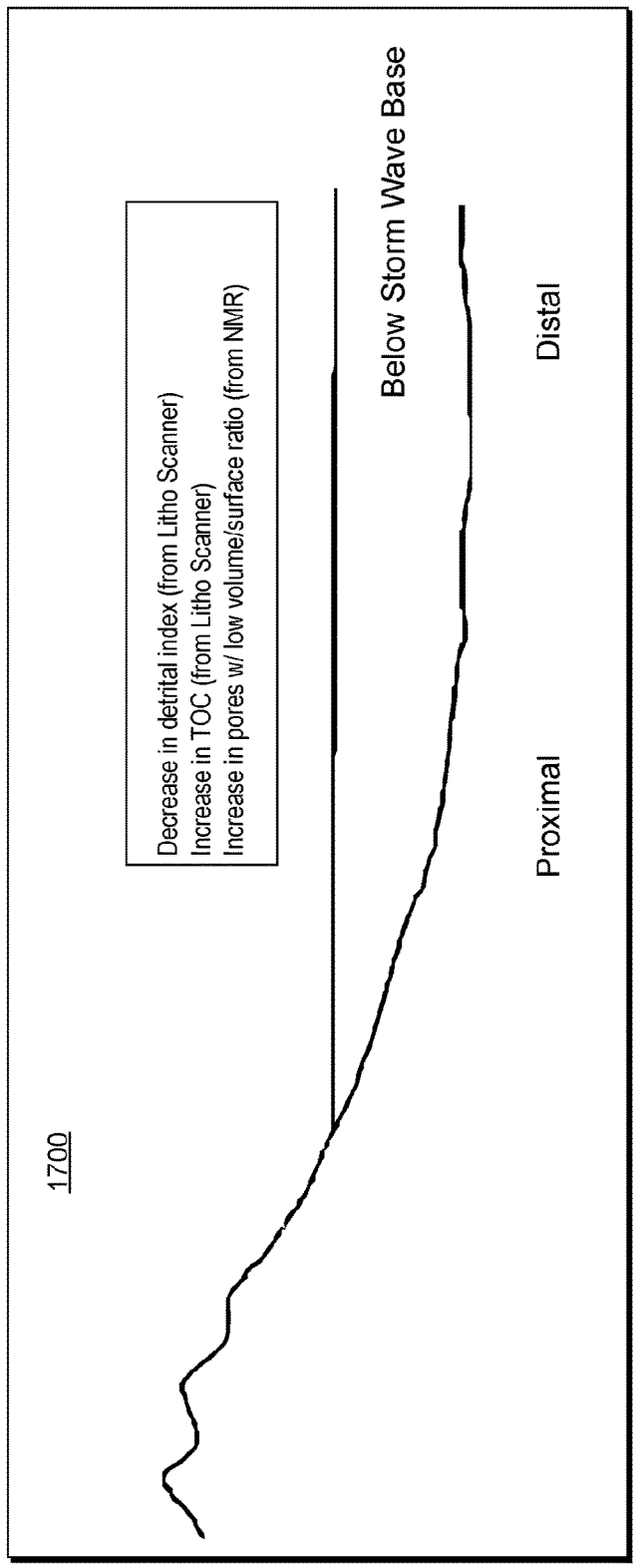
FIG. 17 illustrates an example of a graphic of a geologic environment.

The approach of FIG. 6 can provide a geologic classification for rock that can define the rock as proximal or distal depositional environment relative to the surrounding rock (see, e.g., FIG. 17).

As an example, sonic logs can be used to obtain the Thomsen's gamma, which is a measure of anisotropy (e.g., or one or more other Thomsen parameters, etc.). Increasing diagenetic cement, determined from gamma ray spectroscopy data may indicate an increase in isotropic behavior of the rock. Such information may be utilized for a completion model. Combining mechanical classification and geological classification can allow for generation of a predictive completion model that produces information about a current well-bore and also about a far-well bore environment (e.g., within a neighborhood of the current well-bore).

FIG. 17 shows an example of a model of a basin showing changes in wireline response as sedimenation moves from a proximal to distal depositional environment.

Mineralogic Classification

Mineralogic classification can include analyzing gamma ray spectroscopy data to analyze stratigraphy. Such an approach can allow detrital mineralogy to be distinguished from diagenetic mineralogy. This has stratigraphic implications for modeling within a basin and is a geologic constraint. It is also a basis for combinations with NMR and sonic logs.

Example formulas can be:

Detrital_Index=muscovite+orthoclase+biotite

Diagenetic_Index=dolomite+ankerite+siderite+anhydrite+evaporate+pyrite

Such formulas can be used with XRD, FTIR or other mineralogic data in addition to gamma ray spectroscopy data. In an effort to further differentiate mineralogy in complex systems, additional formulas may be utilized that subdivide mineralogy for biogenic components as well as distinguishing the mineralogy for mechanical properties.

Nondetrital_quartz=Total_quartz−g*Detrital_index

Nondetrital_calcite=Total_calcite−h*Diagenetic_index

As an example, a method can include differentiating quartz that is detrital from quartz that is diagenetic or biogenic. The above formulas help to differentiate the different contributions of quartz and calcite. For example, total_quartz can be obtained from gamma ray spectroscopy data. Detrital_index is a proxy for the amount of quartz that originates as sand- or silt-sized particles from outside the basin. This value could be adjusted based on one or more known factors in a basin (e.g., it is weathered quartzite which would drive the quartz ratio up relative to other detrital minerals) by adding the variable "g", for example, a variable that can be adjusted manually based on known parameters or set to 1 (e.g., or automatically based on information). Nondetrital quartz in this case includes a wide range of nondetrital sources, including biogenic, volcanic, and authigenic cement. This is an example of a qualitative approach to estimating diagenetic quartz in the rock as there is an assumption that higher amounts of detrital quartz correlate to the higher detrital_index. There can still be amounts of detrital quartz mixed in with low detrital_index. However, this can provide an example workflow a value for calculating changes in quartz and calcite content that are useful for mechanical properties and assuming no discontinuities in the surface, can be consistent with gradual changes in the depositional environment. As an example, such a value can then be used to look at total diagenetic changes within a rock, for example, by using the following generalized formula:

Diagenetic_mineralogy=Diagenetic index+Nondetrital_quartz+Nondetrital_calcite

The diagenetic mineralogy calculated by the diagenetic_index does not include quartz or calcite which can be a component of a rock. Including these minerals into the total calculation of diagenetic minerals, increases the diagenetic mineralogy which in turn increases the anisotropy. To account for the mechanical changes that can be associated with diagenesis, a third formula is introduced:

Mechanical_mineralogy=Detrital_Index−Diagenetic_Mineralogy

Figure 18:
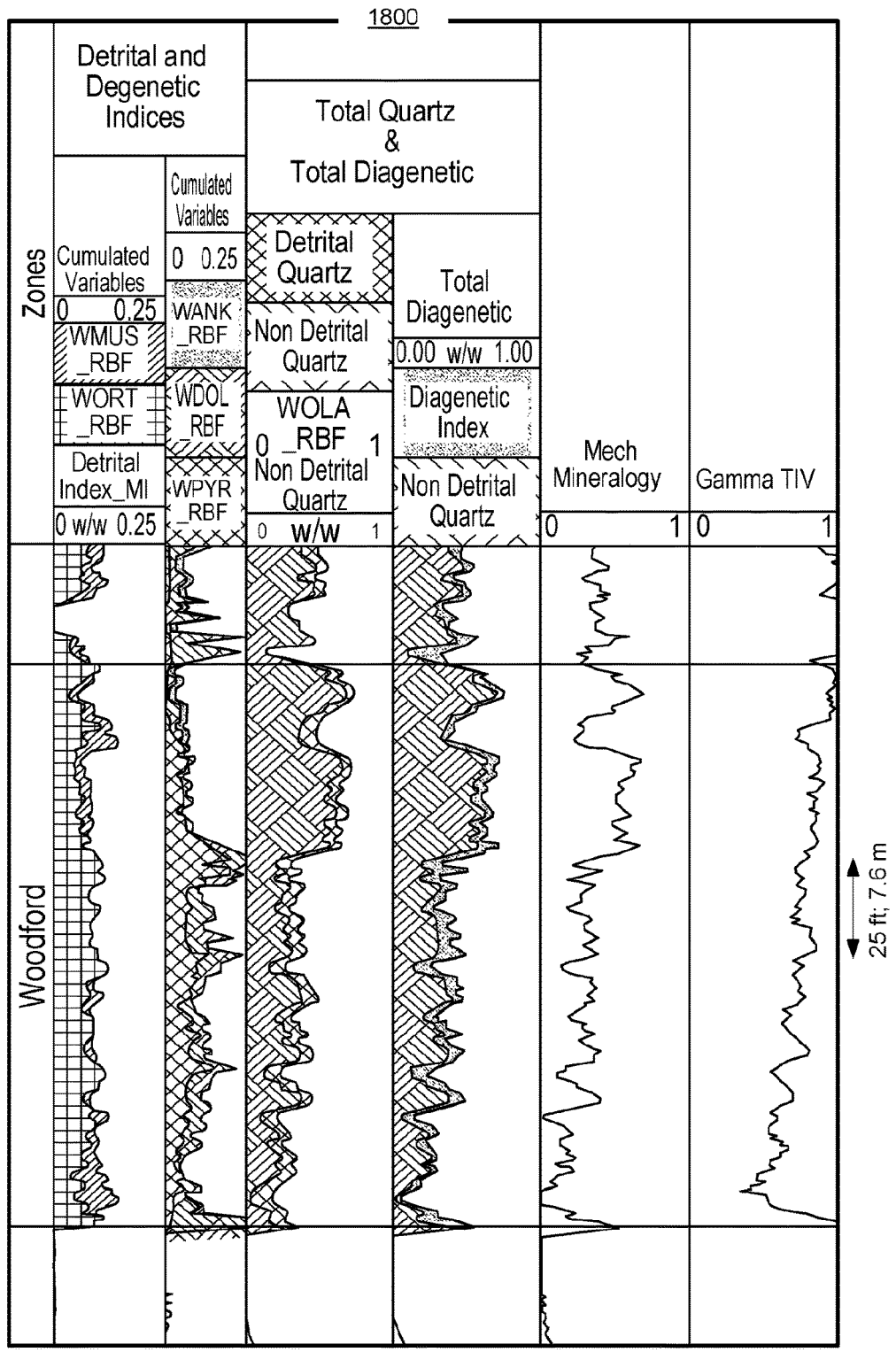
FIG. 18 illustrates examples of plots.

The relationship of the various calculations to the mechanical mineralogy can be seen in FIG. 18, which shows an example of the mechanical mineralogy. The first track shows the Woodford zone, the second track the detrital index as the sum of muscovite and orthoclase. The third track shows the diagenetic index as the sum of all diagenetic minerals like pyrite, siderite, dolomite, evaporite, ankerite and anhydrite. The forth track shows the total quartz, as the sum of detrital index and non-detrital quartz. The fifth track shows the diagenetic mineralogy as the sum of diagenetic index and nondetrital_qtz. The sixth track shows the mechanical mineralogy and the seventh the gamma_TIV. As shown in FIG. 18, mechanical mineralogy and gamma_TIV are anti-correlated.

Mechanical Classification

The mechanical classification can combine the diagenetic mineralogy and the Thomsen's gamma, derived from sonic log data (see, e.g., FIG. 18). This classification can be used for building predictable completion logs. Completion logs tend to be point measurements for a given well, whereas building completion logs from mineralogic data as well as sonic, allows the completion log to contain geologic context that can used to predict the mechanical properties throughout the basin.

Figure 19:
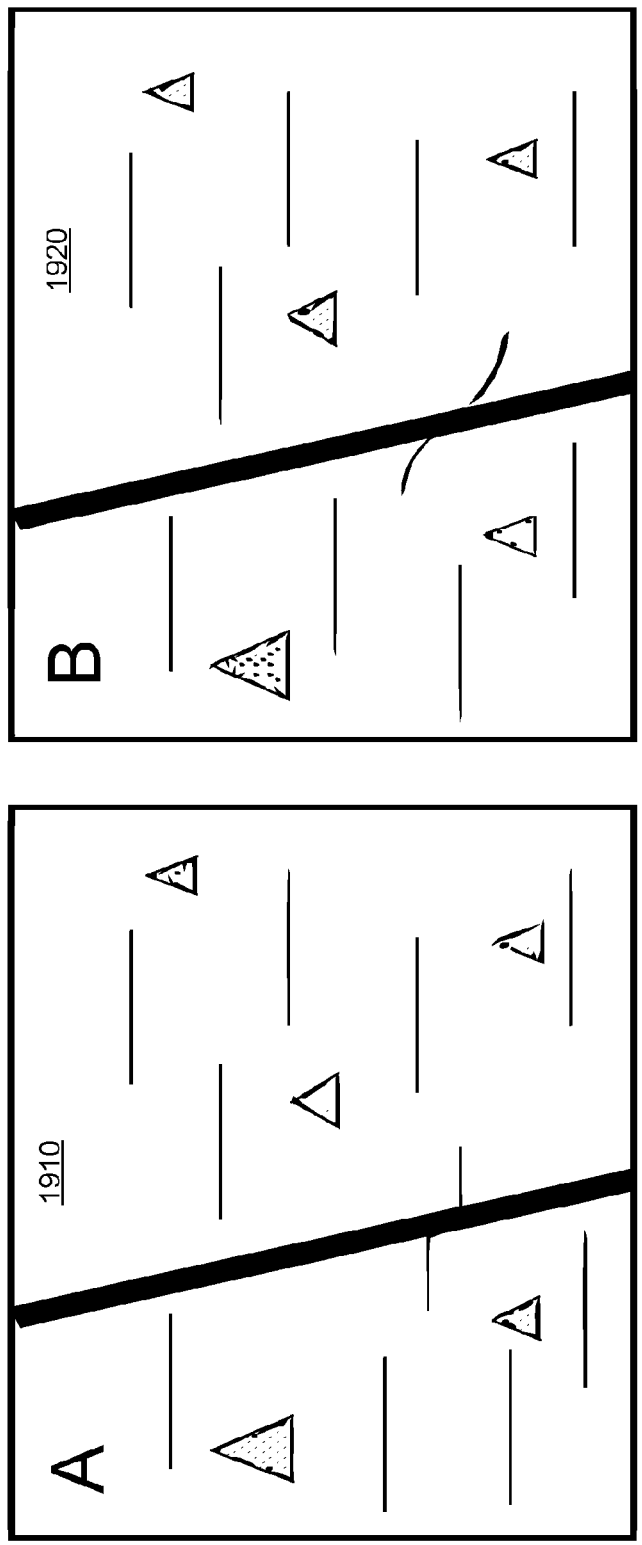
FIG. 19 illustrates examples of graphics of rock samples.

Mechanical classification can be concerned with the behavior of rocks at a microscopic scale. In FIG. 19, graphics 1910 and 1920 correspond to two rock samples (A and B) as observed with similar mineralogy. The solid thick strip represents a fracture that can be either natural or induced. The organic strip that is intersected by the fracture behaves differently between the sample A and the sample B due to the amount of diagenetic cement that is contained within the sample. Thus, ascertaining the origin of the mineralogy can provide context for the observed Thomsen's gamma measurements.

Specifically, FIG. 19 shows two samples with similar depositional mineralogy. Lines in the graphics 1910 and 1920 represent organic particles and triangles in the graphics 1910 and 1920 represent detrital minerals. The solid thick strip represents a fracture that can be, for example, natural and/or induced. In the graphic 1910, for sample A, the organic particle intersected by the fracture is split; whereas, in the graphic 1920, for sample B, the organic particle intersected by the fracture is bent. The difference between the samples A and B is the amount of diagenetic cement that formed in the matrix and altered the mechanical properties of the rock. As an example, one or more other components may also alter the mechanical properties of rocks such as fecal pellets, clay type, etc.

Figure 20:
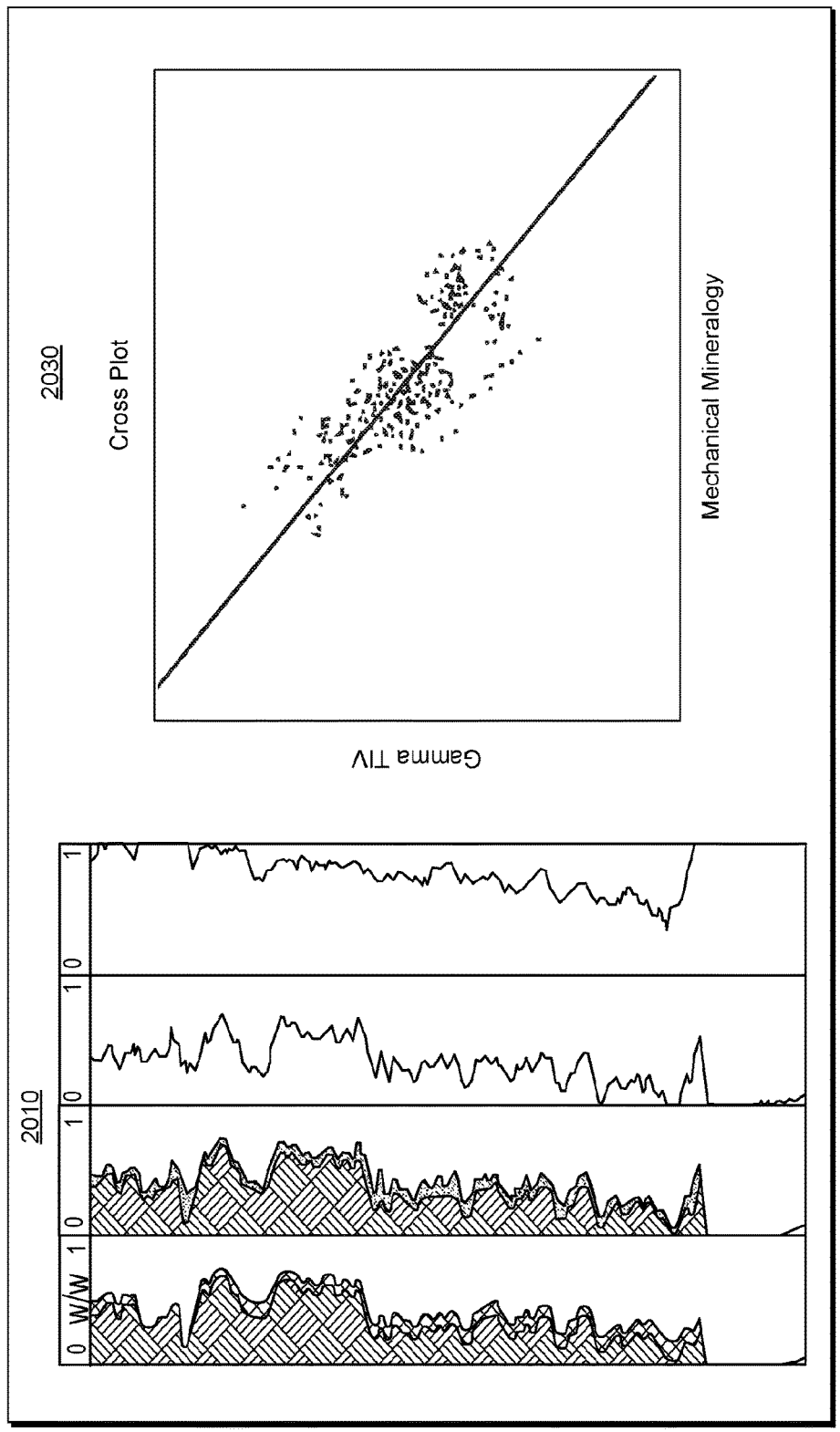
FIG. 20 illustrates examples of plots.

Thomsen's gamma is a measure of anisotropy and can show a strong anti-correlation with the calculated mechanical mineralogy from gamma ray spectroscopy data. FIG. 20 includes a cross plot 2030 between Thomsen's gamma and mechanical mineralogy from the Woodford shale (see, e.g., the tracks 2010). In general, increasing diagenesis mineralogy leads to increasing isotropic behavior. However, increasing detrital index or clay-rich units correlates to higher degrees of anisotropy at deposition. Therefore, combining the diagenetic and detrital indices with the Thomsen's gamma can allow for a mechanical and a stratigraphic interpretation.

More specifically, FIG. 20 shows a relationship of different quartz mineralogies with depth relative to Thomsen's gamma represented as Gamma TIV. In track 1, nondetrital quartz and detrital quartz (see also, e.g., FIG. 18) are shown where the proportion of detrital quartz increases relative to nondetrital quartz at the base of the measured interval. In track 2, nondetrital quartz and diagenetic index are shown (see also, e.g., FIG. 18) where nondetrital quartz increases relative to diagenetic index towards the top of the Woodford and where the nondetrital quartz is increasingly biogenic. Thomson's gamma is shown in track 4 where it is closer to 1 or anisotropic in the base of the Woodford where quartz is predominantly detrital and diagenetic mineralogy is low. As shown, Thomsen's gamma approaches 0 (isotropic) towards the top of the Woodford with increasing diagenetic quartz and increasing biogenic quartz. As indicated, Thomsen's gamma is anti-correlated with mechanical mineralogy.

Geologic Classification

As an example, geologic classification can combines NMR interpretations with the mineral indices determined in the mineralogic classification. As mentioned, NMR can be used to calculate the Volume/Surface (V/S) ratio or pore aspect ratio of the pore and compare that to the total size of the pores. Organic-hosted porosity tends to be smaller but enlarge with increasing maturation. Therefore the V/S ratio (e.g., or S/V ratio, etc.) can be a function both of the type of porosity but also maturation. On its own, the V/S ratio can not necessarily distinguish depositional environments. However, as an example, when combined with the mineral indices that are sensitive to depositional mineralogy and diagenetic changes, it can be used to extract depositional changes.

Figure 21:
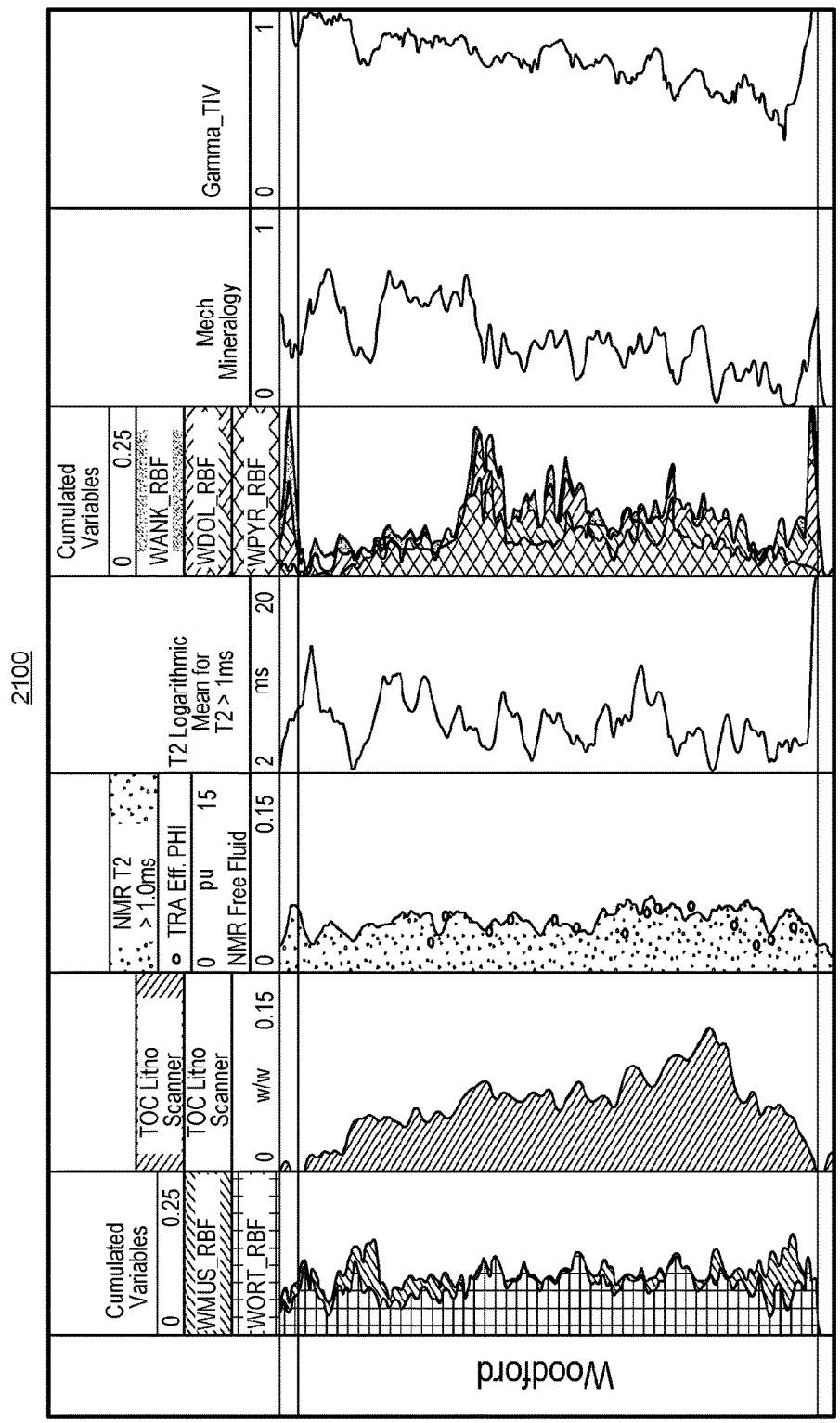
FIG. 21 illustrates examples of plots.

FIG. 21 shows a multitrack plot 2100 for the base of the Woodford as including a change in the orthoclase/muscovite ratio (Track 1) with decreasing depth that corresponds to a change in the total organic carbon (Track 2). As these are detrital indicators, this mineralogic change is indicative of a change in the depositional environment with time. However, the very base of the Woodford section shows an increase in diagenetic mineralogy that is largely driven by dolomite (Track 4). This drives changes in the mechanical mineralogy (Track 6), which is calculated from Gamma ray spectroscopy, as well as Gamma TIV (Track 7), which is determined from sonic.

More specifically, FIG. 21 shows examples of synthesis of several logs as to the integration of NMR, sonic, and gamma ray spectroscopy data to highlight depositional and diagenetic changes within a basin and their impact on mechanical properties. The following tracks are included in the multitrack plot 2100: Track 1—Detrital Mineralogy (from gamma ray spectroscopy); Track 2—TOC (from gamma ray spectroscopy); Track 3—Free Fluid (light hydrocarbon and pore water); Track 4—Logarithmic Mean of T2 distribution for T2 containing Free Fluid, proportional to Volume to Surface Ratio; Track 5—Diagenetic Mineralogy (from gamma ray spectroscopy); Track 6—Mechanical Mineralogy; and Track 7—Gamma_TIV (from sonic).

Combined Interpretation

As an example, data can be combined such that they can be used to predict behavior away from a well bore, for example, for drilling that may be planned and performed. As an example, various options can be available for combined interpretation. An unguided classification can be used to group similar log units. These similar log units can be assigned a generic class that can then be applied to additional wells. An example of an alternative approach can be a semi-guided classification system in which geologic knowledge is used to map stratigraphic units and then apply the log parameters to subsequent wells.

Figure 22:
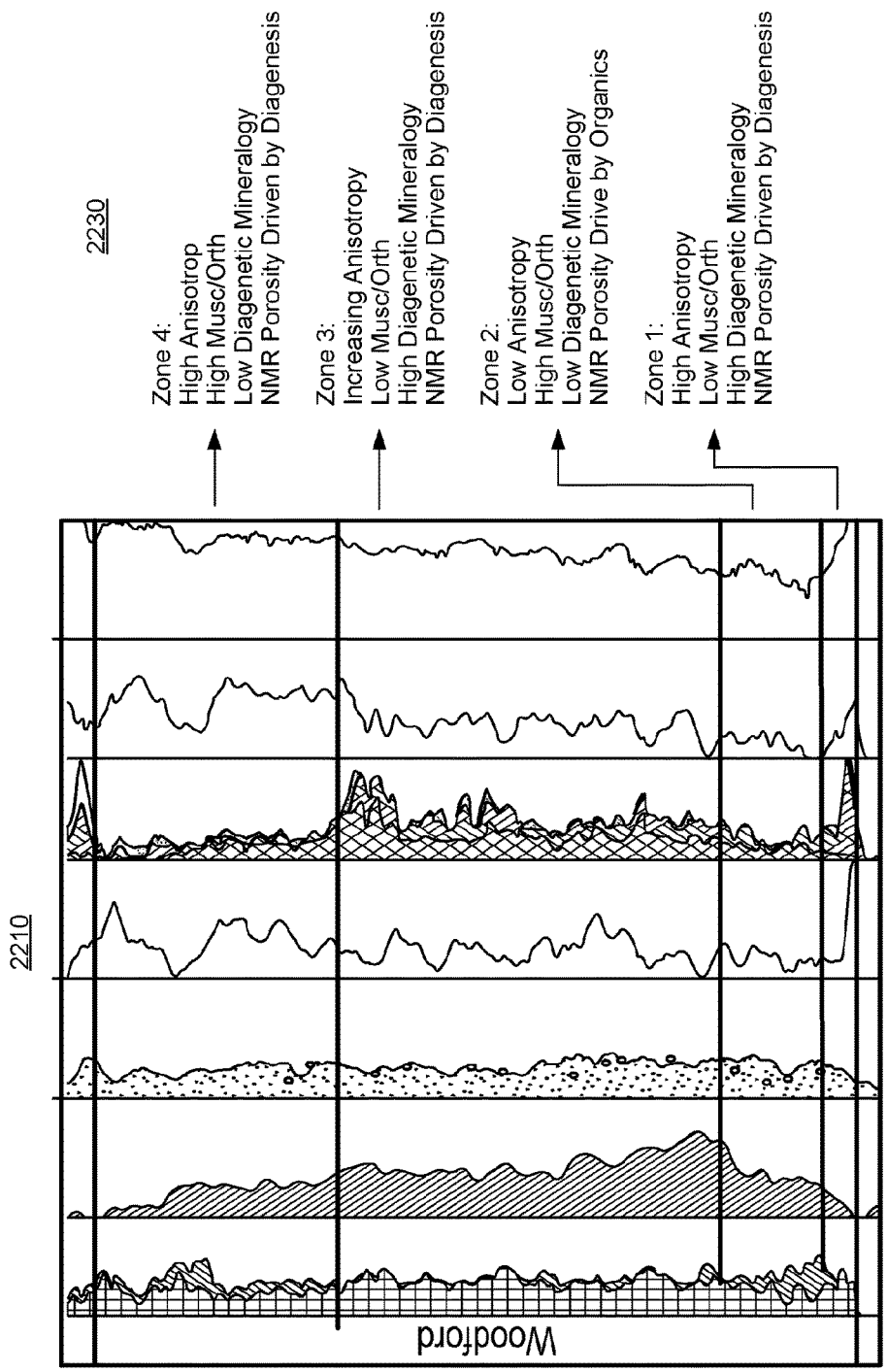
FIG. 22 illustrates examples of plots and examples of zone characterized by various features of rock.

FIG. 22 shows a guided classification 2230 based on the data 2210, which is also shown in FIG. 21. The rationale used for each zone is attached to the subunit. In fact, several of these zones can be subdivided further by providing cutoffs based on a number of criteria such as TOC, diagenetic mineralogy, gamma TIV. For example, Zone 3 shows increasing gamma TIV towards the top of the unit while TOC decreases. Either of these cutoffs in a semi-guided classification would have produced additional subunits that would have geologic and completion meaning.

More specifically, FIG. 22 shows results of a classification of synthesized data from FIG. 21. As an example, these zones can be amenable to further subdivision, for example, by using semi-guided and/or unguided numerical cutoffs.

In the example of FIG. 22, information for four zones is shown. Such information may be utilized to plan, to perform, etc. one or more operations, which can include field operations. As an example, one or more of a drilling operation, a completions operation, an injection operation, a stimulation treatment operation, etc. may be planned and/or performed using a model such as a model output by a method such as, for example, the method 600 of FIG. 6.

As an example, a method can include receiving data for a geologic environment where the data includes sonic data, NMR data and gamma ray spectroscopy data; analyzing the data; and outputting a model of at least a portion of the geologic environment based at least in part on the analyzing. In such an example, the model can include zones. For example, zones may be organizes with respect to depth in a geologic environment. As an example, zones can include rock characteristics that are based at least in part on one or more of the sonic data, the NMR data and the gamma ray spectroscopy data.

As an example, a method can include determining at least one pore characteristic of geologic environment, for example, where the at least one pore characteristic includes a surface to volume ratio or a volume to surface ratio based at least in part on a portion of the NMR data (e.g., spin-spin relaxation data, etc.).

As an example, a method can include determining at least one value for the Thomsen gamma parameter, for example, where the at least one value is based at least in part on at least a portion of sonic data.

As an example, a method can include determining at least one index value, for example, where the at least one index value is based at least in part on gamma ray spectroscopy data.

As an example, a method can include receiving data that are acquired along a span of a single, common bore in the geologic environment.

As an example, a method can include applying a model to a region of the geologic environment that differs from an acquisition region of data utilized to build the model (e.g., generate the model). In such an example, the model may correspond to a model built using data that were acquired along a span of a single, common bore in the geologic environment.

A system can include a processor; memory accessibly by the processor; one or more modules stored in the memory where the one or more modules include processor-executable instructions to instruct the system and where the instructions include instructions to receive data for a geologic environment where the data includes sonic data, NMR data and gamma ray spectroscopy data; analyze the data; and output a model of at least a portion of the geologic environment based at least in part on an analysis of the data.

As an example, one or more computer-readable media can include processor-executable instructions where the processor-executable instructions include instructions to instruct a computer to receive data for a geologic environment where the data includes sonic data, NMR data and gamma ray spectroscopy data; analyze the data; and output a model of at least a portion of the geologic environment based at least in part on an analysis of the data.

As an example, a method can include receiving data for a geologic environment, the data acquired via a plurality of different measurement techniques; analyzing the data; and classifying at least a portion of the geologic environment based at least in part on the analyzing.

Figure 23:
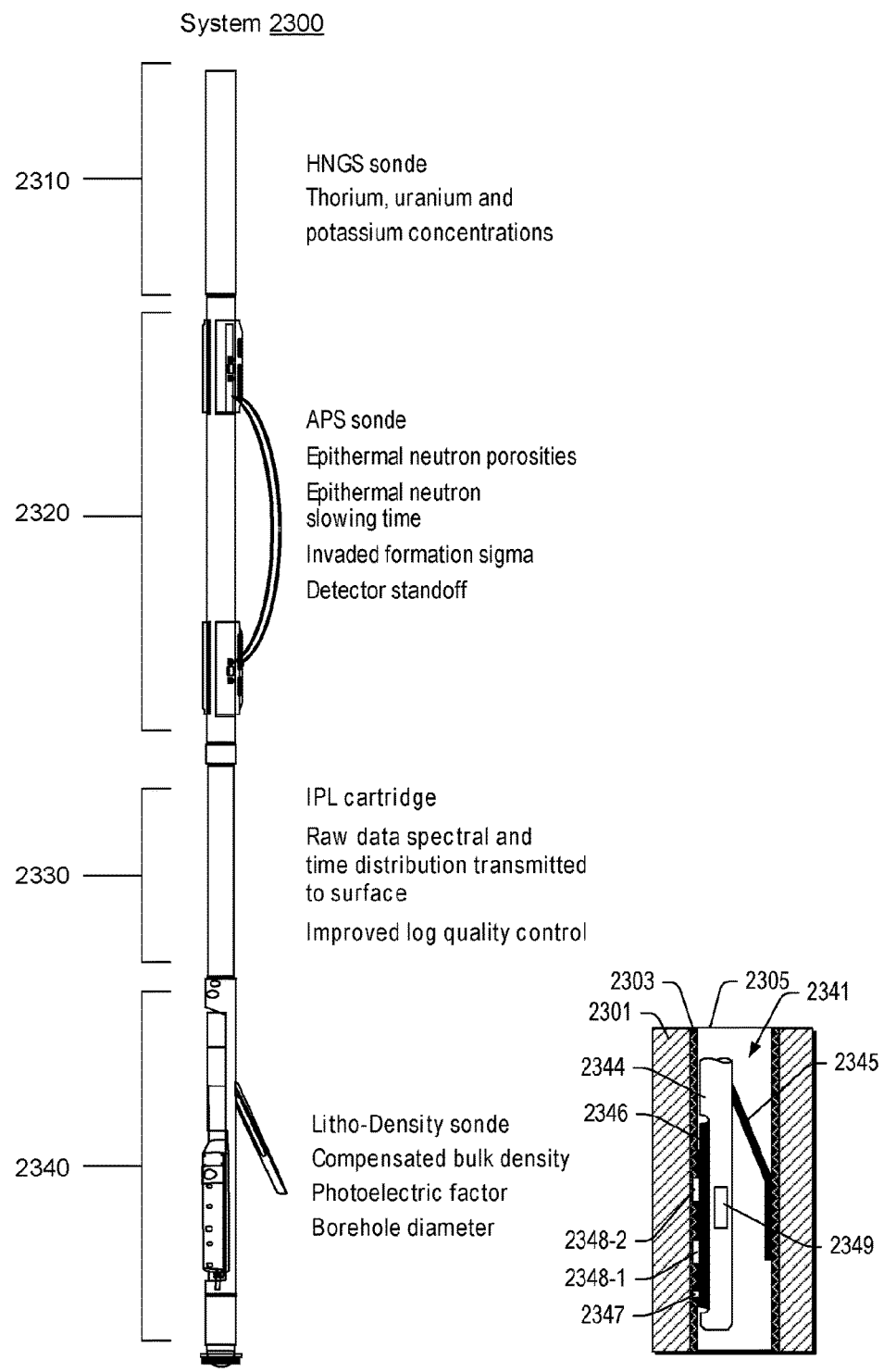
FIG. 23 illustrates an example of a system.

FIG. 23 shows an example of a system 2300 that can include various assemblies. For example, the system 2300 can include a hostile-environment natural gamma ray sonde (HNGS) assembly 2310, an accelerator porosity sonde (APS) assembly 2320, an integrated porosity lithology (IPL) cartridge assembly 2330 and a litho-density sonde (LDS) assembly 2340. As an example, the system 2300 may be an integrated porosity lithology (IPL) system such as, for example, the IPL system marketed by Schlumberger Limited, Houston, Tex.

In the example of FIG. 23, the litho-density sonde (LDS) assembly 2340 includes a pad with a gamma ray source and a plurality of detectors (e.g., two or more detectors). As an example, consider a Cesium-137 source, which emits gamma rays of about 0.66 MeV. As an example, detectors may be spaced, for example, axially along a LDS sonde. In the example of FIG. 23, the LDS assembly 2340 can include magnetic shielding and electronic circuitry, for example, to record full pulse-height spectra from the detectors and process such information (e.g., into windows, etc.). In such an example, bulk density and photoelectric effect (PE) information may be derived. As an example, spectral information may be used to improve log and calibration quality control.

As an example, a tool such as an LDS assembly can include at least one detector and at least one source. As an example, a distance between a source and a detector may be of the order of inches. As an example, a tool that includes a source and detectors may have an axial length of about one meter or less as to a maximum axial length defined by locations of the source and the detectors.

As an example, a tool such as an LDS assembly can include circuitry where the circuitry includes at least one controller (e.g., microcontroller, processor, etc.). As an example, the LDS assembly may include memory that can store instructions executable by at least one controller (e.g., consider executable firmware, software, etc.). As an example, one or more filters may be included in an LDS assembly and/or in a unit operatively coupled to an LDS assembly. In such an example, the one or more filters may be applied to data acquired via one or more detectors. As an example, a detector may have an associated filter or filter set. For example, where an LDS assembly includes N detectors, N filters or N sets of filters may be provided (e.g., in hardware, software, hardware and software).

As an example, the LDS assembly 2340 can include a specified range for bulk density measurements (e.g., about 2 g/cm$^3$ to about 3 g/cm$^3$ with an accuracy of about +/−0.01 g/cm$^3$) and a specified rang for photoelectric factor (PE factor) (e.g., about 1 to about 6, with an accuracy of about +/−10 percent).

FIG. 23 also shows an example of an LDS assembly 2341 with respect to a formation 2301 that may include mudcake 2303 in a borehole 2305. As shown in the example, the LDS assembly 2341 can include a body or housing 2344, a plough 2346, an arm 2345, a source 2347, a plurality of detectors 2348-1 and 2348-2 (e.g., two or more detectors), and circuitry 2349. As an example, the circuitry 2349 may include one or more controllers, memory, etc. As an example, a controller may be a microcontroller (e.g., an ARM chip, etc.), a processor, an ASIC, etc. As an example, a controller may operate via instructions stored in memory (e.g., firmware instructions, software instructions, RISC instructions, etc.). As an example, circuitry may be included in a cartridge such as, for example, the cartridge 2330 of the system 2300 of FIG. 23. As an example, one or more of the assemblies 2310, 2320, 2330 and 2340 of the system 2300 may include interfaces, for example, for communication of information. As an example, one or more of the assemblies 2310, 2320, 2330 and 2340 of the system 2300 may include memory, for example, as a storage device that may store one or more of data and instructions. As an example, a method may be implemented in part via instructions that may be executable by circuitry (e.g., a controller, microcontroller, processor, etc.).

The photoelectric effect (PE) may be defined as a gamma ray interaction in which a gamma ray is absorbed by a bound electron. In such a scenario, if the energy transferred exceeds the binding energy to the atom, the electron will be ejected. An ejected electron may be replaced within material and a characteristic X-ray emitted with an energy that is dependent on the atomic number of the material. The highest probability for this effect tends to occur at low gamma ray energy and in a material of high atomic number. The photoelectric effect (PE) is the principle behind a PEF log, which may be used, for example, to identify one or more lithologies.

As an example, a cross section may be defined to be a constant of proportionality relating the fraction of incident particles that undergo an interaction to the thickness and number of target atoms within a material, and the incident flux. Cross section can be a measure of the probability of an interaction. A microscopic cross section can have units of area per interacting atom and a macroscopic cross section, which is the product of the microscopic cross section and the number of particles per unit volume, can have units of inverse length. Cross sections for reactions may be determined experimentally and depend on type of interaction, material and energy of an incident particle.

The PE absorption cross section, in barns ($10^{-24}$ cm$^2$), is dependent on energy of gamma rays, E, as well as the average atomic number, Z. Z and, hence, PE, are nearly porosity independent while strongly discriminating lithology. PE does not tend to obey a linear, volumetric mixing law on which log analysis may utilize. As an example, a parameter, U, may be defined to represent a density-weighted photoelectric factor. Porosity may be directly from a density log as it tends to obey a linear bulk mixing law.

As an example, a tool can include a gamma-ray source and a plurality of detectors. When positioned in a borehole, gamma-rays emitted from the source go into the borehole and earth formation where they are scattered and some of them are subsequently detected by one or more of the detectors.

As an example, an adjustment for standoff caused by mudcake build-up or tool standoff can be accomplished by using two detectors with different depths of investigation. In such an example, a first detector can be at a shallow depth of investigation and more sensitive to borehole fluid or mudcake between the tool and the formation while a second detector can be at a longer distance from the source and less sensitive to the borehole environment and more sensitive to the formation. The difference between the two detector readings can be transformed into an adjustment for standoff and mudcake.

As an example, a tool may include three or more detectors, which may optionally be collimation for through casing measurement. As an example, a first detector and a third detector may use collimation and a middle detector may use collimation that is quite tight, for example, substantially perpendicular to a borehole wall to get a deeper density reading in through-casing measurements. A steep collimation angle of a middle detector can reduce its count rate and statistical precision. In an open hole measurement the depth of investigation of a middle detector and a first detector may become somewhat similar and the sensitivity to mudcake, which has a much smaller density than the steel casing, may be reduced.

As an example, a tool may allow for determining formation density and measuring photoelectric factor (PE factor or PEF) of a formation. As mentioned, PE measurement depends on absorption of low energy gamma-rays through the photoelectric effect in a formation. As PE depends on the atomic number of formation elements, it provides an indication of the lithology of the formation. Because PE absorption preferentially removes low energy gamma-rays, a tool housing can be constructed to allow for passage of low energy gamma-rays to detectors (e.g., mounted inside the housing). Such construction may use of a window of a material with a low atomic number (Z) in the housing and/or use a low-Z housing material (e.g., titanium). As an example, a window material may include beryllium and/or titanium. As an example, housing materials may include titanium or for lower pressure applications graphite or high-strength carbon compounds.

Figure 24:
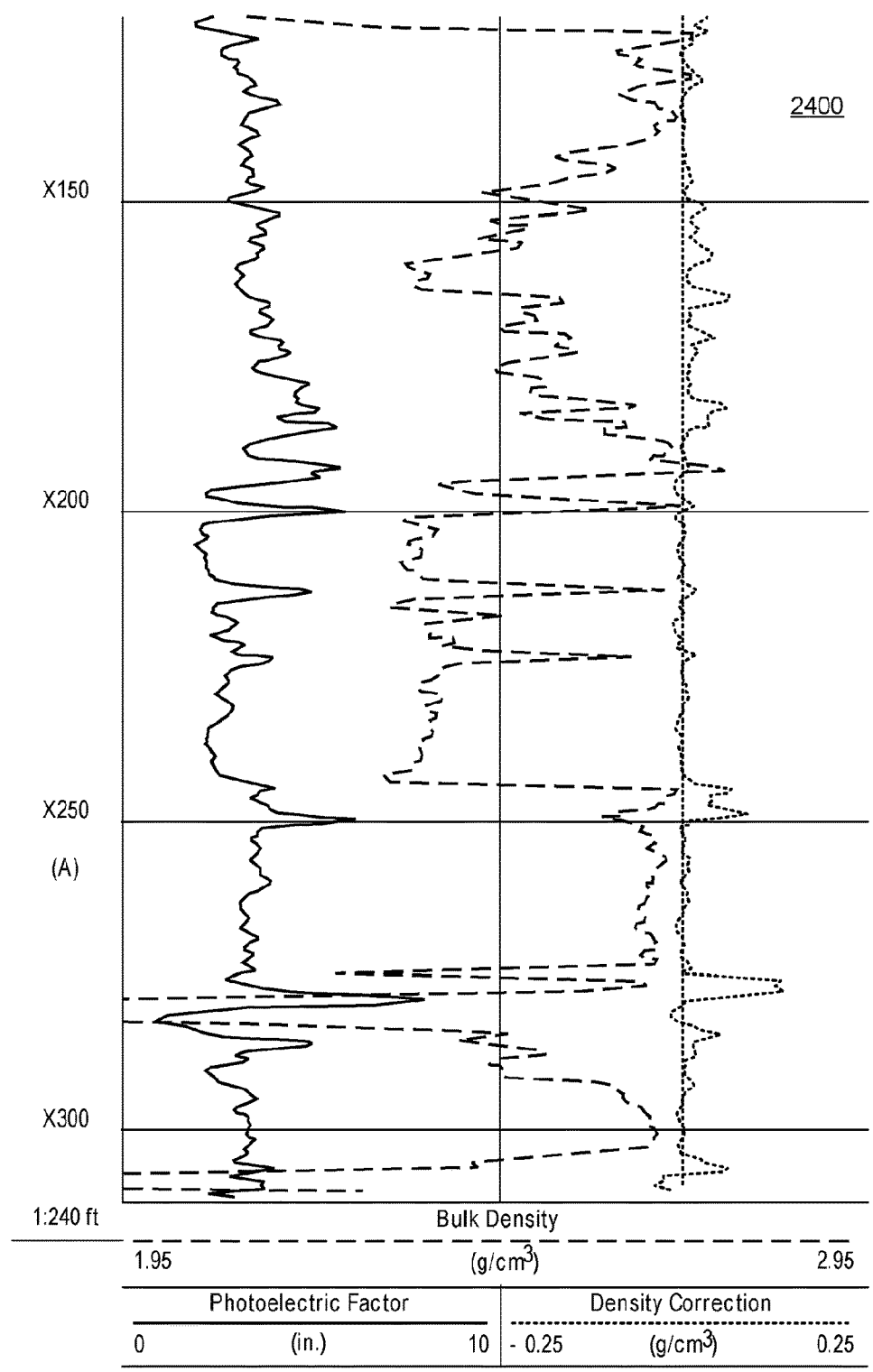
FIG. 24 illustrates examples of plots.

FIG. 24 shows an example of a log 2400 that includes bulk density measurement values, PE factor measurement values and density adjustment values with respect to distance (e.g., depth in a borehole).

In the log 2400, above X240 ft, a cuttings analysis describes the formation as sandstone with a varying amount of shaliness. Both gamma ray and PE measurements show this potential bed as shaly, yet the IPL neutron-density separation is larger than the separation in the lower, cleaner sands, indicating a gas effect. In this thinly bedded, shaly sandstone, the AIT and IPL combination detected several gas zones. The formation sigma measurement defines an extent of the shaly sand. The density measurement, together with the APS neutron porosity profile, which is sensitive to variations in formation hydrogen index, pinpoints tight streaks and about a 2-ft gas zone (e.g., about 0.6 meters). The AIT about 1-ft-resolution (e.g., about 0.3 meters) resistivity measurement also shows this zone. Formation matrix density variations make the CNL porosity profile comparatively insensitive to the presence of gas in the formation.

As an example, data acquired via a tool may be analyzed locally and/or remotely. As an example, a framework such as the TECHLOG® framework may be implemented to analyze data. As an example, a module may be a plugin operative with a framework. For example, consider a TECHLOG® "shale advisor" plugin module that can analyze data acquired via a tool.

As an example, a module may be implemented in a tool and/or in a framework. As an example, a module may be implemented in a tool to perform at least a portion of a workflow involving data analysis and a module may be implemented in a framework to perform at least a portion of a workflow involving data analysis. As an example, a workflow may include analyzing data in at least one of a tool and a framework.

As an example, a module may provide for an increase in resolution of density (e.g., density information) and/or PE factor (e.g., PE information).

As an example, the highly laminated nature of marine mudstone source rock reservoirs can pose some challenges for the petrophysical evaluation of such reservoir. The alternation of marls, tight calcite and porous weathered ash beds can challenge an evaluation workflows. Different logging devices used to characterize these formations may offer varying vertical resolutions, for example, from an approximately 0.2 inch resolution (e.g., about 0.5 cm) of a borehole imager to about a foot-range resolution (e.g., about 30 cm) of induction resistivity devices. Combining data from different sources can introduce biases in data analysis. An understanding and an optimization of vertical response of individual devices (e.g., assemblies, etc.) can facilitate analysis.

As an example, a method can include analyzing gamma-gamma density tool data in a manner that offers an improved vertical resolution. Such a method may be applied, for example, to environments that include mudstone where mudcake may be relatively nonexistent and where, for example, approximately inch-size laminations exist. Such a method may be applied, for example, to evaluation of laminated reservoirs.

As mentioned, a tool may include multiple detectors, for example, consider a three detector tool where a method to analyze the 3-detector gamma-gamma density data involves a workflow. Such a workflow can include processing as to a depth and resolution match of counting rates coming from each of the three detectors. Such processing aims to align the vertical response of the three detectors prior to the global inversion, which accepts the inputs collectively (e.g., together). Such processing tends to result in a vertical resolution of the final density and photoelectric factor (PE) that matches that of the lower vertical resolution detector.

As an example, to improve upon vertical resolution, a method may be applied that effectively overcomes the limitation in vertical resolution of the depth and resolution match for the global inversion. For example, a so-called high-resolution and/or very-high-resolution technique may be implemented to regain vertical resolution by sequentially dropping low resolution detector in the global inversion, each sequential benefiting from the previous process at lower resolution but with higher accuracy answers.

As an example, established vertical resolution for standard, high-resolution and very-high-resolution processing techniques are approximately 18 inches (e.g., about 46 cm), approximately 8 inches (e.g., about 20 cm) and approximately 2 inches (e.g., about 5 cm), respectively.

Processing may also deliver so-called mono-sensor densities (e.g., or mono-sensor) and photoelectric factors, corresponding to the density and PE seen by each detector individually. Such processing may be performed on the depth and resolution matched counting rates, providing sub-optimal mono-sensor properties in term of potential vertical resolution.

As an example, in a multi-density detector arrangement, multiple mono-sensor-measured densities may optionally be characterized to read formation density (e.g., when there is no substantial standoff). In such an example, where source-to-detector spacings differ, density detectors can have different sensitivity to standoff (e.g., a short-spaced detector can be more affected). As an example, data may be illustrated using a spine and rib plot, for example, where a spine corresponds to no substantial standoff measurements and where ribs illustrate standoff effect. As an example, as standoff increases, for example, short- and long-spacing densities can decrease where short-spacing density may decrease faster as it may experience more mud than a long-spacing measurement. Once rib shape is determined, formation density may then be extracted from mono-sensor densities (e.g., by following a rib up to a spine).

As an example, a spine and rib plot may correspond to data from a two-detector density tool where long-spacing versus short-spacing count rates are plotted for, for example, different formation densities, mudcake densities and mudcake thicknesses. In such an example, the spine can be the locus of points with no mudcake and the ribs can show the effect of mudcake at certain fixed formation densities. Such a plot may illustrate, graphically, that for a given formation density, there may be a rib for mudcake densities and thicknesses (e.g., though there may be three unknowns, it can be possible to make an adjustment via two measurements).

As an example, detectors may measure gamma rays scattered from a formation, for example, where the detectors may discriminate against low gamma ray energies that may have been influenced by photoelectric absorption. In such an example, measurements may respond to average density of material between a source and a detector. In such an example, one or more features (e.g., mudcake, borehole rugosity, etc.) may affect measurement. As an example, to compensate for mudcake, two or more detectors at different spacings may be utilized (e.g., where a mudcake compensation technique may be employed, etc.).

Vertical response function for a single source-detector measurement tends to be different for density and PE. Density measurement sensitivity tends to be spread between the source and detector, while a PE sensitivity region tends to be concentrated close to a detector. For example, photons that are absorbed close to the source are unlikely to have made it to the detector, so that the suppression effect on the detected spectrum tends to be nil.

As an example, a method can include accounting for an unbalance between PE and density sensitivity. Such a method may, for example, help to diminish potential biases in laminated formations.

As an example, a module may include analyzing gamma-gamma litho-density data acquired via a tool that includes a plurality of detectors where, for example, at least one of which can act as backscatter with approximately inches-range intrinsic vertical resolution.

As an example, a module may provide for computation of mono-sensor density and PE with optimized vertical filters. In such an example, the differences of vertical responses for density and PE can be taken into account within these filters. In such an example, once high-resolution mono-sensor density and PE are obtained, as an example, absence of standoff/mudcake can be assessed by the differences in these mono-sensor properties. As an example, a formation density and PE may be derived from the computed mono-sensor density and PE.

Figure 25:
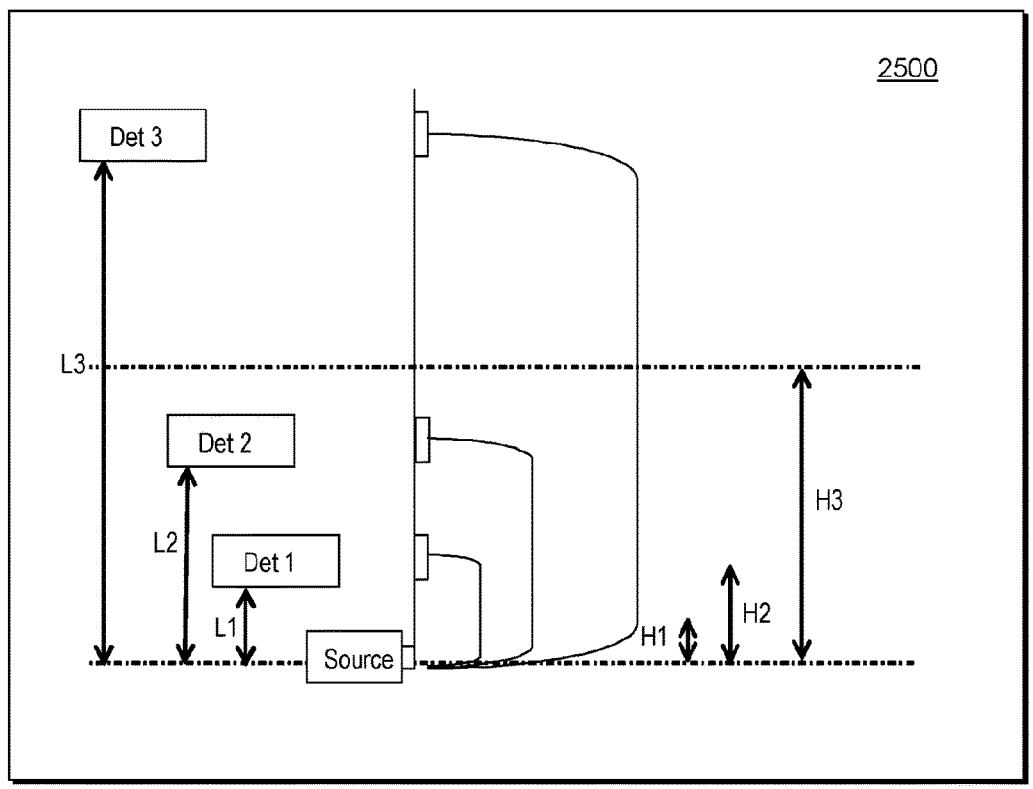
FIG. 25 illustrates examples of detection techniques.
Figure 25:
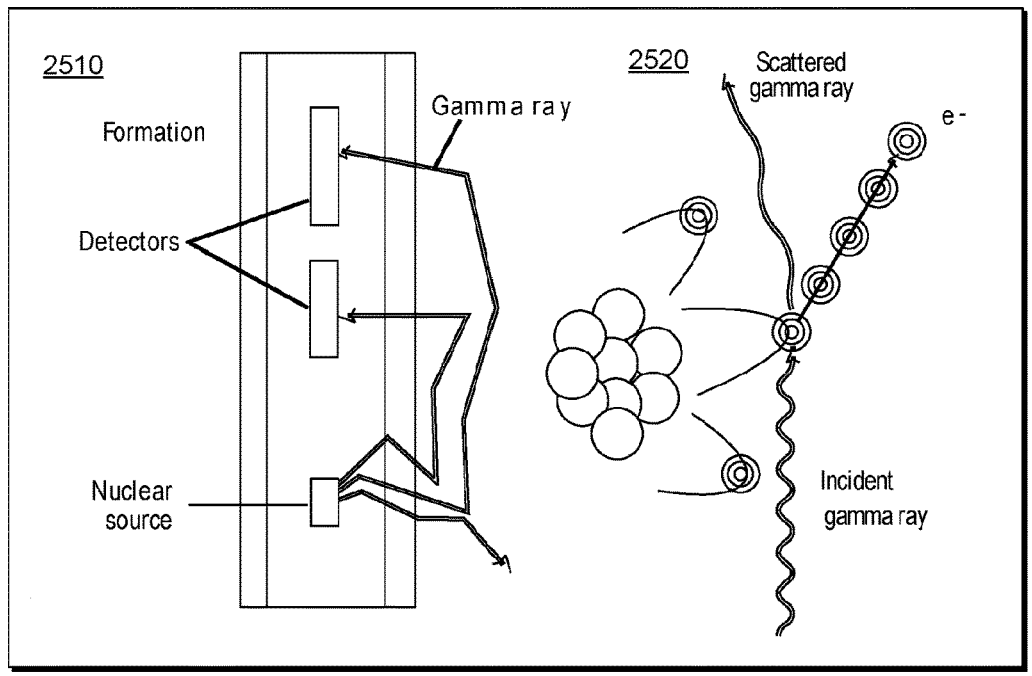

FIG. 25 shows an example of a system 2500 that includes a plurality of detectors arranged with respect to a source. As shown, distances L1, L2 and L3 may be axial distances between an individual detector and the source while distances H1, H2 and H3 may be half-distances. FIG. 25 also shows a schematic of at least a portion of a system 2510 along with a schematic of energy interactions 2520.

Figure 26:
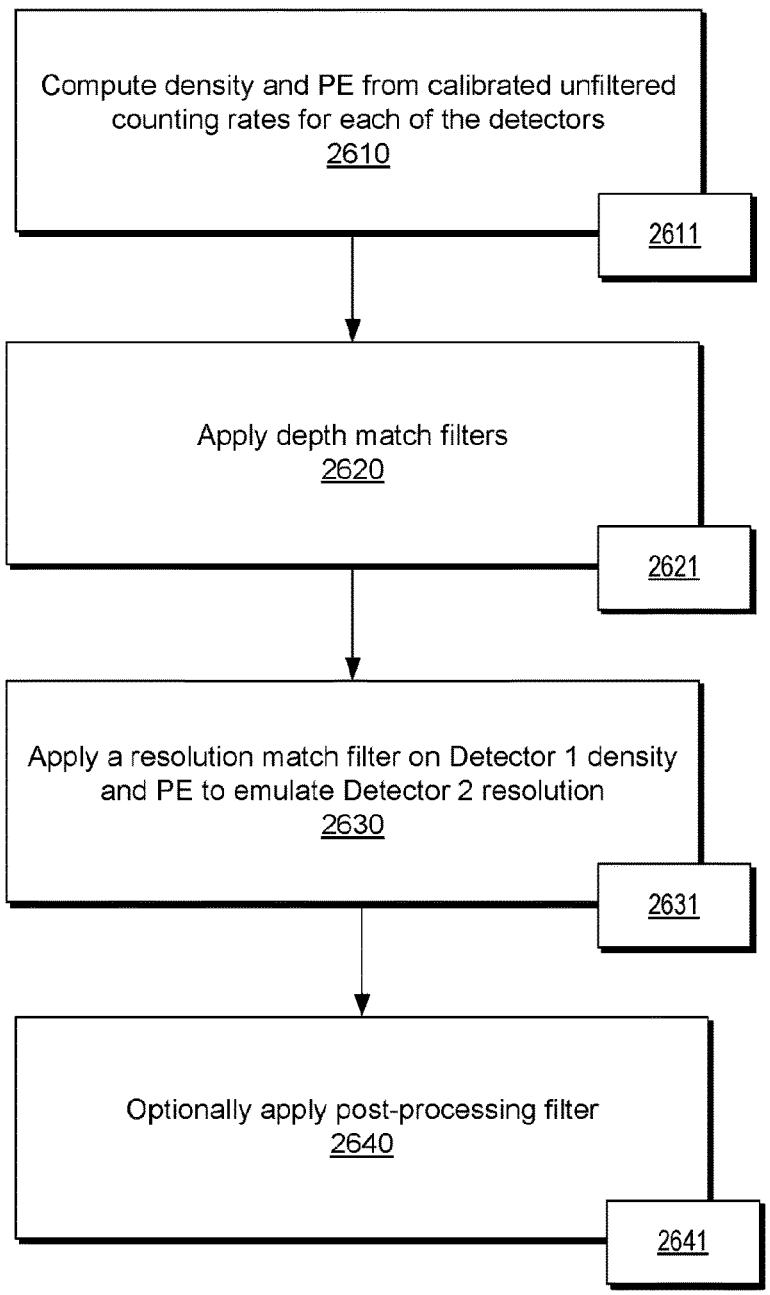
FIG. 26 illustrates an example of a method.

FIG. 26 shows an example of a method 2600 that includes various actions that can generate high resolution density curves. As shown, the method 2600 includes a compute block 2610 for computing density and PE from calibrated unfiltered counting rates for each of the detectors. In such an example, a transform for counts to density and PE can be applied, for example, via a spine algorithm, an inversion with forward model, or a database extrapolation technique (e.g., Radial Basis Functions, etc.). As an example, a combination of different energy windows for the PE computation and for the density computation may be used. In an application block 2620, the method 2600 can include apply depth match filters. For example, filters may be applied that are different for density and PE. And, for example, each detector can have an associated filter set (e.g., three filter sets for three detectors, etc). As shown, the method 2600 can include another application block 2630 for applying a resolution match filter on Detector 1 density and PE to emulate Detector 2 resolution. Such an approach can be implemented as a quality control, for example, to separate vertical resolution effect from standoff/mudcake effects. In the example of FIG. 26, the method 2600 may optionally include another application block 2640 for applying one or more post-processing filters, if desired. For example, such an approach may be desirable where a tool has been run fast (e.g., within a borehole) or with a weak source to reduce the statistical noise.

The method 2600 is shown in FIG. 26 in association with various computer-readable media (CRM) blocks 2611, 2621, 2631 and 2641. Such blocks may be computer-readable storage media blocks. While various blocks are shown, a single medium may be configured with instructions to allow for, at least in part, performance of various actions of the method 2600.

As an example, provided that a suitable separation exists between detectors 2 and detector 3 of a three detector tool with respect to a source of the tool, and that a gamma diffusion trend is followed, an associated density and PE can be obtained via a pseudo inverse of the linearized response function utilizing the available energy windows at a common time. In such an example, provided that detector 1 is sufficiently close to the source as to follow a mix of diffusion and backscatter behavior, its associated density and PE can be obtained, for example; via a RBF (radial basis function) database interpolation technique. As an example, a 2D processing approach may be implemented.

As an example, the linearized density and PE response function for a given energy window can be written as $$\ln W_i = \mu_i \cdot \rho + v_i \cdot u + L_i \qquad \text{Eqn. (3)}$$

where $W_i$ is the counting rate for energy window i, $\rho$ the apparent formation density, $u=\rho \cdot PE$ the mass photoelectric factor, and $\mu_i$, $v_i$ and $L_i$ coefficients that are fitted (e.g., via a database).

Considering that several energy window counting rates may be available, a system of equation can be written in matrix form $$Y = AX \qquad \text{Eqn. (4)}$$

where $$X = \begin{bmatrix} \rho \\ u \end{bmatrix},$$

$Y = [\ln W - L]_i$ and A is a 4×2 matrix containing the $\mu$ and $v$ coefficients.

The inverse of this system in terms of least squares is $$X=(A^tA)^{-1}A^tY \qquad \text{Eqn. (5)}$$

Uncertainties on the input counting rate ($E_i$) can be added in the system via a weighting matrix such as $$E = \begin{pmatrix} \frac{1}{E_1^2} & 0 & 0 \\ 0 & \ddots & 0 \\ 0 & 0 & \frac{1}{E_n^2} \end{pmatrix} \qquad \text{Eqn. (6)}$$

And the resolution the system can then be written as:

$$X=(A^tEA)^{-1}A^tEY \qquad \text{Eqn. (7)}$$

As an example, a method to compute apparent density and PE can be based on a response function where optimization can be performed via information available from different energy window counting rates.

As an example, where a detector is deemed to be not far enough from a source and has a backscatter component, the form of equation 6 may be adapted accordingly. For example, one or more terms may be added to the equation to match, for example, database information. In such an example, a database interpolation technique may be implemented that may be model independent.

As an example, a method may implement a radial basis function (RBF) where quality control of database information and an optimized selection of database points are taken into account for an interpolation.

As an example, a method may include applying depth match filters, for example, as explained with respect to the application block 2620 of the method 2600. In such an example, consider a tool depth reference that is in the middle of detector 3 (e.g., a detector farthest from the source). In such an example, measurements can be aligned at this depth. As an example, the density sensitivity of a given source detector measurement may be considered to be roughly spread between the source and detector, and may be approximated as, for example, having a box-shape. As a result, the detector 2 density depth shift may be computed as H3–H2, while the density depth shift for detector 1 may be computed as H3–H1.

As to PE, the PE sensitivity tends to be concentrated in front of a detector. As an example, it may be considered that the vertical resolution of a different detector to PE effect is somewhat similar, or at least less different than for density. For example, if detector 1 is close enough to operate in a backscatter mode, the PE sensitivity region will be approximately equivalent to the density sensitivity region. As an example, a method can include applying depth filters where depth filters applied to PE measurements can be different than those for density measurements. In a three-detector scenario, for example, detector 3 PE can be adjusted with a depth shift. As a result, the detector 3 PE depth shift can be of the order of –H3, where the detector 2 PE depth shift is H3–L2, while the density depth shift for detector 1 is H3–L1, or H3–H1, for example, if operating mainly in backscatter mode.

Figure 27:
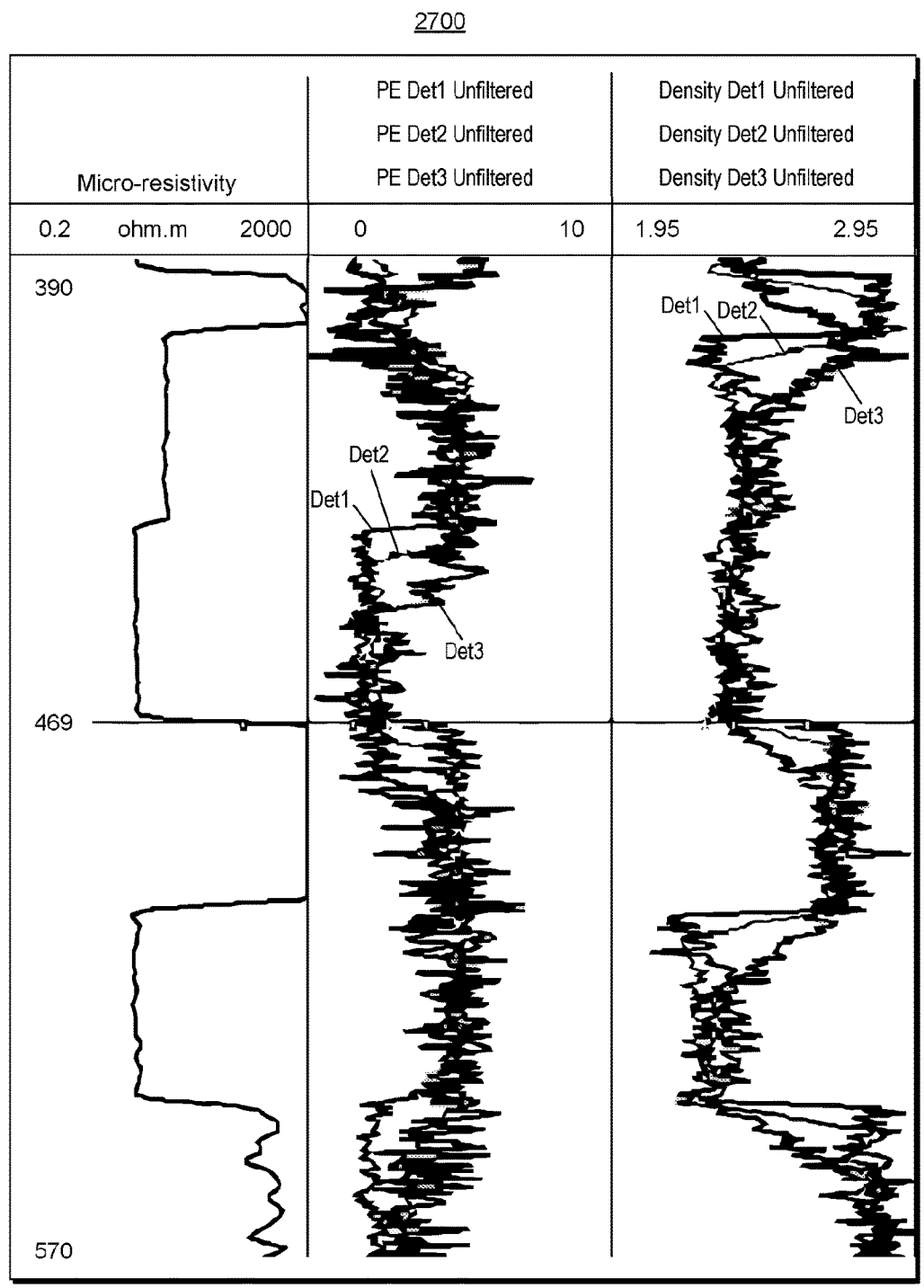
FIG. 27 illustrates examples of plots.

Different depth shifts for density and PE respectively are illustrated in an example log 2700 of FIG. 27, where unfiltered mono-sensor density and PE are shown. In the log 2700, data are shown for PE and density for three detectors (Det1, Det2 and Det3). As shown, the data include some vertical shifts, which may be seen at depths of about 390 inches (e.g., about 991 cm) to about 420 inches (e.g., about 1067 cm) with respect to vertical depth (e.g., position and extent) of a higher density bed (e.g., of about 10 inches in thickness). As another example, consider the range from about 470 inches (e.g., about 1194 cm) to about 505 inches (e.g., about 1283 cm). In this range, the unfiltered signals from the three detectors differ, particularly in how they rise and fall (e.g., with respect to density and depth). Specifically, Det1 rises and falls most sharply with respect to depth while Det2 and Det3 rise and fall more slowly and with a shift that is in a downhole direction.

The log 2700 corresponds to defined synthetic information for a formation, which can allow for trials to select filters, filter sets, etc., for particular formation features. As an example, a "synthetic" formation may be constructed and imaged. As an example, an actual borehole may be imaged where one or more images, data derived from images, etc., may be utilized, for example, to hone a method, to analyze data such as density and/or PE data, etc.

As an example, image data from a tool such as the fullbore Formation Microimager (FMI) tool may provide micro-resistivity formation images (see, e.g., the tool 237 of FIG. 2). Such a tool may provide for about 80 percent borehole coverage in a borehole of about 8 inches in diameter (e.g., about 20 cm in diameter). Such a tool may provide for about 0.2 inch (e.g., about 0.5 cm) image resolution in vertical and azimuthal directions. Such images may facilitate identification of features in laminated (e.g., sediments of fluvial, turbidite, etc., depositional environments).

As an example, bore data (e.g., imagery, etc.) may be presented in a 2-D format for purposes of analysis, interpretation, etc. Various materials (e.g., beds, fractures, or other features) may be seen and, for materials being substantially planar with respect to intersection of a bore, these materials tend to have a sinusoidal shape when viewed in a 2-D format. In a process referred to as picking dips (e.g., dip identification), cylindrical surface data may be presented on a display where a "sine" cursor tool allows a user to adjust amplitude, position along a z-axis, etc., of a sinusoidal curve to align it with the data for the stratified material. In particular, the sinusoidal curve may be positioned where image contrast (e.g., or other attribute) differs to a certain extent, for example, to represent differences in resistivity or one or more other properties of the material.

The logs are from an example trial well built with blocks of known formation. In Track 1, the micro-resistivity log delineates the bed boundaries (e.g., also consider micro-resistivity image information). In Track 2, unfiltered mono-sensor PE for the 3 detectors are plotted. In Track 3, unfiltered mono-sensor densities for the 3 detectors are plotted. The depth track is in units of an inch. As shown, the mono-sensor densities appear depth-shifted one with respect to the other. Regarding the PE: (A) the depth shifts between detector 1 PE, detector 2 PE and detector 3 PE are larger than the depth shift for density; (B) the intrinsic resolution of PE measurement is better than that of density measurement; and (C) the PE and density information are not in-depth. These observations confirm the differences in vertical response for PE and density measurements, and they confirm the dedicated depth filters approach (e.g., per the method 2600 of FIG. 26).

As an example, the application block 2630 of the method 2600 of FIG. 26 can include averaging filter of length L2–L1 applied on detector 1 density to create a new log that matches the vertical resolution of detector 2, but with detector 1 depth of investigation. Comparing this new density with detector 2 density may help assist in understanding, for example, if the separation observed from original detector 1 to detector 2 density are due to thin bed effect alone or also to radial effects.

As an example, the optional application block 2640 of the method 2600 of FIG. 26 may be implemented, for example, for smoothing of data. For example, consider implementation of the block 2640 where due to a too high logging speed or a weak source smoothing may be appropriate. As an example, averaging filters may include, for example, one or more Gaussian-shape filters.

Figure 28:
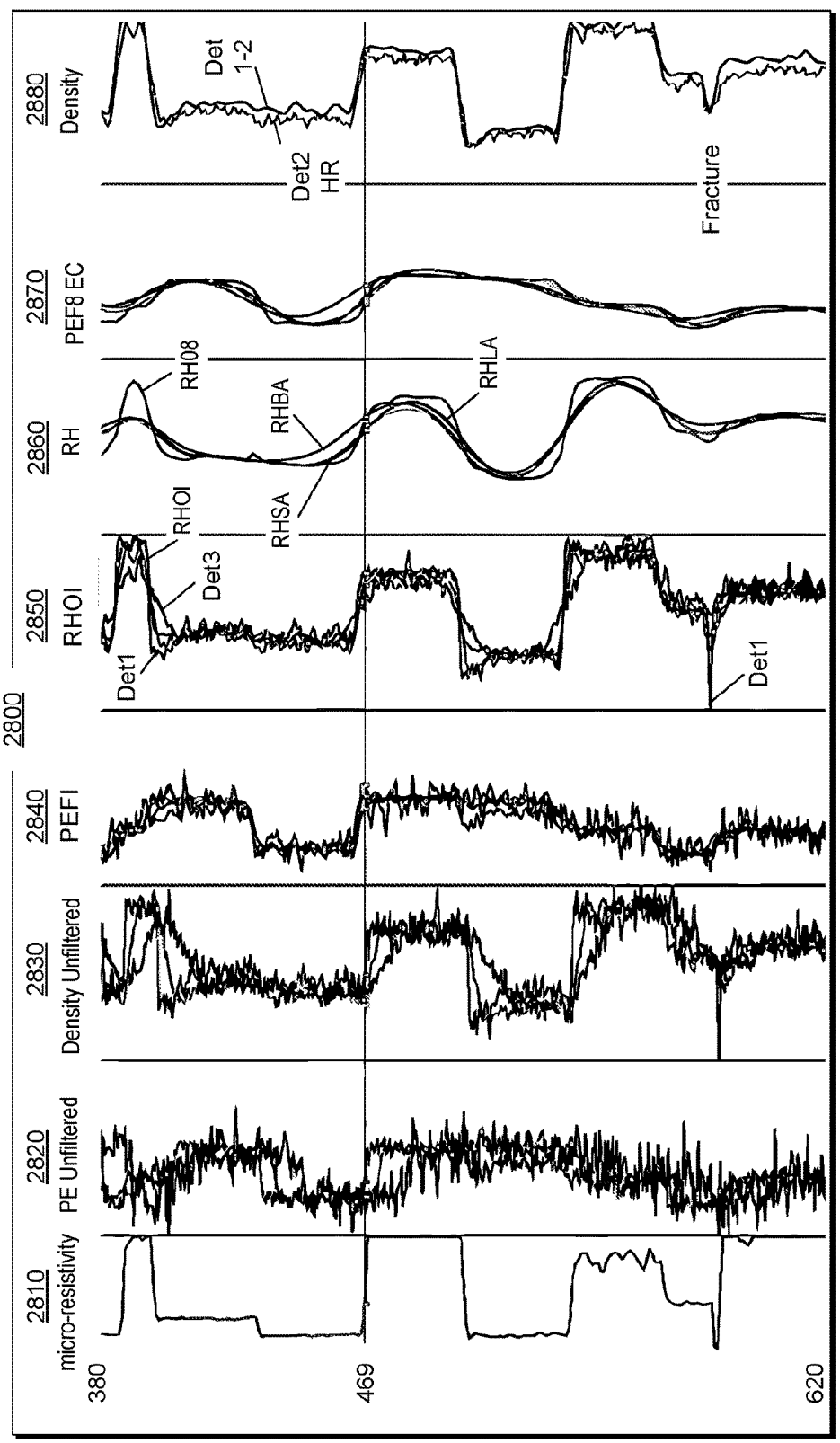
FIG. 28 illustrates examples of plots.

FIG. 28 shows a log 2800 that includes eight tracks, labeled 2810, 2820, 2830, 2840, 2850, 2860, 2870 and 2880. The log 2800 includes density curves in track 2880 obtained after depth shifting, with an additional 1.5 inch (e.g., about 3.8 cm) filtering and 7 inch (e.g., about 18 cm) global depth shift to match the image. In the track 2880, a fracture is labelled as corresponding to a depth of approximately 590 inches (e.g., about 1500 cm). The log 2800 corresponds to defined synthetic information for a formation.

Existing "Very High Resolution" (VRH) processing PE (PEFI) and density (RHOI) are included in tracks 2840 and 2850, respectively. These PE and density data are adjusted for standoff/effect mudcake, and in the case of thin bed, resolution effects are interpreted as standoff, and the resulting adjusted density may not be entirely accurate. The "High Resolution" (HR) density and (HR) PE may be affected by standoff effect, as there is no attempt to compensate for it, but they represent real density reading, and can be quality control a posteriori to decide which of them represents best the density for interpretation.

In the log 2800, unfiltered density in the track 2830 may be compared to filtered information in the track 2850, which is illustrated along with data from "Very High Resolution" (VRH) processing density (RHOI). A comparison of RHOI to densities of "Det1 HR", "Det2 HR" and "Det3 HR" at depths of approximately 390 inches (e.g., about 991 cm) to about 420 inches (e.g., about 1067 cm) show that differences exist. In particular, near the high density bed, a low density bed at a deeper depth is visible in the filtered information Det1 HR, Det2 HR and not in the RHOI. Such a lack of indication of the lower density bed is also shown in the RHOI at about 500 inches (e.g., about 1270 cm) to about 510 inches (e.g., about 1295 cm). Thus, a method such as the method 2600 of FIG. 26 may be applied to detect relatively thin beds that differ in density from an adjacent bed.

As to shifting of density for the detectors, a method can include processing that shifts density data of one or more of the detectors. Such a method can account for vertical response of density (e.g., and PE) individually for each of a plurality of detectors (e.g., along with a depth match). For example, consider the density data for the third detector in the log 2700 of FIG. 27 and the density data for the third detector in the log 2800 of FIG. 28; noting an uncompensated depth of the micro-resistivity of track 2810 of the log 2800 of FIG. 28 (e.g., a slight shift exists, which may be globally adjusted via center points of tools, etc.).

In the tracks 2860 and 2870 of the log 2800, existing mono-sensor density and PE are plotted. RHLA corresponds to detector 3, RHSA to detector 2 and RHBA to detector 1. The vertical resolution of these mono-sensor density and PE is matched to that of the farther spacing, i.e., detector 3, and substantially no information on the layers is in this example are available.

In the track 2880, detector 1 density is resolution-matched (e.g., density Det 1-2) over the detector 2 vertical resolution. In such an example, its comparison with detector 2 density allows a check of radial versus vertical resolution effects.

For example, if vertical resolution effects predominant and are responsible for the mono-sensor density and PE differences, one may see the two curves as roughly overlapping. However, if radial effects take place, differences may be seen (e.g., detected), as vertical resolution matching does not change the depth of investigation of detector 1.

As an example, as long as the bed thickness is larger than a view distance (e.g., in inches or in centimeters, etc.), the existing VHR curves capture most of the formation variability. However, when bed thickness reaches the inch size (inch scale) (e.g., or about 2 cm to about 3 cm size), there can be a loss of information.

Figure 29:
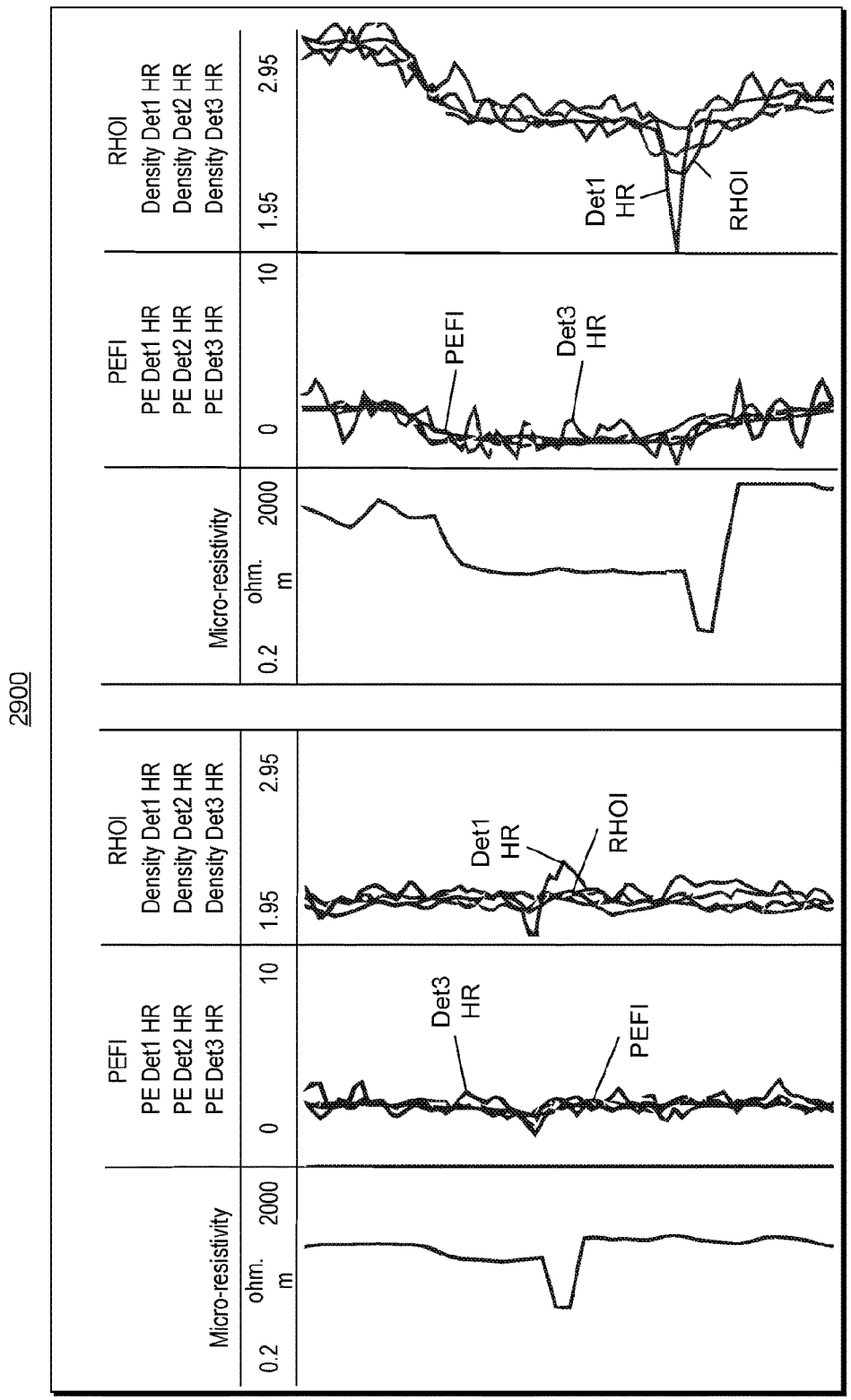
FIG. 29 illustrates examples of plots.

FIG. 29 shows an example log 2900 where two inch-size washouts (e.g., about 5 cm-size washouts) at block interfaces may be hardly seen via VRH density, but may be appropriately identified via an analysis that includes application of filters for a new Det 1 HR density and PE.

As an example, a method that includes applying filters to acquired detector data can improve resolution of density and PE curves. Such a method may be applied, for example, where an interpretation may include looking for inch size events.

As an example, a log may include information from a real formation. For example, consider a formation that includes clay layers are intercalated in tight mudstone where thicknesses estimated from images are in a range of about 0.3 inches to about 3 inches. An approach such as that of the method 2600 of FIG. 26 includes filtering and generating a new density curve for detector 1, which may allow for picking the layers that were identified via images. Such an approach may provide resolution for picking layers that are thinner than discernable via an RHOI curve (e.g., to pick layers at 1.5 inch and less; e.g., about 3.8 cm and less). As an example, images may show features such as degraded ash beds, which are lower density features (e.g., may be rendered as darker bands).

As an example, a method can include identifying a layer that may have interacted with drilling fluid. As an example, a method can include analysis of data of a formation, for example, to plan for and execute stimulation of a reservoir through fracturing. As an example, for a calcite reservoir, presence of one or more identified clay layers may affect a hydraulic fracturing process. Such a process may account for the presence of such features.

As an example, a method may be applied to a tight mudstone formation with the intercalation of marls, tight calcite and weathered ash layers. In such an example, HR density and PE may enhance discrimination of features.

As an example, a method may include analyzing density and/or PE to identify an igneous deposit (e.g., a weathered ash bed, etc.), to characterize an igneous deposit (e.g., a weathered ash bed, etc.), etc.

As an example, a method may include a classification block that can classify at least a portion of a geologic environment based at least in part on an analysis of density and/or PE (e.g., as processed via a method such as the method 2600 of FIG. 26). As an example, a classification may consider thickness, mechanical stability and/or chemical stability, mineralogy, distance to a target, etc.

As an example, a workflow may include detecting one or more igneous deposits and modeling the one or more igneous deposits in a simulation model. For example, a simulation model may be a reservoir simulation model, a completions simulation model, a petroleum systems simulation model, etc.

As an example, a method may include processing high resolution micro-resistivity log information. Such a method may optionally operate without filtering of raw micro-log tool data. As an example, depth-matching depth shift may be performed. As an example, micro-log resistivity log information may optionally be used as part of a borehole image calibration process.

As an example, a method can include processing density and photoelectric factor (PE) log data. As an example, such a method can process such data in a manner that allows for retrieving information on igneous deposits as thin as about 2.5 cm (e.g., a thickness of about one inch) or less. Density tends to be related to porosity of an igneous deposit while PE may provide an indication as to composition.

As an example, a three-detector litho-density tool may be implemented for acquisition of data. As an example, a method may include computing high resolution mono-sensor density and PE for backscatter. As an example, where mudcake does not form in front of an organic shale, backscatter density and PE may represent formation density and PE. As an example, short spacing density and PE together with long spacing density may be used to quality control backscatter output.

As mentioned, a method can include preparing data from one or more sources where such data may relate to one or more possible aspects of an igneous deposit. As an example, such information may be processed to enhance identification and characterization of weathered ash beds.

As an example, igneous deposits may be categorized or ranked in a matrix in a manner that can allow for visualization (e.g., rendering to a display, a printer, etc.) such that a user may examine possible effects on completion and the variability of the igneous deposits.

Figure 30:
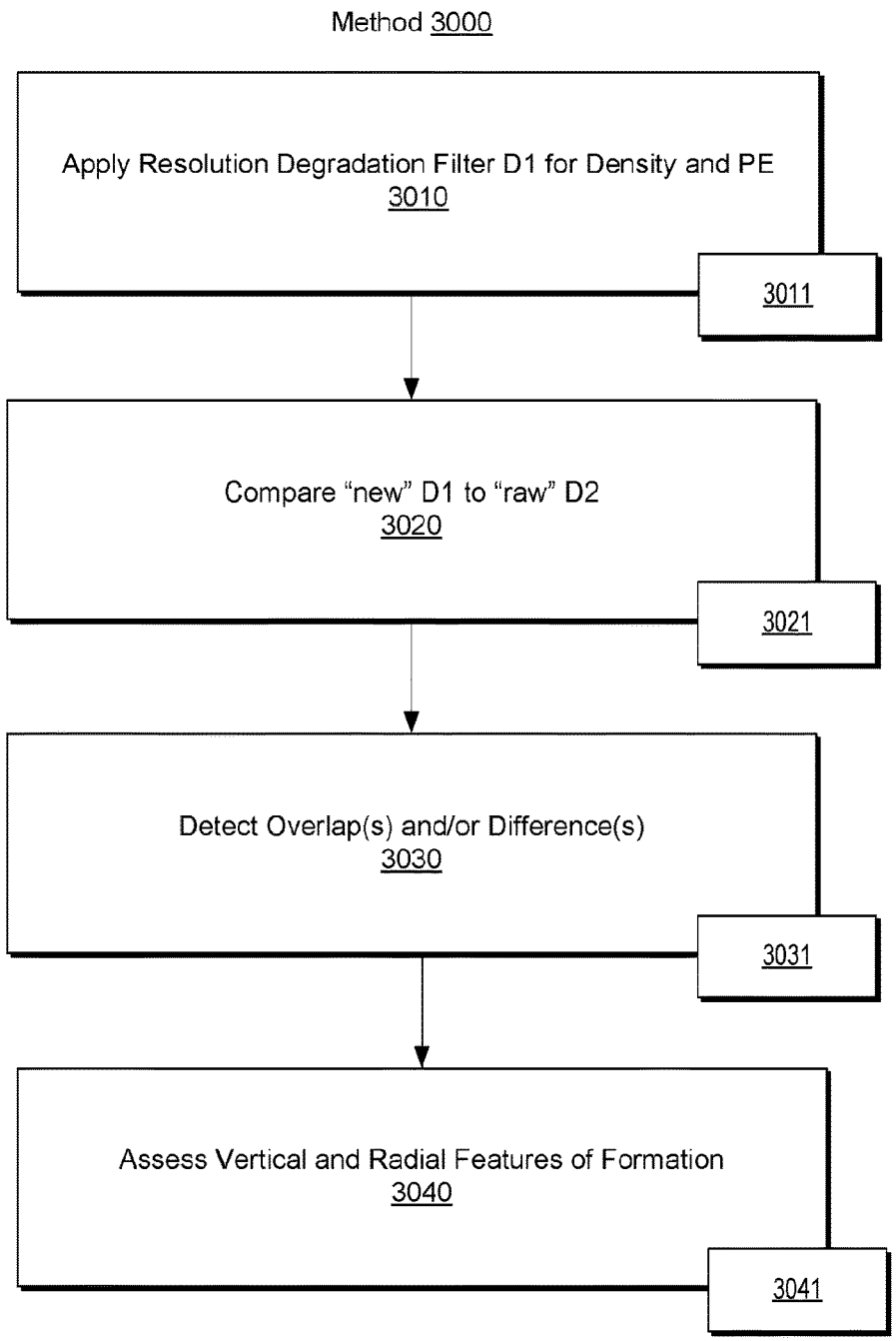
FIG. 30 illustrates an example of a method.

FIG. 30 shows an example of a method 3000 that includes an application block 3010 for applying a resolution degradation filter to detector D1 data for density and PE to generate "new" detector D1 data (e.g., processed detector D1 data); a comparison block 3020 for comparing the new detector D1 data to detector D2 data (e.g., raw data of detector D2); a detection block 3030 for detecting one or more overlaps and/or one or more differences in the data being compared; and an assessment block 3040 for assessing vertical and/or radial features of a formation based at least in part on the one or more detected overlaps and/or one or more detected differences.

The method 3000 can include emulating one detector based on another detector. For example, the method 3000 may include emulating detector 2 with detector 1. As an example, dynamics can differ between two detectors and a source. As an example, a further detector may be emulated by a closer detector (e.g., emulate detector 2 with detector 1). Upon a comparison, if a match exists, then a feature may be a fracture or a small bed; whereas, if a match does not exist, then a feature may be a mudcake. Such an approach may consider that detector 1 is closer to a source than detector 2 (e.g., depth-of-investigation "DOI" of detector 1 is less than that of detector 2) and filtering of detector 1 cannot reach the physical arrangement of detector 2 (e.g., the DOI of detector 2); however, as to vertical resolution, detector 1 can be degraded via filtering as to vertical resolution to match that of detector 2 (see, e.g., FIG. 25).

The method 3000 is shown in FIG. 30 in association with various computer-readable media (CRM) blocks 3011, 3021, 3031 and 3041. Such blocks may be computer-readable storage media. While various blocks are shown, a single medium may be configured with instructions to allow for, at least in part, performance of various actions of the method 3000.

As an example, one or more computer-readable media may include processor-executable instructions to flag a portion of a geologic environment based at least in part on presence of an igneous deposit and instructions to adjust a completion plan based at least in part on the flagged portion of the geologic environment.

As an example, a method can include computing density values and photoelectric factor values based at least in part on counting rates in a formation for each of a plurality of radiation detectors; applying density depth match filters to the density values to generated filtered density values and applying photoelectric factor depth match filters to the photoelectric factor values to generate filtered photoelectric factor values where each of the radiation detectors is associated with a corresponding depth match filter and a corresponding photoelectric factor filter; and outputting at least one log that includes the generated filtered density values and the generated filtered photoelectric factor values. Such a method may include identifying at least one feature in the formation based at least in part on at least one of the at least one log. For example, consider identifying a bed, identifying a fracture, etc. As an example, a method can include identifying mudcake based at least in part on a log.

As an example, a method can include applying a resolution match filter to at least one of density values and photoelectric factor values of a detector located closest to a radiation source of a tool that includes a plurality of detectors to emulate at least one of density values and photoelectric factor values of another one of the plurality of detectors. In such an example, the method may include outputting a log of emulated density and/or photoelectric factor values.

As an example, a plurality of radiation detectors may be mounted on a tool where the tool includes a radiation source. In such an example, an axial span along the tool that includes the plurality of radiation detectors and the radiation source may be of a distance of approximately one meter or less.

As an example, a system can include a processor; memory accessibly by the processor; one or more modules stored in the memory where the one or more modules include processor-executable instructions to instruct the system and where the instructions the instructions to compute density values and photoelectric factor values based at least in part on counting rates in a formation for each of a plurality of radiation detectors; apply density depth match filters to the density values to generated filtered density values and apply photoelectric factor depth match filters to the photoelectric factor values to generate filtered photoelectric factor values where each of the radiation detectors is associated with a corresponding depth match filter and a corresponding photoelectric factor filter; and output the generated filtered density values and the generated filtered photoelectric factor values. As an example, such a system may include the plurality of radiation detectors (e.g., the system may be a tool suitable for deployment in a borehole) and such a system may include a source that emits radiation. As an example, a system may include a housing and an arm where the arm is extendable to position the housing in a borehole (see, e.g., FIG. 23).

As an example, a system can include an interface that receives counting rates. As an example, a system may include a cartridge that includes a data storage device where generated filtered density values and generated filtered photoelectric factor values may be output to the data storage device (e.g., stored to the data storage device, optionally for transmission via an interface).

As an example, a system can include a communication interface (e.g., as circuitry, etc.) where generated filtered density values and generated filtered photoelectric factor values can be output via the communication interface. As an example, a system may include a communication interface to receive data and/or instructions.

As an example, a system can include instructions to output at least one log that includes generated filtered density values and/or generated filtered photoelectric factor values.

As an example, one or more computer-readable media can include processor-executable instructions where the processor-executable instructions include instructions to instruct a computer to compute density values and photoelectric factor values based at least in part on counting rates in a formation for each of a plurality of radiation detectors; apply density depth match filters to the density values to generated filtered density values and apply photoelectric factor depth match filters to the photoelectric factor values to generate filtered photoelectric factor values where each of the radiation detectors is associated with a corresponding depth match filter and a corresponding photoelectric factor filter; and output at least one log that includes at least a portion of the generated filtered density values and the generated filtered photoelectric factor values.

As an example, one or more computer-readable media can include instructions to instruct a computer to apply a resolution match filter to at least one of density values and photoelectric factor values of a detector located closest to a radiation source of a tool that includes a plurality of detectors to emulate at least one of density values and photoelectric factor values of another one of the plurality of detectors. In such an example, instructions may be included to instruct the computer to output a log of emulated density and/or photoelectric factor values.

Figure 31:
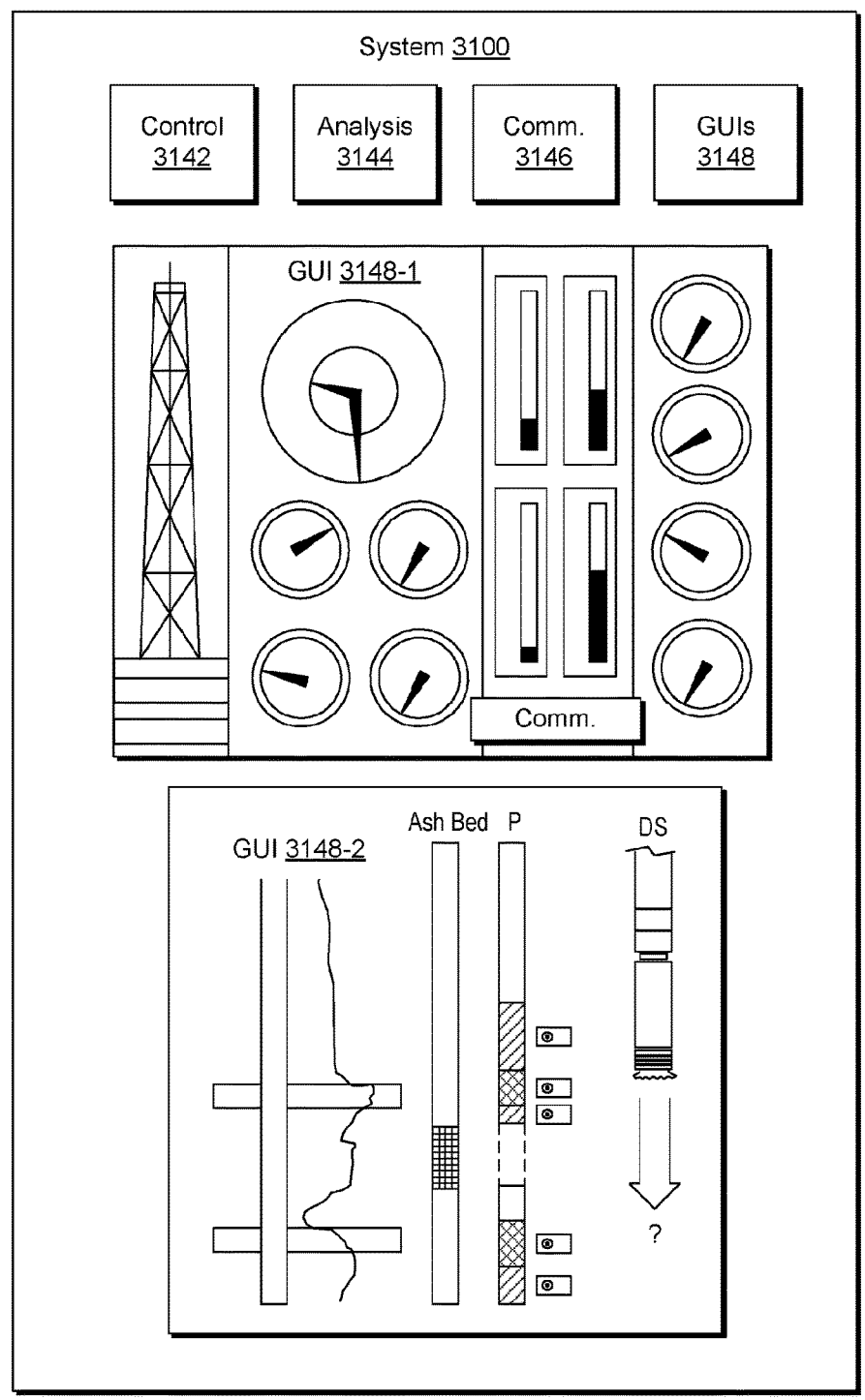
FIG. 31 illustrates an example of a system.

FIG. 31 shows an example of a system 3100 that includes various modules such as a control module 3142, an analysis module 3144, a communication module 3146 and one or more graphical user interface modules 3148. As an example, the system 3100 may include one or more features of a framework such as, for example, the TECHLOG® framework, the INTERACT® framework, etc. As an example, a GUI 3148-1 may render information as to real-time conditions at a site (e.g., a well site) and a GUI 3148-2 may render information as to one or more regions within an environment. For example, a region may be a drilled region, a region to be drilled, etc. As shown in the GUI 3148-2, values, which may be index values, may be rendered with respect to a spatial dimension such as depth. Such values may indicate lithology of a region, for example, consider a cemented region. In such an example, equipment (e.g., drillstring equipment) may be controlled to account for drilling into the cemented region, avoiding the cemented region, etc.

As an example, various values may indicate lithology of a region, for example, consider an igneous deposit. As an example, the GUI 3148-2 may include one or more of an Igneous deposit (e.g., "Ash Bed", etc.) graphic, an operational parameter(s) graphic (P) and a drill string (DS) graphic. In such an example, equipment (e.g., drillstring equipment) may be controlled to account for drilling into an igneous deposit or igneous deposits, avoiding an igneous deposit or igneous deposits, etc.

As an example, information rendered to a display can include zone information. For example, consider the zone information of FIG. 22 being rendered in a format where one or more characteristics of rock may be visually discernable. As an example, a GUI can include an anisotropy track, a Musc/Orth track, a diagenetic track, a porosity track, etc. As an example, one or more tracks may be color coded or otherwise scaled and rendered to allow for discernment of various characteristics and differences therebetween (e.g., and/or similarities) for depths in a geologic environment where one or more wells may be planned and/or drilled.

As an example, a geologic environment may be an environment that includes a reservoir or reservoirs. As an example, a geologic environment may be an environment that is a geothermal environment. As an example, a geologic environment may be an environment that is utilized for storage of waste such as, for example, nuclear waste. As an example, a geologic environment may be a non-oil and gas environment (e.g., as may be suitable for production). As an example, a geologic environment may be a hydrologic environment.

As an example, a model may be utilized for one or more completions in a geothermal environment. As an example, in a geothermal environment, a gradient may characterize the rate of increase in temperature per unit depth in the Earth. As an example, a temperature gradient may be associated with a volcanic area or volcanic areas. As an example, information as to igneous deposits may assist with a completion in a geothermal or other geologic environment.

As to nuclear waste (e.g., radioactive waste), it may be a by-product of nuclear power generation or another application of nuclear fission or nuclear technology (e.g., research, medicine, etc.). The time radioactive waste is to be stored can depend on the type of waste and radioactive isotopes. For example, storage may be in a range from a few days for very short-lived isotopes to millions of years. As an example, a segregation and storage for plan may call for near-surface disposal for low and some intermediate level waste and deep burial or partitioning/transmutation for the high-level waste. As an example, a method can include outputting a model that can assist with waste management. For example, a model may characterize risk of flow for a subsurface where waste exists or where waste is to be stored. As an example, a model may facilitate planning as to one or more completions associated with subsurface waste storage.

As an example, a model may be output that can assist with hydrologic analysis of a region. For example, a model may characterize rock with respect to movement, distribution, and/or quality of water, optionally in a region that includes oil, gas, waste, etc. As an example, a model may facilitate planning of one or more completions with respect to hydrology of a region. For example, where a region includes one or more layers that may be amenable to washout, a completion may be planned with respect to path and/or construction to address potential risk of washout.

Figure 32:
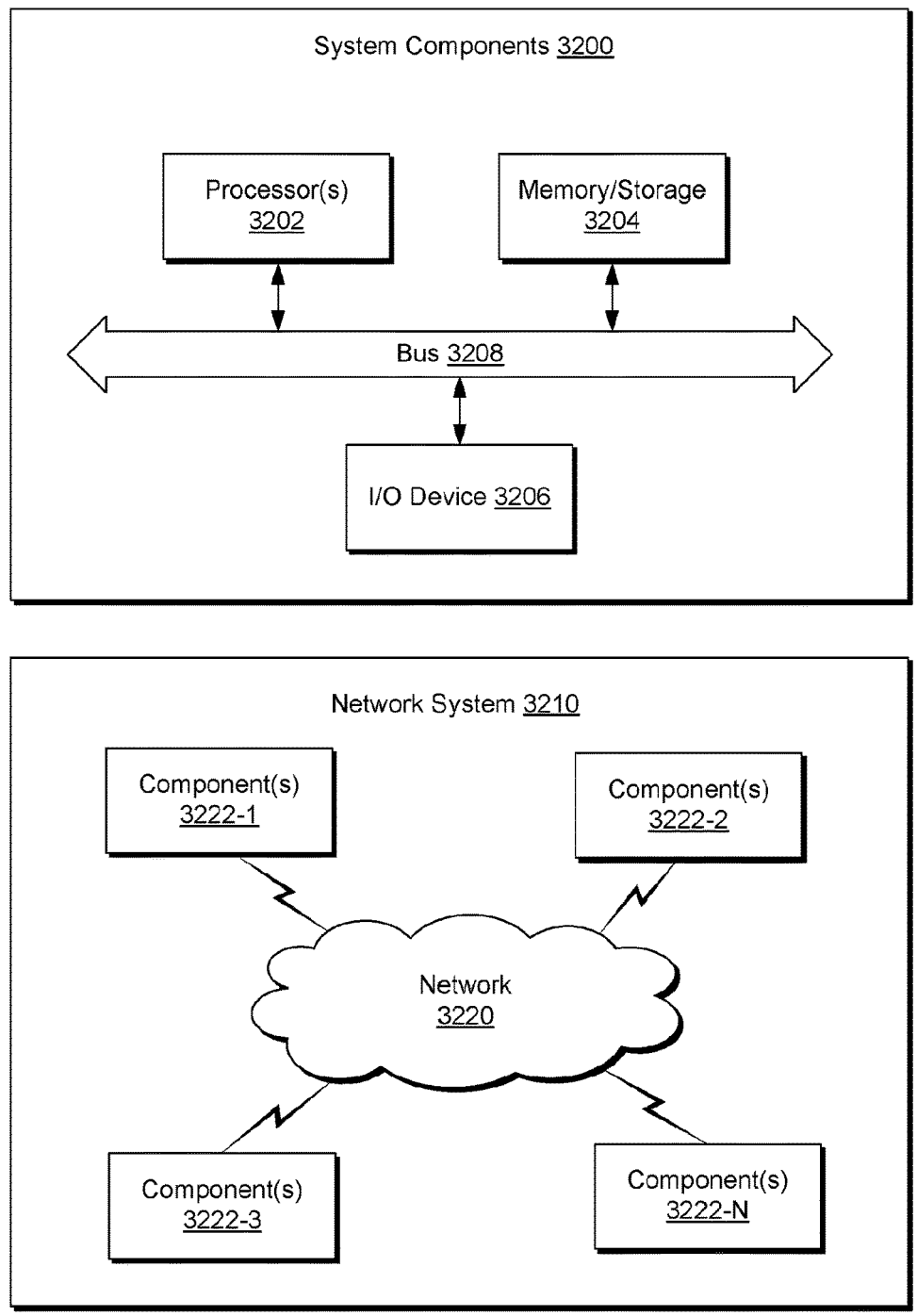
FIG. 32 illustrates example components of a system and a networked system.

FIG. 32 shows components of an example of a computing system 3200 and an example of a networked system 3210. The system 3200 includes one or more processors 3202, memory and/or storage components 3204, one or more input and/or output devices 3206 and a bus 3208. In an example embodiment, instructions may be stored in one or more computer-readable media (e.g., memory/storage components 3204). Such instructions may be read by one or more processors (e.g., the processor(s) 3202) via a communication bus (e.g., the bus 3208), which may be wired or wireless. The one or more processors may execute such instructions to implement (wholly or in part) one or more attributes (e.g., as part of a method). A user may view output from and interact with a process via an I/O device (e.g., the device 3206). In an example embodiment, a computer-readable medium may be a storage component such as a physical memory storage device, for example, a chip, a chip on a package, a memory card, etc. (e.g., a computer-readable storage medium).

In an example embodiment, components may be distributed, such as in the network system 3210. The network system 3210 includes components 3222-1, 3222-2, 3222-3, . . . 3222-N. For example, the components 3222-1 may include the processor(s) 3202 while the component(s) 3222-3 may include memory accessible by the processor(s) 3202. Further, the component(s) 3202-2 may include an I/O device for display and optionally interaction with a method. The network may be or include the Internet, an intranet, a cellular network, a satellite network, etc.

As an example, a device may be a mobile device that includes one or more network interfaces for communication of information. For example, a mobile device may include a wireless network interface (e.g., operable via IEEE 802.11, ETSI GSM, BLUETOOTH™, satellite, etc.). As an example, a mobile device may include components such as a main processor, memory, a display, display graphics circuitry (e.g., optionally including touch and gesture circuitry), a SIM slot, audio/video circuitry, motion processing circuitry (e.g., accelerometer, gyroscope), wireless LAN circuitry, smart card circuitry, transmitter circuitry, GPS circuitry, and a battery. As an example, a mobile device may be configured as a cell phone, a tablet, etc. As an example, a method may be implemented (e.g., wholly or in part) using a mobile device. As an example, a system may include one or more mobile devices.

As an example, a system may be a distributed environment, for example, a so-called "cloud" environment where various devices, components, etc. interact for purposes of data storage, communications, computing, etc. As an example, a device or a system may include one or more components for communication of information via one or more of the Internet (e.g., where communication occurs via one or more Internet protocols), a cellular network, a satellite network, etc. As an example, a method may be implemented in a distributed environment (e.g., wholly or in part as a cloud-based service).

As an example, information may be input from a display (e.g., consider a touchscreen), output to a display or both. As an example, information may be output to a projector, a laser device, a printer, etc. such that the information may be viewed. As an example, information may be output stereographically or holographically. As to a printer, consider a 2D or a 3D printer. As an example, a 3D printer may include one or more substances that can be output to construct a 3D object. For example, data may be provided to a 3D printer to construct a 3D representation of a subterranean formation. As an example, layers may be constructed in 3D (e.g., horizons, etc.), geobodies constructed in 3D, etc. As an example, holes, fractures, etc., may be constructed in 3D (e.g., as positive structures, as negative structures, etc.).

Although only a few example embodiments have been described in detail above, those skilled in the art will readily appreciate that many modifications are possible in the example embodiments. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words "means for" together with an associated function.

What is claimed is:

1. A method comprising:
receiving data for a geologic environment wherein the data comprise data acquired via different types of borehole tool sensors;
based at least in part on the data, determining rock composition of the geologic environment wherein the rock composition comprises depositional components and diagenetic components, wherein the determining rock composition comprises determining detrital mineral composition values for trace minerals associated with at least one of the depositional components and calculating a detrital index value based at least in part on the detrital mineral composition values for the trace minerals; and
based at least in part on the rock composition, outputting a stratigraphic model of at least a portion of the geologic environment, wherein a portion of the stratigraphic model is attributed to a particular geological source based at least in part on the detrital index value.

2. The method of claim 1 wherein the determining rock composition comprises determining diagenetic mineral composition values associated with at least one of the diagenetic components, calculating a diagenetic index value based at least in part on the diagenetic mineral composition values and, based at least in part on the diagenetic index value, attributing a portion of the stratigraphic model to a particular geological source.

3. The method of claim 1 wherein the determining rock composition comprises determining diagenetic mineral composition values associated with at least one of the diagenetic components and calculating a diagenetic index value based at least in part on the diagenetic mineral composition values; and, based at least in part on the detrital index value and the diagenetic index value, attributing a portion of the stratigraphic model to a particular geological source.

4. The method of claim 3 wherein the detrital index value is normalized by a quartz composition value and wherein the diagenetic index value is normalized by a calcite composition value.

5. The method of claim 1 wherein the determining comprises elemental analysis.

6. The method of claim 1 wherein the stratigraphic model comprises a reservoir model, a completion model or a reservoir model and a completion model.

7. The method of claim 1 wherein the determining comprises determining that the rock composition of the geologic environment comprises at least one igneous deposit.

8. The method of claim 7 wherein the at least one igneous deposit comprises a weathered volcanic ash bed.

9. The method of claim 7 further comprising adjusting a completion plan based at least in part on the at least one igneous deposit.

10. The method of claim 7 wherein at least one of the at least one igneous deposit comprises a thickness less than approximately 10 cm.

11. The method of claim 1 wherein at least one of the different types of borehole tool sensors acquires raw data with a resolution less than approximately 10 cm.

12. The method of claim 1 wherein the different types of borehole tool sensors comprise at least one sensor selected from a group consisting of a micro-resistivity sensor, a photoelectric factor sensor, an image sensor, a dielectric and conductivity dispersion sensor, a neutron porosity sensor, and an ultrasonic sensor.

13. The method of claim 1 wherein the data comprise sonic data, NMR data and gamma ray spectroscopy data.

14. The method of claim 13 wherein the determining comprises determining at least one pore characteristic that comprises a surface to volume ratio or a volume to surface ratio based at least in part on a portion of the NMR data and determining at least one value for the Thomsen gamma parameter based at least in part on at least a portion of the sonic data.

15. The method of claim 1 wherein the data comprise counting rates in a formation for each of a plurality of radiation detectors.

16. The method of claim 15 wherein the determining comprises computing density values and photoelectric factor values based at least in part on the counting rates; applying density depth match filters to the density values to generated filtered density values; and applying photoelectric factor depth match filters to the photoelectric factor values to generate filtered photoelectric factor values wherein each of the radiation detectors is associated with a corresponding depth match filter and a corresponding photoelectric factor filter.

17. The method of claim 16 wherein the stratigraphic model is based at least in part on the generated filtered density values and the generated filtered photoelectric factor values.

18. The method of claim 1 wherein the detrital index value is normalized by a quartz composition value.

19. A system comprising:
a processor;
memory accessibly by the processor;
instructions stored in the memory and executable by the processor to instruct the system to:
  receive data for a geologic environment wherein the data comprise data acquired via different types of borehole tool sensors;
  based at least in part on the data, determine rock composition of the geologic environment wherein the rock composition comprises depositional components and diagenetic components and wherein to determine rock composition comprises determination of detrital mineral composition values for trace minerals associated with at least one of the depositional components and calculation of a detrital index value based at least in part on the detrital mineral composition values for the trace minerals; and
  based at least in part on the rock composition, output a stratigraphic model of at least a portion of the geologic environment, wherein a portion of the stratigraphic model is attributed to a particular geological source based at least in part on the detrital index value.

20. One or more non-transitory computer-readable storage media comprising processor-executable instructions wherein the processor-executable instructions comprise instructions to instruct a computer to:
receive data for a geologic environment wherein the data comprise data acquired via different types of borehole tool sensors;
based at least in part on the data, determine rock composition of the geologic environment wherein the rock composition comprises depositional components and diagenetic components and wherein to determine rock composition comprises determination of detrital mineral composition values for trace minerals associated with at least one of the depositional components and calculation of a detrital index value based at least in part on the detrital mineral composition values for the trace minerals; and
based at least in part on the rock composition, output a stratigraphic model of at least a portion of the geologic environment, wherein a portion of the stratigraphic model is attributed to a particular geological source based at least in part on the detrital index value.

* * * * *